(12) United States Patent
Levy et al.

(10) Patent No.: US 6,403,089 B1
(45) Date of Patent: Jun. 11, 2002

(54) METHODS OF MODULATING IMMUNE COAGULATION

(75) Inventors: Gary Levy, Thornhill; David A. Clark, Burlington, both of (CA)

(73) Assignee: Transplantation Technologies Inc., Toronto (CA)

(*) Notice: Subject to any disclaimer, the term of this patent is extended or adjusted under 35 U.S.C. 154(b) by 0 days.

(21) Appl. No.: 09/442,143

(22) Filed: Nov. 15, 1999

Related U.S. Application Data

(63) Continuation of application No. PCT/CA98/00475, filed on May 15, 1998.
(60) Provisional application No. 60/046,537, filed on May 15, 1997, and provisional application No. 60/061,684, filed on Oct. 10, 1997.

(51) Int. Cl.[7] ............................................. A61K 39/40
(52) U.S. Cl. ................................. 424/139.1; 424/152.1
(58) Field of Search ............................. 424/152.1, 139.1

(56) References Cited

PUBLICATIONS

Van Regenmortel, M. H. V, Methods: A Companion to Methods of Enzymology, 9:465–472, 1996.*

* cited by examiner

*Primary Examiner*—Patrick J. Nolan
(74) *Attorney, Agent, or Firm*—Bereskin & Parr; Micheline Gravelle

(57) ABSTRACT

Methods for mediating immune coagulation using novel antibodies and compounds are described. A protein Fgl2 having direct prothrombinase activity has been identified. Inhibitors of Fgl2 are useful in preventing and treating diseases which require a reduction in immune coagulation including bacterial and viral infections, allograft and xenograft rejection, glomerulonephritis, cancer, a number of gastrointestinal diseases and fetal loss.

4 Claims, 25 Drawing Sheets

FIGURE 2

```
                          10         20         30         40         50
MOUSE-X1.DNA     1 ATGAGGCTTC CTGGTTGGTT GTGGCTGAGT TCTGCCGTCC TCGCTGCCTG    50
HUMAN-X1.DNA     1 ATGAAGCTGG CTAACTGGTA CTGGCTGAGC TCAGCTGTTC TTGCCACTTA    50
                          60         70         80         90        100
MOUSE-X1.DNA    51 CCGAGC---G GTGGAGGAGC ACAACCTGAC TGAGGGGCTG GAGGATGCCA   100
HUMAN-X1.DNA    51 CGGTTTTTTG GTTGTGGCAA ACAATGAAAC AGAGGAAATT AAAGATGAAA   100
                         110        120        130        140        150
MOUSE-X1.DNA   101 GCGCCCAGGC TGCCTGCCCC GCGAGGCTGG AGGGCAGCGG GAGGTGCGAG   150
HUMAN-X1.DNA   101 GAGCAAAGGA TGTCTGCCCA GTGAGACTAG AAAGCAGAGG GAAATGCGAA   150
                         160        170        180        190        200
MOUSE-X1.DNA   151 GGGA----GCC AGTGCCCCTT CCAGCTCACC CTGCCCACGC TGACCATCCA   200
HUMAN-X1.DNA   151 GAGGCAGGGG AGTGCCCCTA CCAGGTAAGC CTGCCCCCCT TGACTATTCA   200
                         210        220        230        240        250
MOUSE-X1.DNA   201 GCTCCCGCGG CAGCTTGGCA GCATGGAGGA GGTGCTCAAA GAAGTGCGGA   250
HUMAN-X1.DNA   201 GCTCCCGAAG CAATTCAGCA GGATCGAGGA GGTGTTCAAA GAAGTCCAAA   250
                         260        270        280        290        300
MOUSE-X1.DNA   251 CCCTCAAGGA AGCAGTGGAC AGTCTGAAGA AATCCTGCCA GGACTGTAAG   300
HUMAN-X1.DNA   251 ACCTCAAGGA AATCGTAAAT AGTCTAAAGA AATCTTGCCA AGACTGCAAG   300
                         310        320        330        340        350
MOUSE-X1.DNA   301 TTGCAGGCTG ACGACCATCG AGATCCCGGC GGGAATGGAG GG--------   350
HUMAN-X1.DNA   301 CTGCAGGCTG ATGACAACGG AGACCCAGGC AGAAACGGAC TGTTGTTACC   350
                         360        370        380        390        400
MOUSE-X1.DNA   351 -AAT---GGA GC---AGAGA CAGCCGAGGA CAGTAGAGTC CAGGAACTGG   400
HUMAN-X1.DNA   351 CAGTACAGGA GCCCCGGGAG AGGTTGGTGA TAACAGAGTT AGAGAATTAG   400
                         410        420        430        440        450
MOUSE-X1.DNA   401 AGAGTCAGGT GAACAAGCTG TCCTCAGAGC TGAAGAATGC AAAGGACCAG   450
HUMAN-X1.DNA   401 AGAGTGAGGT TAACAAGCTG TCCTCTGAGC TAAAGAATGC CAAAGAGGAG   450
                         460        470        480        490        500
MOUSE-X1.DNA   451 ATCCAGGGGC TGCAGGGGCG CCTGGAGACG CTCCATCTGG TAAATATGAA   500
HUMAN-X1.DNA   451 ATCAATGTAC TTCATGGTCG CCTGGAGAAG CTGAATCTTG TAAATATGAA   500
                         510        520        530        540        550
MOUSE-X1.DNA   501 CAACATTGAG AACTACGTGG ACAACAAAGT GGCAAATCTA ACCGTTGTGG   550
HUMAN-X1.DNA   501 CAACATAGAA AATTATGTTG ACAGCAAAGT GGCAAATCTA ACATTTGTTG   550
                         560        570        580        590        600
MOUSE-X1.DNA   551 TCAACAGTTT GGATGGCAAG TGTTCCAAGT GTCCCAGCCA AGAACACATG   600
HUMAN-X1.DNA   551 TCAATAGTTT GGATGGCAAA TGTTCAAAGT GTCCCAGCCA AGAACAAATA   600
                         610        620        630        640        650
MOUSE-X1.DNA   601 CAGTCACAGC CGG.......  .......... .......... ..........   650
HUMAN-X1.DNA   601 CAGTCACGTC CAG.......  .......... .......... ..........   650
```

FIGURE 3

```
                         10         20         30         40         50
MOUSE-X2.DNA     1 TTCAACATCT AATATACAAA GATTGTTCCG ACCACTACGT GCTAGGAAGG    50
HUMAN-X2.DNA     1 TTCAACATCT AATATATAAA GATTGCTCTG ACTACTACGC AATAGGCAAA    50
                         60         70         80         90        100
MOUSE-X2.DNA    51 AGAAGCAGTG GGGCCTACAG AGTTACCCCT GATCACAGAA ACAGCAGCTT   100
HUMAN-X2.DNA    51 AGAAGCAGTG AGACCTACAG AGTTACACCT GATCCCAAAA ATAGTAGCTT   100
                        110        120        130        140        150
MOUSE-X2.DNA   101 TGAGGTCTAC TGTGACATGG AGACCATGGG TGGAGGCTGG ACGGTGCTGC   150
HUMAN-X2.DNA   101 TGAAGTTTAC TGTGACATGG AGACCATGGG GGGAGGCTGG ACAGTGCTGC   150
                        160        170        180        190        200
MOUSE-X2.DNA   151 AGGCTCGCCT TGATGGCAGC ACCAACTTCA CCAGAGAGTG GAAAGACTAC   200
HUMAN-X2.DNA   151 AGGCACGTCT CGATGGGAGC ACCAACTTCA CCAGAACATG GCAAGACTAC   200
                        210        220        230        240        250
MOUSE-X2.DNA   201 AAAGCCGGCT TTGGAAACCT TGAACGAGAA TTTTGGTTGG GCAACGATAA   250
HUMAN-X2.DNA   201 AAAGCAGGCT TTGGAAACCT CAGAAGGGAA TTTTGGCTGG GAACGATAA   250
                        260        270        280        290        300
MOUSE-X2.DNA   251 AATTCATCTT CTGACCAAGA GTAAGGAAAT GATTTTGAGA ATAGATCTTG   300
HUMAN-X2.DNA   251 AATTCATCTT CTGACCAAGA GTAAGGAAAT GATTCTGAGA ATAGATCTTG   300
                        310        320        330        340        350
MOUSE-X2.DNA   301 AAGACTTTAA TGGTCTCACA CTTTATGCCT TGTATGATCA GTTTTATGTG   350
HUMAN-X2.DNA   301 AAGACTTTAA TGGTGTCGAA CTATATGCCT TGTATGATCA GTTTTATGTG   350
                        360        370        380        390        400
MOUSE-X2.DNA   351 GCTAATGAAT TTCTCAAATA CCGATTACAC ATCGGTAACT ACAATGGCAC   400
HUMAN-X2.DNA   351 GCTAATGAGT TTCTCAAATA TCGTTTACAC GTTGGTAACT ATAATGGCAC   400
                        410        420        430        440        450
MOUSE-X2.DNA   401 GGCAGGGGAT GCCTTGCGTT TCAGTCGACA CTACAACCAT GACCTGAGGT   450
HUMAN-X2.DNA   401 AGCTGGAGAT GCATTACGTT TCAACAAACA TTACAACCAC GATCTGAAGT   450
                        460        470        480        490        500
MOUSE-X2.DNA   451 TTTTCACAAC CCCAGACAGA GACAACGATC GGTACCCCTC TGGGAACTGT   500
HUMAN-X2.DNA   451 TTTTCACCAC TCCAGATAAA GACAATGATC GATATCCTTC TGGGAACTGT   500
                        510        520        530        540        550
MOUSE-X2.DNA   501 GGGCTCTATT ACAGCTCAGG CTGGTGGTTT GATTCATGTC TCTCTGCCAA   550
HUMAN-X2.DNA   501 GGGCTGTACT ACAGTTCAGG CTGGTGGTTT GATGCATGTC TTTCTGCAAA   550
                        560        570        580        590        600
MOUSE-X2.DNA   551 CTTAAATGGC AAATATTACC ACCAGAAATA CAAAGGTGTC CGTAATGGGA   600
HUMAN-X2.DNA   551 CTTAAATGGC AAATATTATC ACCAAAAATA CAGAGGTGTC CGTAATGGGA   600
                        610        620        630        640        650
MOUSE-X2.DNA   601 TTTTCTGGGG CACCTGGCCT GGTATAAACC AGGCACAGCC AGGTGGCTAC   650
HUMAN-X2.DNA   601 TTTTCTGGGG TACCTGGCCT GGTGTAAGTG AGGCACACCC TGGTGGCTAC   650
                        660        670        680        690        700
MOUSE-X2.DNA   651 AAGTCCTCCT TCAAACAGGC CAAGATGATG ATTAGGCCCA AGAATTTCAA   700
HUMAN-X2.DNA   651 AAGTCCTCCT TCAAAGAGGC TAAGATGATG ATCAGACCCA AGCACTTTAA   700
                        710        720        730        740        750
MOUSE-X2.DNA   701 GCCATAA... .......... .......... .......... ..........   750
HUMAN-X2.DNA   701 GCCATAA... .......... .......... .......... ..........   750
```

```
         10         20         30         40         50         60
ATCACTCTGT TCATTCCTCC AGGTATTCGT TATCTAATAG GGCAATTAAT TCCTTCAGCA
         70         80         90        100        110        120
CTTTAGAATA TGCCTTGTTT CATATTTTTC ATAGCTAAAA AATGCCTTGT TTCATATTTT
        130        140        150        160        170        180
TCATAGCTAA AAAATGATGT CTGACGGCTA GGTTCTTATG CTACACAGCA TTTGAAATAA
        190        200        210        220        230        240
AGCTGAAAAA CAATGCATTT TAAAGGAGTC CTTTGTTGTT ATGCTGTTAT CCAATGAACA
        250        260        270        280        290        300
CTTGCAAGCA ATTAGCAATA TTGAGAATTA TACATTAGAT TTACAATTCT TTTAATTTCT
        310        320        330        340        350        360
ATTGAAACTT TTTCTATTGC TTGTATTACT TGCTGTATTT AAAAAATAAT TGTTGGCTGG
        370        380        390        400        410        420
GTGTGGTAGC TCACGCCTGT AATNCCAGCA CTTTGGAATG TCAAGGCAGG CAGATCACTT
        430        440        450        460        470        480
GAGGTCAGGA GTTTGAGACC AGCCTGGCCA AACATGTGAA ACGCTGTNTN TATTAAAAAT
        490        500        510        520        530        540
ACAAAAATTA GCCGGGCATG GTGGNACATG CCTGTAATCC TAGNTACTTG GGAGGCTGAG
        550        560        570        580        590        600
GCAGGAGAAT CGCTTGAACC TGAGAGGAAG AGGTTGCAGT GAGCCAAGAA TGAGCCACTG
        610        620        630        640        650        660
CACTCCAGCA TGGGTGACAG AGAAAACTCT GTCTCAAACA AAAAAATAAT AAAATTTATT
        670        680        690        700        710        720
CAGTAGGNTG GATTCTACAC AAAGTAATCT GTATTTGGGC CATGATTTAA GCACATCTGA
        730        740        750        760        770        780
AGGTATATCA CTCTTTTCAG GCTATAATTA TTTGGGTAAT CTTCATTCTG AGACAAACTT
        790        800        810        820        830        840
AATCTATATC ATTTACTTTG CAACAGAACA ACCCTACAGC ATTTTGGTTC CCAGACTAAG
        850        860        870        880        890        900
GGAACTAATA TCTATATAAT TAAACTTGTT CATTTATCAT TCATGAAATA TAAAATI.CTT
        910        920        930        940        950        960
GTCATTTAAA CCGTTAAAA ATGTGGTAGC ATAATGTCAC CCCAAAAAGC ATTCAGAAAG
        970        980        990       1000       1010       1020
CAATGTAACT GTGAAGACCA GGGTTTAAAG GTAATTCATT TATAGTTTAT AACTCCTTAG
       1030       1040       1050       1060       1070       1080
ATGTTTGATG TTGAAAACTG CTTTAACATG AA........ .......... ..........
```

3'UTR of hfgl2. The A at position 1 corresponds to position 1354 on the cDNA.

```
                      10         20         30         40         50
MOUSEPRO.AMI    1  .R.PG....  .AVL.ACR-A  .EEH...GL  E.AS.QAA..  A..L.GS...    50
HUMANPRO.AMI    1  .K.AN....  .AVL.TYGFL  .VAN...EI  K.ER.KDV..  V.L.SR...    50
                      60         70         80         90        100
MOUSEPRO.AMI   51  -GSQ..F.LT  ..T.TIQL.R  .LGSM....  .VRT..A..D  .LKKSCQ...   100
HUMANPRO.AMI   51  EAGE..Y.VS  ..P.TIQL.K  .FSRI....  ..QNLK.I..  .LKKSCQDC.   100
                     110        120        130        140        150
MOUSEPRO.AMI  101  .QADI.HR...  G.K-----GN  GAETAE.S.. Q.LES.VNKI  .SELKNA.DQ   150
HUMANPRO.AMI  101  .QADI.NG...  R.K.LLLPSTG APGEVG.N.. R.LE.E.NKI  .SELKNA.EE   150
                     160        170        180        190        200
MOUSEPRO.AMI  151  .QG.Q..L.T  .H.V......  .YV.N.VA..  .V.VNSL.G.  .SKCPSQ.HM   200
HUMANPRO.AMI  151  .NV.H.RL.K  .N.VN......  .YV.S.VA..  .F.VNSLDG.  .SKCPSQ.QI   200
                     210        220        230        240        250
MOUSEPRO.AMI  201  .S.PVQHL..  .DCSI.H.VL.  R.SSGA..V.  .LHR.SSFEV  .CDMETMGG.   250
HUMANPRO.AMI  201  .SRPVQHLI.  .DCSI.Y.AI.  K.SSET.V.V.  .LPKNSSFEV  .CDMETMGG.   250
                     260        270        280        290        300
MOUSEPRO.AMI  251  .TVLQARLD.  .TNFT..K.  .KAGFG..E.  .FWLGNDK..  .LTKSKEM..   300
HUMANPRO.AMI  251  .TVLQARLD.  .TNFT..Q.  .KAGFG..R.  .FWLGNDK..  .LTKSKEM..   300
                     310        320        330        340        350
MOUSEPRO.AMI  301  .IDLED...L  T.YALY..Y  .AN.FLKY..  .I..NYNGTA.  .ALR.SR...   350
HUMANPRO.AMI  301  .IDLED...V  E.YALY..Y  .AN.FLKY..  .V..NYNGTA.  .ALR.NK...   350
                     360        370        380        390        400
MOUSEPRO.AMI  351  .DI.R.....  R.NDPYP.G.  .GLYYSSG..  .S.LSAN.L.  .RYY.....K.  400
HUMANPRO.AMI  351  .DI.K.....  K.NDPYP.G.  .GLYYSSG..  .A.LSAN.L.  .RYY.....R.  400
                     410        420        430        440        450
MOUSEPRO.AMI  401  .R.GI.WGT.  .G.INQ.Q.GG  .KSSF..A..  .IRP..EK.* ..........   450
HUMANPRO.AMI  401  .R.GI.WGT.  .G.VSE.H.G.  .KSSF..A..  .IRP..EK.* ..........   450
```

FIGURE 6

```
                        10         20         30         40         50
MOUSEPRO.AMI    1  MRLPGWLWLS SAVLAACR-A VEEHNLTEGL EDASAQAACP ARLEGSGRCE   50
HUMANPRO.AMI    1  MKLANWYWLS SAVLATYGFL VVANNETEEI KDERAKDVCP VRLESRGKCE   50
                        60         70         80         90        100
MOUSEPRO.AMI   51  -GSQCPFQLT LPTLTIQLPR QLGSMEEVLK EVRTLKEAVD SLKKSCQDCK  100
HUMANPRO.AMI   51  EAGECPYQVS LPPLTIQLPK QFSRIEEVFK EVQNLKEIVN SLKKSCQDCK  100
                       110        120        130        140        150
MOUSEPRO.AMI  101  LQADDHRDPG GNG-----GN GAETAEDSRV QELESQVNKL SSELKNAKDQ  150
HUMANPRO.AMI  101  LQADDNGDPG RNGLLLPSTG APGEVGDNRV RELESEVNKL SSELKNAKEE  150
                       160        170        180        190        200
MOUSEPRO.AMI  151  IQGLQGRLET LHLVNMNNIE NYVDNKVANL TVVVNSLDGK CSKCPSQEHM  200
HUMANPRO.AMI  151  INVLHGRLEK LNLVNMNNIE NYVDSKVANL TFVVNSLDGK CSKCPSQEQI  200
                       210        220        230        240        250
MOUSEPRO.AMI  201  QSQPVQHLIY KDCSDHYVLG RRSSGAYRVT PDHRNSSFEV YCDMETMGGG  250
HUMANPRO.AMI  201  QSRPVQHLIY KDCSDYYAIG KRSSETYRVT PDPKNSSFEV YCDMETMGGG  250
                       260        270        280        290        300
MOUSEPRO.AMI  251  WTVLQARLDG STNFTREWKD YKAGFGNLER EFWLGNDKIH LLTKSKEMIL  300
HUMANPRO.AMI  251  WTVLQARLDG STNFTRTWQD YKAGFGNLRR EFWLGNDKIH LLTKSKEMIL  300
                       310        320        330        340        350
MOUSEPRO.AMI  301  RIDLEDFNGL TLYALYDQFY VANEFLKYRL HIGNYNGTAG DALRFSRHYN  350
HUMANPRO.AMI  301  RIDLEDFNGV ELYALYDQFY VANEFLKYRL HVGNYNGTAG DALRFNKHYN  350
                       360        370        380        390        400
MOUSEPRO.AMI  351  HDLRFFTTPD RDNDRYPSGN CGLYYSSGWW FDSCLSANLN GKYYHQKYKG  400
HUMANPRO.AMI  351  HDLKFFTTPD KDNDRYPSGN CGLYYSSGWW FDACLSANLN GKYYHQKYRG  400
                       410        420        430        440        450
MOUSEPRO.AMI  401  VRNGIFWGTW PGINQAQPGG YKSSFKQAKM MIRPKNFKP* ..........  450
HUMANPRO.AMI  401  VRNGIFWGTW PGVSEAHPGG YKSSFKEAKM MIRPKHFKP* ..........  450
```

FIGURE 7

```
              10        20        30        40        50        60        70
       MKLANWYNLSSAVLATYGFLVVANNETEEIKDERAKDVCPVRLESRGKCEEAGECPYQVSLPPLTIQLPK
HELIX  HHhhhhhhhhhhhhhhhhhhhhhhHHhhhhHHHHHHHHHH                              hh
SHEET  SSSSSSSSSSSSsssssSSSs               SSSSSS             ssssSSSssssSSsss
TURN              TTTT    TTTT                   TTTTTTT    TTTT    TTTT  TTT
COIL                                       c                CCCC 80        90       100       110       120       130       140
       QFSRIEEVFKEVQNLKEIVNSLKKSCQDCKLQADDNGDPGRNGLLLPSTGAPGEVGDNRVRELESEVNKL
HELIX  hHHHHHHHHHHHHHHHHHHH                                         HHHHHHHHH
SHEET  sssssssssssssssssssss       sSs          sSs
TURN   T                    TTTTTTTTTTT  TTTTTTTTTTT  TTTTTTTTTTTT
COIL                                                                        CCC 150       160       170       180       190       200       210
       SSELKNAKEEINVLHGRLEKLNLVRMNHIENYVDSKVANLTFVVNSLDGKCSKCPSQEQIQSRPVQHLIY
HELIX     HHHHHHHHHhhhHhhhhHHhhhhhh         hhhhhhhhhh          hhhhhhhhhhhhhh
SHEET            SSSs     SSSSsssssSSSSs   sSSSSSSSSs         sSSSSSSSSSSSSSs
TURN            TTTT     TTTT   TTTTT         TTTTTTTTTTT                   T
COIL   CC 220       230       240       250       260       270       280
       KDCSDYYAIGKRSSETYRVTPDPKNSSFEVYCDMETMGGGWTVLQARLDGSTNFTRTWQDYKAGFGNLRR
HELIX  h                                  h   hhhhhhhh    hhhH             HHH
SHEET  s   sSS      sSSSs       sSSSSSSSs   sSSSSSSs    sSSss
TURN   TTTTTTT  TTTTTTT   TTTTTTTTT       TTTTT      TTTTTT    TTTTT
COIL                                                                      CCCCC 290       300       310       320       330       340       350
       EFWLGNDKIHLLTKSKEMILRIDLEDFNGVELYALYDQFYVANEFLKYRLHVGNYNGTAGDALRFNKHYN
HELIX  HHHh    hhhhhhhhhHhhhhhhhHHhhhhhhhhhhhhhhhhhhhhhhhhHH
SHEET  ssss    SSSSs    SSSSSSs       SSSSSSSSSSSSSSSSSSsSSSss
TURN       TTTTT    TTTT       TTTT                            TTTTTTTTTT  TTTTT
COIL                                                               CCCC 360       370       380       390       400       410       420
       HDLKFFTTPDKDNDRYPSGNCGLYYSSGWWFDACLSANLNGKYYHQKYRGVRNGIFWGTWPGVSEAHPGG
HELIX      hhhhhhh                    hhhhhHh                         hhhHHHHh
SHEET  ssSSSSs           sSs     sSSSSs         sSSSSSSsssSSSSSssss
TURN   TTT    TTTTTTTTTTTTTTT  TTTTT        TTTTTTTT       TTTT    TTTT    TTT 430       440
       YKSSFKEAKMMIRPKHFKP*
HELIX      hhHHHHHHH
SHEET        sss
TURN   TTTTTT      TTTT
COIL                  CCC
```

FIGURE 8A

```
                          10         20         30         40         50
MOUSEPRO.DNA     1 TCGGTTTGGA TATCATGGGA TG-GAATGAG AAGGGA-AAG TAGGAGCCCG    50
HUMANPRO.DNA     1 TAGGGTTGGA AGCCAGGTCT CCTGAGTATG CGAGAATAAA TACAGTCATG    50
                          60         70         80         90        100
MOUSEPRO.DNA    51 AGAGTGCGGT AAGACAA--G GCATAAGGCG TGTCTGACAA ATTCTTCATA   100
HUMANPRO.DNA    51 GAAGTGTAAA GAGTCTGCCA ACATTTTGAG AATGTGAATA GGATTTGGC-   100
                         110        120        130        140        150
MOUSEPRO.DNA   101 CACACATTTC CCCTTTGCAC ATTCAGTCTG TATAGGTTAT TTCTATAGGA   150
HUMANPRO.DNA   101 TA-AAATTAA GGGGATATAC AGAAAAGTCA TAGGAAATCA GGTTAAAGAC   150
                         160        170        180        190        200
MOUSEPRO.DNA   151 GAAAAAAAAT ATTCAAATTC CTTGTGCACT G-GTAACAGG CATGAAGGCT   200
HUMANPRO.DNA   151 ATAAATATGA GATAGGCTAC AGAGTGTTTT AAGTAATACA ATAAAACATT   200
                         210        220        230        240        250
MOUSEPRO.DNA   201 CAGCAAAGCC AATACGTGTT ATGTCCAGTT GGAGACAGTG CCAGGGCCAA   250
HUMANPRO.DNA   201 TAG--ATTTT TGCCCATGTC A-GTCATTTT GAAATTATTT TTAAAGCAAA   250
                         260        270        280        290        300
MOUSEPRO.DNA   251 CATTCCAGAC TTCTCAGATA GAAAGTGCGC CTGCCTGCCC -TGCTCTGAG   300
HUMANPRO.DNA   251 AAAACC---C TTTTTAAACA AGAAATCTTA TGAGATGTCA ATATGCAAAA   300
                         310        320        330        340        350
MOUSEPRO.DNA   301 --AATTTGAA GAGAGTAGTT C----AGTTA GAATTAAGAG GCAGTAGAGA   350
HUMANPRO.DNA   301 CAAATTAAAA GGAGGTGGTT TCTCTAACTG AAGCTGTTCC TCTTTCCTGC   350
                         360        370        380        390        400
MOUSEPRO.DNA   351 AA--AGTCTT GGGAAATCTG GTTAGAGA-- TATAAATATG AGAACTGGAC   400
HUMANPRO.DNA   351 CTTCAGCCTC TGAAGAGAAA GTTAGAAAAC TATTATCATT AATGCTACAT   400
                         410        420        430        440        450
MOUSEPRO.DNA   401 ATGGTGGTAC ACACCTGTGA TCTCTGTGTT TAGGAGGGAG AGGCAGAGAG   450
HUMANPRO.DNA   401 GTTTTGA-AC AAGCTGATAT ACCAAGTGGC CCAGAGAGC- AGGTAGAAGA   450
                         460        470        480        490        500
MOUSEPRO.DNA   451 ATCAGGAGTT CAAGGCCAGC CTGAGCTACT TGAGACCCAG TCTAAATAAA   500
HUMANPRO.DNA   451 ACCAGCG--- TGGAGACAGA --AAGCAA-- -GAGGCCC-G CCTGCCAGGG   500
                         510        520        530        540        550
MOUSEPRO.DNA   501 TAAGAGATAG ATTACAGAGT GCCTTTAACT AGTACAGAGA AAGAATTTGG   550
HUMANPRO.DNA   501 CTACCTGCAG AA-AGAAAGG GCAAAGATGC TGTAGGCAAG AGAAGTTCAG   550
                         560        570        580        590        600
MOUSEPRO.DNA   551 GTTTATCTGT GTCAGTTACG CTGAAATAAT TTTTAAGTAA TAAAATCCCT   600
HUMANPRO.DNA   551 GACAGACACT GGCA--TA-G CTCAAA-GAT TCACATTTGA GCAG-----C   600
                         610        620        630        640        650
MOUSEPRO.DNA   601 TTTAATAAGA AACCTTATGA G-GTCAGTAT GCACAATGAA CTTAAGAGAG   650
HUMANPRO.DNA   601 TGTGGAAGAT GACAGTACAA TTACCAAAAT GT-CGAAGGG C--AAAGGAG   650
                         660        670        680        690        700
MOUSEPRO.DNA   651 ACCCCCAGCT CCTGAGCTGA GTGATGGGGA AGGACAGCCA CTGCCTGTGA   700
HUMANPRO.DNA   651 GC----AGCT ACTGGTTT-- -TGATG---A AAGACAATTA TGTCCTTT--   700
                         710        720        730        740        750
MOUSEPRO.DNA   701 TGTGTGAGTG ACGTGCTTCC AAGTGTTTTA ACCACTGACG ATTACATAGC   750
HUMANPRO.DNA   701 TAAATGGGTC TTAGACATTT AGACATTTAT AT-AC--ACT ATGCTACGGA   750
                         760        770        780        790        800
MOUSEPRO.DNA   751 CTGCACAGTC AGGAGAAAAC AGCCGTATTC TCTGCCAGTT CTCTTCCCTT   800
HUMANPRO.DNA   751 CAAAGGAAT- AGAAAGTAGC A-CTTTTTC TCCACTAGTT TTCTTCTCTT   800
                         810        820        830        840        850
MOUSEPRO.DNA   801 TTACAAACAG ATGAGAGACA CACACAGAGA ATCCATTTAA AGAGCGGACC   850
HUMANPRO.DNA   801 TTTCAAGTAG ATGAAGCAAA AGT-CAACTG CAATAGTCAG AAAGCTGTAC   850
                         860        870        880        890        900
```

FIGURE 8B

```
MOUSEPRO.DNA   851 TTTGTTCTGA TTAGGGGCAA TTTTAAGTAC TTAAGAGTTC ACACAAAGTC   900
HUMANPRO.DNA   851 TTTGTTACAC TTAGAAACTT CTAAAAGTGC TTAAGATTTC ACCTGAAAGT   900
                    910        920        930        940        950
MOUSEPRO.DNA   901 TAGCCTTCAA AAAGAAAACA GGTTCCCAAA ----CTA--- -GGGAGGAAA   950
HUMANPRO.DNA   901 CCAACAT-GA AGAAAATACA GGCTCCCCAA TGCCCCATTC TAAGAAGAAA   950
                    960        970        980        990       1000
MOUSEPRO.DNA   951 CAGAATCATT TCCATTTTGG TGACATTTA- GTGGGAAGAA GCTCACAGAC  1000
HUMANPRO.DNA   951 AAGGACCATT TTCATTTTAG TAACGTTTCT GTTCTATAGA CAGTTTGGAT  1000
                   1010       1020       1030       1040       1050
MOUSEPRO.DNA  1001 ATTTAGACGT TCCAACTCTT TCCCCACTAG TG-------G ACCAAGT-AT  1050
HUMANPRO.DNA  1001 AACTAGCTCT TACTTTTTAT CTTTAAAAAC TGTTTTTCCA GTGAAGTTAC  1050
                   1060       1070       1080       1090       1100
MOUSEPRO.DNA  1051 ATAATATGGT ATCTTTTGGG CACTGGTATT ACAA-CTGTT TTTTAAACAA  1100
HUMANPRO.DNA  1051 GTATAATTAT TTACTTCAAG CG-TAGTATA CCAAATTACT TTAGAAATGC  1100
                   1110       1120       1130       1140       1150
MOUSEPRO.DNA  1101 AAGACTTTCC TTGTGCTTTA CTAAAAAC-C CA-GACGGTG AATCTTGAAT  1150
HUMANPRO.DNA  1101 AAGACTTTTC TTATACTTCA TAAAATACAT TATGAAAGTG AATCTTG--T  1150
                   1160       1170       1180       1190       1200
MOUSEPRO.DNA  1151 ACAATGCGTG GCACCCACGG CAGGCATTCT ATTGTGCATA GTTTTGACTG  1200
HUMANPRO.DNA  1151 TGGCTGTGTA CATTTGACTA TAATAATTTC AATGCATATT ATTTCTATTG  1200
                   1210       1220       1230       1240       1250
MOUSEPRO.DNA  1201 ACAGGAGATG ACAGCATTTG GCTGGCTGCG CTTGCTGAGG ACCCTCTCCT  1250
HUMANPRO.DNA  1201 AGAGTAAGTT ACAGTTTTTG GCAAACTGCG TTTGATGAGG GCTATCTCCT  1250
                   1260       1270       1280       1290       1300
MOUSEPRO.DNA  1251 CCTG-TGTG- GCGTCTGAGA CT-GTGATGC AAATGCGCCC GCCCTTTTCT  1300
HUMANPRO.DNA  1251 CTTCCTGTGC GTTTCTAAAA CTTGTGATGC AAACGCTCCC ACCCTTTCCT  1300
                   1310       1320       1330       1340       1350
MOUSEPRO.DNA  1301 GGGAACTCAG AACGCCTGAG TCAGGCGGCG GTGGCTATTA AAGCG-----  1350
HUMANPRO.DNA  1301 GGGAACACAG AAAGCCTGAG TCAGGCCATG GCCGCTATTA AAGCAGCTCC  1350
                   1360       1370       1380       1390       1400
MOUSEPRO.DNA  1351 ---CCTGGTC AG-----GCT GGGCT-GCCG CACTGCAAGG ATG.......  1400
HUMANPRO.DNA  1351 AGCCCTGCGC ACTCCCTGCT GGGTGAGCAG CACTGTAAAG ATG.......  1400
```

FIGURE 9A

```
         10        20         30        40        50
TAGGGTTGGAAGCCAGGTCTCCTGAGTATGCGAGAATAAATACAGTCATG
         60        70        80        90       100
GAAGTGTAAAGAGTCTGCCAACATTTTGAGAATGTGAATAGGATTTGGCT
        110       120       130       140       150
AAAATTAAGGGGATATACAGAAAAGTCATAGGAAATCAGGTTAAAGACAT
                             TCF1   PEA3
        160       170       180       190       200
AAATATGAGATAGGCTACAGAGTGTTTTAAGTAATACAATAAAACATTTA
         GATA1              NF IL6
        210       220       230       240       250
GATTTTGCCCATGTCAGTCATTTTGAAATTATTTTTAAAGCAAAAAAAC
                       NF IL6
        260       270       280       290       300
CCTTTTTAAACAAGAAATCTTATGAGATGTCAATATGCAAAACAAATTAA 310       320       330       340       350
AAGGAGGTGGTTTCTCTAACTGAAGCTGTTCCTCTTTCCTGCCTTCAGCC
TCF1
        360       370       380       390       400
TCTGAAGAGAAAGTTAGAAAACTATTATCATTAATGCTACATGTTTTGAA
                           NF_E1
        410       420       430       440       450
CAAGCTGATATACCAAGTGGCCCAGAGAGCAGGTAGAAGAACCAGCGTGG
              bHLH
        460       470       480       490       500
AGACAGAAAGCAAGAGGCCCGCCTGCCAGGGCTACCTGCAGAAAGAAAGG
                                        NF IL6
        510       520       530       540       550
GCAAAGATGCTGTAGGCAAGAGAAGTTCAGGACAGACACTGGCATAGCTC
TCF1
        560       570       580       590       600
AAAGATTCACATTTGAGCAGCTGTGGAAGATGACAGTACAATTACCAAAA
TCF1       bHLH   bHLH
                  E2A
        610       620       630       640       650
TGTCGAAGGGCAAAGGAGGCAGCTACTGGTTTTGATGAAAGACAATTATG
           TCF1                   NF IL6
        660       670       680       690       700
TCCTTTTAAATGGGTCTTAGACATTTAGACATTTATATACACTATGCTAC
        710       720       730       740       750
GGACAAAGGAATAGAAAGTAGCACTTTTTTCTCCACTAGTTTTCTTCTCT
   TCF1
        760       770       780       790       800
TTTTCAAGTAGATGAAGCAAAAGTCAACTGCAATAGTCAGAAAGCTGTAC
                       TCF1  bHLH
```

FIGURE 9B

```
       810       820       830       840       850
TTTGTTACACTTAGAAACTTCTAAAAGTGCTTAAGATTTCACCTGAAACG
                                    TCF1     bHLH
       860       870       880       890       900
CCAACATGAAGAAAATACAGGCTCCCCAATGCCCCATTCTAAGAAGAAAA
       910       920       930       940       950
AGGACCATTTTCATTTTAGTAACGTTTCTGTTCTATAGACAGTTTGGATA
       960       970       980       990      1000
ACTAGCTCTTACTTTTATCTTTAAAAACTGTTTTCCAGTGAAGTTACG
      1010      1020      1030      1040      1050
TATAATTATTTACTTCAAGCGTAGTATACCAAATTACTTTAGAAATGCAA
                                         NF IL6
      1060      1070      1080      1090      1100
GACTTTTCTTATACTTCATAAATACATTATGAAAGTGAATCTTGTTGGC
                               NF IL6
      1110      1120      1130      1140      1150
TGTGTACATTTGACTATAATAATTTCAATGCATATTATTTCTATTGAGAG
      bHLH
      1160      1170      1180      1190      1200
TAAGTTACAGTTTTTGGCAAACTGCGTTTGATGAGGGCTATCTCCTCTTC
      1210      1220      1230      1240      1250
CTGTGCGTTTCTAAAACTTGTGATGCAAACGCTCCCACCCTTTCCTGGGA
                       AABS
      1260      1270      1280      1290      1300
ACACAGAAACGCTGACTCAGGCACGTGCCGCTATTAAAGCAGCTCCAGCC
  +1        AP 1     bHLH      TATA box
      1310      1320      1330
CTGCGCACTCCCTGCTGGGTGAGCAGCACTGTAAAGATG
```

Prevention of CsA Graft Rejection by CsA Alone or in Combination with Antibodies to Immune Coagulants

FIGURE 17

```
5'-- CCAAGTATAT AATATGGTAT CTTTTGGGCA CTGGTATTAC AACTGTTTTT -270
    TAAACAAAAG ACTTTCCTTG TGCTTTACTA AAAACCCAGA CGGTGAATCT -220
    TGAATACAAT GCGTGGCACC CACGGCAGGC ATTCTATTGT GCATAGTTTT -170
    GACTGACAGG AGATGACAGC ATTTGGCTGC GTGCGCTTGC TGAGGACCCT -120
    CTCCTCCTGT GTGGCGTCTG AGACTGTGAT GCAAATGCGC CCGCCCTTTT -70
    CTGGGAACTC AGAANGCCTG AGTCAGGCGG CGGTGGCTAT TAAAGCGCCT -20
    GGTCAGGCTG GGCTGCCGCA CTCCAAGG--3'
                            ↳
                            +1
```

Prevention of Fetal Loss by Monoclonal Antibody 3D4.3

97.6 kDa →
60 kDa →
46 kDa →
30 kDa →

1  2  3

The lanes are:
1. H5cells
2. H5 + wild type virus
3. H5 + recombinant virus

The lanes are:
1. H5cells
2. H5 + wild type virus
3. H5 + recombinant virus

The lanes are:
1. 125I-Prothrombin (PT)
2. PT + RVV + Factor X
3. PT + H5
4. PT + H5-RV
5. PT + purified protein (3 µg)

SEQUENCE LISTING

<160> NUMBER OF SEQ ID NOS: 53

<210> SEQ ID NO 1
<211> LENGTH: 4630
<212> TYPE: DNA
<213> ORGANISM: Homo sapiens

<400> SEQUENCE: 1

```
gatctagggt tggaagccag gtctcctgag tatgcgagaa taaatacagt c atggaagtg      60
taaagagtct gccaacattt tgagaatgtg ataggattt ggctaaaatt a agggatat     120
acagaaaagt cataggaaat caggttaaag acataaaatat gagataggct a cagagtgtt   180
ttaagtaata caataaaaca tttagatttt tgcccatgtc agtcattttg a aattatttt   240
taaagcaaaa aaacccttttt taaacaagaa atcttatgag atgtcaatat g caaaacaaa  300
ttaaaaggag gtggtttctc taactgaagc tgttcctctt tcctgccttc a gcctctgaa   360
gagaaagtta gaaaactatt atcattaatg ctacatgttt tgaacaagct g atataccaa   420
gtggcccaga gagcaggtag aagaaccagc gtggagacag aaagcaagag g cccgcctgc   480
cagggctacc tgcagaaaga aagggcaaag atgctgtagg caagagaagt t caggacaga   540
cactggcata gctcaaagat tcacatttga gcagctgtgg aagatgacag t acaattacc   600
aaaatgtcga agggcaaagg aggcagctac tggttttgat gaaagacaat t atgtccttt   660
taaatgggtc ttagacattt agacatttat atacactatg ctacggacaa a ggaatagaa   720
agtagcactt ttttctccac tagttttctt ctcttttttca agtagatgaa g caaaagtca   780
actgcaatag tcagaaagct gtactttgtt acacttagaa acttctaaaa g tgcttaaga   840
tttcacctga aagtccaaca tgaagaaaat acaggctccc caatgcccca t tctaagaag   900
gaaaaaggac catttttcatt ttagtaacgt ttctgttcta tagacagttt g gataactag   960
ctcttacttt ttatctttaa aaactgttttt tccagtgaag ttcgtataa t tatttactt  1020
caagcgtagt ataccaaatt actttagaaa tgcaagactt ttcttatact t cataaaata  1080
cattatgaaa gtgaatcttg ttggctgtgt acatttgact ataataattt c aatgcatat  1140
tatttctatt gagagtaagt tacagttttt ggcaaactgc gtttgatgag g ctatctcc   1200
tcttcctgtg cgtttctaaa acttgtgatg caaacgctcc cacccttttcc t gggaacaca  1260
```

-continued

```
gaaagcctga ctcaggccat ggccgctatt aaagcagctc cagccctgcg c actccctgc   1320 tgggtgagc agcactgtaa agatgaagct ggctaactgg tactggctga g ctcagctgt    1380 tcttgccact tacggttttt tggttgtggc aaacaatgaa acagaggaaa t taaagatga   1440 aagagcaaag gatgtctgcc cagtgagact agaaagcaga gggaaatgcg a agaggcagg   1500 ggagtgcccc taccaggtaa gcctgccccc cttgactatt cagctcccga a gcaattcag   1560 caggatcgag gaggtgttca aagaagtcca aaacctcaag gaaatcgtaa a tagtctaaa   1620 gaaatcttgc caagactgca agctgcaggc tgatgacaac ggagacccag g cagaaacgg   1680 actgttgtta cccagtacag gagccccggg agaggttggt gataacagag t tagagaatt   1740 agagagtgag gttaacaagc tgtcctctga gctaaagaat gccaaagagg a gatcaatgt   1800 acttcatggt cgcctggaga agctgaatct tgtaaatatg aacaacatag a aaattatgt   1860 tgacagcaaa gtggcaaatc taacatttgt tgtcaatagt ttggatggca a atgttcaaa   1920 gtgtcccagc caagaacaaa tacagtcacg tccaggtatg tataataatg t tttcttatc   1980 atatgttcat aaatgttata cagtcagaga tgtatctaaa agattaacct g agtcagtaa   2040 gttaaataga tgacagatta agtcttttat ttatcaaggt gcacaggaaa a aataaatat   2100 cttctcaaat atgaccacat aaatatgacc taattacaaa atcatagtta g ttctgtatc   2160 cactggaagt cactttcaat tttaagatct tatttgttaa tgccagacct a cttgcaagc   2220 agagattaga ggtcctttct gctttataac attaggttct tcttgtgagg c cttaagcat   2280 ttactaaaca ccttcaagta agtttagtaa agtttcatta ctgccattga t tcaattatc   2340 aaactgcttt tgtacatata aagaattctt cagatgcatg gtttctatta a caagatcca   2400 atgccttcct tttatttccc cttcagttca acatctaata tataaagatt g ctctgacta   2460 ctacgcaata ggcaaaagaa gcagtgagac ctacagagtt acacctgatc c caaaaatag   2520 tagctttgaa gtttactgtg acatggagac catgggggga ggctggacag t gctgcaggc   2580 acgtctcgat gggagcacca acttcaccag aacatggcaa gactacaaag c aggctttgg   2640 aaacctcaga agggaatttt ggctggggaa cgataaaatt catcttctga c caagagtaa   2700 ggaaatgatt ctgagaatag atcttgaaga ctttaatggt gtcgaactat a tgccttgta   2760 tgatcagttt tatgtggcta atgagtttct caaatatcgt ttacacgttg g taactataa   2820 tggcacagct ggagatgcat acgtttcaa caaacattac aaccacgatc t gaagttttt   2880 caccactcca gataaagaca atgatcgata tccttctggg aactgtgggc t gtactacag   2940 ttcaggctgg tggtttgatg catgtctttc tgcaaactta aatggcaaat a ttatcacca   3000 aaaatacaga ggtgtccgta atgggatttt ctggggtacc tggcctggtg t aagtgaggc   3060 acaccctggt ggctacaagt cctccttcaa agaggctaag atgatgatca g acccaagca   3120 ctttaagcca taaatcactc tgttcattcc tccaggtatt cgttatctaa t agggcaatt   3180 aattccttgt tcatattttt tcatagctaa aaaatgatgt ctgacggcta g gttcttatg   3240 ctacacagca tttgaaataa agctgaaaaa caatgcattt taaaggagtc c tttgttgtt   3300 atgctgttat ccaatgaaca cttgcaagca attagcaata ttgagaatta t acattagat   3360 ttacaattct tttaatttct attgaaactt tttctattgc ttgtattact t gctgtattt   3420 aaaaaataat tgttggctgg gtgtggtagc tcacgcctgt aatcccagca c tttggaatg   3480 tcaaggcagg cagatcactt gaggtcagga gtttgagacc agcctggcca a acatgtgaa   3540 acgctgtctc tattaaaaat acaaaaatta gccgggcatg gtggtacatg c ctgtaatca   3600 acgctgttta ttaaaaatac aaaaattagc cgggcatggt ggacatgcct g taatcctag   3660
```

-continued

```
tacttgggag gctgaggcag gagaatcgct tgaacctgag aggaagaggt t gcagtgagc      3720 caagaatgag ccactgcact ccagcatggg tgacagagaa aactctgtct c aaacaaaaa      3780 aataataaaa tttattcagt aggtggattc tacacaaagt aatctgtatt t gggccatga      3840 tttaagcaca tctgaaggta tatcactctt ttcaggctat aattatttgg g taatcttca      3900 ttctgagaca aacttaatct atatcattta ctttgcaaca gaacaaccct a cagcatttt      3960 ggttcccaga ctaagggaac taatatctat ataattaaac ttgttcattt a tcattcatg      4020 aaatataaaa tacttgtcat ttaaaccgtt taaaaatgtg gtagcataat g tcacccaa       4080 aaagcattca gaaagcaatg taactgtgaa gaccagggtt taaaggtaat t catttatag     4140 tttataactc cttagatgtt tgatgttgaa aactgcttta acatgaaaat t atcttcctc    4200 tgctctgtgt gaacaatagc ttttaattta agattgctca ctactgtact a gactactgg    4260 taggtttttt tgggggggg tgggtaggga tatgtgggta atgaagcatt t acttacagg     4320 ctatcatact ctgaggccaa ttttatctcc aaagcaataa tatcattaag t gattcactt    4380 catagaaggc taagtttctc taggacagat agaaaacatg aattttgaaa t atatagaac    4440 agtagttaaa atactatata tttcaaccct ggctggtaga ttgcttattt t actatcaga   4500 aactaaaaga tagattttta cccaaacaga agtatctgta attttttataa t tcatcaatt    4560 ctggaatgct atatataata tttaaaagac ttttttaaatg tgtttaattt c atcatcgta    4620 aaaagggatc                                                             4630
```

<210> SEQ ID NO 2
<211> LENGTH: 439
<212> TYPE: PRT
<213> ORGANISM: Homo sapiens fgl2

<400> SEQUENCE: 2

```
Met Lys Leu Ala Asn Trp Tyr Trp Leu Ser S er Ala Val Leu Ala Thr
1               5                   10                  15

Tyr Gly Phe Leu Val Val Ala Asn Asn Glu T hr Glu Glu Ile Lys Asp
            20                  25                  30

Glu Arg Ala Lys Asp Val Cys Pro Val Arg L eu Glu Ser Arg Gly Lys
        35                  40                  45

Cys Glu Glu Ala Gly Glu Cys Pro Tyr Gln V al Ser Leu Pro Pro Leu
    50                  55                  60

Thr Ile Gln Leu Pro Lys Gln Phe Ser Arg I le Glu Glu Val Phe Lys
65                  70                  75                  80

Glu Val Gln Asn Leu Lys Glu Ile Val Asn S er Leu Lys Lys Ser Cys
                85                  90                  95

Gln Asp Cys Lys Leu Gln Ala Asp Asp Asn G ly Asp Pro Gly Arg Asn
            100                 105                 110

Gly Leu Leu Leu Pro Ser Thr Gly Ala Pro G ly Glu Val Gly Asp Asn
        115                 120                 125

Arg Val Arg Glu Leu Glu Ser Glu Val Asn L ys Leu Ser Ser Glu Leu
    130                 135                 140

Lys Asn Ala Lys Glu Glu Ile Asn Val Leu H is Gly Arg Leu Glu Lys
145                 150                 155                 160

Leu Asn Leu Val Asn Met Asn Asn Ile Glu A sn Tyr Val Asp Ser Lys
                165                 170                 175

Val Ala Asn Leu Thr Phe Val Val Asn Ser L eu Asp Gly Lys Cys Ser
            180                 185                 190
```

Lys Cys Pro Ser Gln Glu Gln Ile Gln Ser Arg Pro Val Gln His Leu
            195                 200                 205

Ile Tyr Lys Asp Cys Ser Asp Tyr Tyr Ala Ile Gly Lys Arg Ser Ser
            210                 215                 220

Glu Thr Tyr Arg Val Thr Pro Asp Pro Lys Asn Ser Ser Phe Glu Val
225                 230                 235                 240

Tyr Cys Asp Met Glu Thr Met Gly Gly Gly Trp Thr Val Leu Gln Ala
            245                 250                 255

Arg Leu Asp Gly Ser Thr Asn Phe Thr Arg Thr Trp Gln Asp Tyr Lys
            260                 265                 270

Ala Gly Phe Gly Asn Leu Arg Arg Glu Phe Trp Leu Gly Asn Asp Lys
            275                 280                 285

Ile His Leu Leu Thr Lys Ser Lys Glu Met Ile Leu Arg Ile Asp Leu
            290                 295                 300

Glu Asp Phe Asn Gly Val Glu Leu Tyr Ala Leu Tyr Asp Gln Phe Tyr
305                 310                 315                 320

Val Ala Asn Glu Phe Leu Lys Tyr Arg Leu His Val Gly Asn Tyr Asn
            325                 330                 335

Gly Thr Ala Gly Asp Ala Leu Arg Phe Asn Lys His Tyr Asn His Asp
            340                 345                 350

Leu Lys Phe Phe Thr Thr Pro Asp Lys Asp Asn Asp Arg Tyr Pro Ser
            355                 360                 365

Gly Asn Cys Gly Leu Tyr Tyr Ser Ser Gly Trp Trp Phe Asp Ala Cys
            370                 375                 380

Leu Ser Ala Asn Leu Asn Gly Lys Tyr Tyr His Gln Lys Tyr Arg Gly
385                 390                 395                 400

Val Arg Asn Gly Ile Phe Trp Gly Thr Trp Pro Gly Val Ser Glu Ala
            405                 410                 415

His Pro Gly Gly Tyr Lys Ser Ser Phe Lys Glu Ala Lys Met Met Ile
            420                 425                 430

Arg Pro Lys His Phe Lys Pro
            435

<210> SEQ ID NO 3
<211> LENGTH: 5403
<212> TYPE: DNA
<213> ORGANISM: Murine

<400> SEQUENCE: 3

```
cataaggcgt gtctgacaaa ttcttcatac acacatttcc cctttgcaca tcagtctgt      60
ataggttatt tctataggag aaaaaaaata ttcaaattcc ttgtgcactg gtaacaggca    120
tgaaggctca gcaaagccaa tacgtgttat gtccagttgg agacagtgcc agggccaaca    180
ttccagactt ctcagataga agtgcgcct gcctgccctg ctctgagaat tgaagagag      240
tagttcagtt agaattaaga ggcagtagag aaaagtcttg ggaaatctgg ttagagatat    300
aaatatgaga actggacatg gtggtacaca cctgtgatct ctgtgtttag ggagggaggg    360
cagagagatc aggagttcaa ggccagcctg agctacttga gacccagtct aaataaataa    420
gagatagatt acagagtgcc tttaactagt acagagaaag aatttgggtt tatctgtgtc    480
agttacgctg aaataatttt taagtaataa aatccctttt aataagaaac cttatgaggt    540
cagtatgcac aatgaactta agagagaccc cagctcctg agctgagtga tggggaagga    600
cagccactgc ctgtgatgtg tgagtgacgt gcttccaagt gttttaacca ctgacgatta    660
catagcctgc acagtcagga gaaacagcc gtattctctg ccagttctct tccctttac     720
```

-continued

```
aaacagatga gagacacaca cagagaatcc atttaaagag cggacctttg t tctgattag    780 gggcaatttt aagtacttaa gagttcacac aaagtctagc cttcaaaaag a aaacaggtt    840 cccaaactag ggaggaaaca gaatcatttc cattttggtg acatttagtg g gaagaagct    900 cacagacatt tagacgttcc aactctttcc ccactagtgg accaagtata t aatatggta    960 tcttttgggc actggtatta caactgtttt ttaaacaaaa gactttcctt g tgctttact   1020 aaaaacccag acggtgaatc ttgaatacaa tgcgtggcac ccacggcagg c attctattg   1080 tgcatagttt tgactgacag gagatgacag catttggctg gctgcgcttg c tgaggaccc   1140 tctcctcctg tgtggcgtct gagactgtga tgcaaatgcg cccgcccttt t ctgggaact   1200 cagaacgcct gagtcaggcg gcggtggcta ttaaagcgcc tggtcaggct g ggctgccgc   1260 actgcaagga tgaggcttcc tggttggttg tggctgagtt ctgccgtcct c gctgcctgc   1320 cgagcggtgg aggagcacaa cctgactgag gggctggaga tgccagcgc c caggctgcc   1380 tgccccgcga ggctggaggg cagcgggagg tgcgagggga gccagtgccc c ttccagctc   1440 accctgccca cgctgaccat ccagctcccg cggcagcttg cagcatgga g gaggtgctc   1500 aaagaagtgc ggaccctcaa ggaagcagtg gacagtctga gaaatcctg c caggactgt   1560 aagttgcagg ctgacgacca tcgagatccc ggcgggaatg gagggaatgg a gcagagaca   1620 gccgaggaca gtagagtcca ggaactggag agtcaggtga acaagctgtc c tcagagctg   1680 aagaatgcaa aggaccagat ccaggggctg caggggcgcc tggagacgct c catctggta   1740 aatatgaaca acattgagaa ctacgtggac aacaaagtgg caaatctaac c gttgtggtc   1800 aacagtttgg atggcaagtg ttccaagtgt cccagccaag aacacatgca g tcacagccg   1860 ggtaggtgta atgagggtca tacagtttgt tcatgaaagc tgtatagcca g atagtggcc   1920 ataaacatta acccgaggga gcataagtta gtcagacttt cacctgttaa g ttatggcag   1980 gagaaacaag tgttttctca atgagacaaa cagaaatggt aaatgatcca c gtacaaaaa   2040 tcctattagt tgtactcgtt agagaccgtc acttgcaagt ctctagacct t ccctgctag   2100 gtcgaccaac agacgagcag aaacagattc ctcccggaat ctgaacacat a tttgaacac   2160 aggacaggta tggcaaggtt cctggctctg cttgcttagg tccctgggaa t cagatcttg   2220 ggtggctgat gggctttata aggctttcac aaacaatctg ctgtgctagg t tctcaaata   2280 tctagtgaga atgggagatt tttatacatg gaagcatctc tcctctctct c tcctctctc   2340 ctctctcttc tctctctctc tctctctctc tctctctctc tctctctctc t ctctctctc   2400 ctccctccct ccctctctct ctctttgtgt gcgtgtgtgg tggggatgag g acacgtgta   2460 gaacttcggg ggttgagact tagtgcatat gcatcctcac cattccagtt a gtgaatgtt   2520 aacactattt aaggtcacag acctaacagc cttctgtgtc cggattcctg g attcctagg   2580 acctttgtgg atgggttgcc acaccctctg tgttcatcct gactgtgagg t cgatgggac   2640 atagtaggga taactttcat ttggaatctc tagagatggt aggtcatcat g tcatagaat   2700 gttatcacta atgaccaaga tagacactca tgtttaagag acatcacaag g tgtatatta   2760 aatatgacat ggcatataac ttgtaatgac acaaaaatat tctgttacct a cttttctcc   2820 taaaagcttg ggactctcca gagttctaaa tacatgcaaa cagattattg t gttttacag   2880 gaatcttata ttgaactttc tttacctgac tcaaatttta ttaaaattaa c tgggaacaa   2940 atagttggtc tctaatctct acaaaaacca ccaaatgatt acactgagca t aattataat   3000 caccctgctg ctacgtctag aaaccaaact gtgaaatatt ggctgactgt a taccttcct   3060
```

```
aaataataaa ttcaggataa cattgccata ttattggaga acccccccct c ccttttaaa    3120
actggaatca ttttatgtca atctcaggtg aaatacgaat gggtttcaga a cagtgctgt    3180
gcactgaagg ctgacattta gaacatatat aacgatttct gtaaagtctg c tgtaacaat    3240
tgctgattgt atcctaggag acttggactc ctctcaacgt taaggcagag g aatataatg    3300
gttatgagag taaaactctc tgtcaggtac atctggcttt ctgtcccagc t ctgtcactt    3360
aacacttagt tgcggtggga aaactccctg atcttccggg agactaagta a ctgtataag    3420
caagctggcc gtgatatcca cgtcgtaagg ctgctgtgtg ggttcagtga a aactgttac    3480
agtgattggc agagtttctg gaggtcattg accctcatta aaccttgcat a cacttattc    3540
ttactactct ttgctgttag tgttgccacc aggattgcca ttcaaggcag t cctgtatac    3600
ttgataacac cagttggttc tgaggcctta gttagcatct gttagcctgg t tcaggagag    3660
tgtatcagag ccaggttcct ctatcacata aactgtaacg caagtgaatt g tccaattgc    3720
tgttgagtct gagagtcctt gaggtgcata gctttgacta ataaatcccc a tgcttttat    3780
gcttttcctt cctccctctt ccagttcaac atctaatata caaagattgt t ccgaccact    3840
acgtgctagg aaggagaagc agtggggcct acagagttac ccctgatcac a gaaacagca    3900
gctttgaggt ctactgtgac atggagacca tgggtggagg ctggacggtg c tgcaggctc    3960
gccttgatgg cagcaccaac ttcaccagag agtggaaaga ctacaaagcc g gctttggaa    4020
accttgaacg agaattttgg ttgggcaacg ataaaattca tcttctgacc a agagtaagg    4080
aaatgatttt gagaatagat cttgaagact ttaatggtct cacactttat g ccttgtatg    4140
atcagtttta tgtggctaat gaatttctca aataccgatt acacatcggt a actacaatg    4200
gcacggcagg ggatgccttg cgtttcagtc gacactacaa ccatgacctg a ggtttttca    4260
caaccccaga cagagacaac gatcggtacc cctctgggaa ctgtgggctc t attacagct    4320
caggctggtg gtttgattca tgtctctctg ccaatttaaa tggcaaatat t accaccaga    4380
aatacaaagg tgtccgtaat gggatttttct ggggcacctg gcctggtata a accaggcac    4440
agccaggtgg ctacaagtcc tccttcaaac aggccaagat gatgattagg c caagaatt    4500
tcaagccata aattgctagt gttcatctct ctgggcactc actatctaag a ggacgatga    4560
attccttcag ccctttacca tatgtctcag tttatattcc tttcctatgg c taaacattt    4620
cctttaaagc tttacagctt ttagaataaa gctgaaaaga tctaaaaaga c tcctatgtt    4680
gctgttatat gaggaatgct tgaaagcact ggaaatattg acaattatac a ttataattg    4740
caaaaccttt cattttttatt agttgaaaag tttcctaata ttttttattat t tttataata    4800
aaaactaaat tattcagcaa gctagattct atatacgcaa gttttatttt c actagggct    4860
aaatatacac atttgagaat ataccagtcc ttccaggtac aactgaaagc c aagaactgt    4920
agtattatct ttcgtctaag aagaacttaa agcatttttag ttctcaagaa g aagggcagg    4980
gatgggattg ggggccaggg acaatatgta tagctaaatg tattcatcta a tgcaaaata    5040
tggcattaaa atacctaaaa atgtggtagc ataatatatg tctcttccct c tccaattga    5100
aaaataatgt taccctgtag actttggttt agtggtaatt cacttactgt t tatagcctg    5160
ttagaccgcg atacaaaagc tgctttatcc tctccctctg ctctctgtgc a caatggttt    5220
gtgatgtaag gtgctagact actgtaaggt ttccttgggg aaaggcatgg t aagggaaaa    5280
cacactggtt tatattttga aagccaatcc taatcccaaa gcaatactgt t gtcgaggag    5340
tcaacgttct aggaagctga cttttctaga acaaatgtat ttattaggat g aatttggga    5400
att                                                                  5403
```

<210> SEQ ID NO 4
<211> LENGTH: 432
<212> TYPE: PRT
<213> ORGANISM: Murine fgl2

<400> SEQUENCE: 4

```
Met Arg Leu Pro Gly Trp Leu Trp Leu Ser Ser Ala Val Leu Ala Ala
 1               5                  10                  15

Cys Arg Ala Val Glu Glu His Asn Leu Thr Glu Gly Leu Glu Asp Ala
                20                  25                  30

Ser Ala Gln Ala Ala Cys Pro Ala Arg Leu Glu Gly Ser Gly Arg Cys
            35                  40                  45

Glu Gly Ser Gln Cys Pro Phe Gln Leu Thr Leu Pro Thr Leu Thr Ile
        50                  55                  60

Gln Leu Pro Arg Gln Leu Gly Ser Met Glu Glu Val Leu Lys Glu Val
 65                  70                  75                  80

Arg Thr Leu Lys Glu Ala Val Asp Ser Leu Lys Lys Ser Cys Gln Asp
                85                  90                  95

Cys Lys Leu Gln Ala Asp Asp His Arg Asp Pro Gly Gly Asn Gly Gly
                100                 105                 110

Asn Gly Ala Glu Thr Ala Glu Asp Ser Arg Val Gln Glu Leu Glu Ser
            115                 120                 125

Gln Val Asn Lys Leu Ser Ser Glu Leu Lys Asn Ala Lys Asp Gln Ile
        130                 135                 140

Gln Gly Leu Gln Gly Arg Leu Glu Thr Leu His Leu Val Asn Met Asn
145                 150                 155                 160

Asn Ile Glu Asn Tyr Val Asp Asn Lys Val Ala Asn Leu Thr Val Val
                165                 170                 175

Val Asn Ser Leu Asp Gly Lys Cys Ser Lys Cys Pro Ser Gln Glu His
            180                 185                 190

Met Gln Ser Gln Pro Val Gln His Leu Ile Tyr Lys Asp Cys Ser Asp
        195                 200                 205

His Tyr Val Leu Gly Arg Arg Ser Ser Gly Ala Tyr Arg Val Thr Pro
    210                 215                 220

Asp His Arg Asn Ser Ser Phe Glu Val Tyr Cys Asp Met Glu Thr Met
225                 230                 235                 240

Gly Gly Gly Trp Thr Val Leu Gln Ala Arg Leu Asp Gly Ser Thr Asn
                245                 250                 255

Phe Thr Arg Glu Trp Lys Asp Tyr Lys Ala Gly Phe Gly Asn Leu Glu
            260                 265                 270

Arg Glu Phe Trp Leu Gly Asn Asp Lys Ile His Leu Leu Thr Lys Ser
        275                 280                 285

Lys Glu Met Ile Leu Arg Ile Asp Leu Glu Asp Phe Asn Gly Leu Thr
    290                 295                 300

Leu Tyr Ala Leu Tyr Asp Gln Phe Tyr Val Ala Asn Glu Phe Leu Lys
305                 310                 315                 320

Tyr Arg Leu His Ile Gly Asn Tyr Asn Gly Thr Ala Gly Asp Ala Leu
                325                 330                 335

Arg Phe Ser Arg His Tyr Asn His Asp Leu Arg Phe Phe Thr Thr Pro
            340                 345                 350

Asp Arg Asp Asn Asp Arg Tyr Pro Ser Gly Asn Cys Gly Leu Tyr Tyr
        355                 360                 365

Ser Ser Gly Trp Trp Phe Asp Ser Cys Leu Ser Ala Asn Leu Asn Gly
```

-continued

```
    370                 375                 380

Lys Tyr Tyr His Gln Lys Tyr Lys Gly Val A rg Asn Gly Ile Phe Trp
385                 390                 395                 400

Gly Thr Trp Pro Gly Ile Asn Gln Ala Gln P ro Gly Gly Tyr Lys Ser
              405                 410                 415

Ser Phe Lys Gln Ala Lys Met Met Ile Arg P ro Lys Asn Phe Lys Pro
            420                 425                 430

<210> SEQ ID NO 5
<211> LENGTH: 592
<212> TYPE: DNA
<213> ORGANISM: Murine

<400> SEQUENCE: 5
atgaggcttc ctggttggtt gtggctgagt tctgccgtcc tcgctgcctg c cgagcggtg     60
gaggagcaca acctgactga ggggctggag gatgccagcg cccaggctgc c tgccccgcg    120
aggctggagg gcagcgggag gtgcgagggg agccagtgcc ccttccagct c accctgccc    180
acgctgacca tccagctccc gcggcagctt ggcagcatgg aggaggtgct c aaagaagtg    240
cggaccctca aggaagcagt ggacagtctg aagaaatcct gccaggactg t aagttgcag    300
gctgacgacc atcgagatcc cggcgggaat ggagggaatg gagcagagac a gccgaggac    360
agtagagtcc aggaactgga gagtcaggtg aacaagctgt cctcagagct g aagaatgca    420
aaggaccaga tccaggggct gcaggggcgc ctggagacgc tccatctggt a aatatgaac    480
aacattgaga actacgtgga caacaaagtg gcaaatctaa ccgttgtggt c aacagtttg    540
gatggcaagt gttccaagtg tcccagccaa gaacacatgc agtcacagcc g g            592

<210> SEQ ID NO 6
<211> LENGTH: 613
<212> TYPE: DNA
<213> ORGANISM: Homo sapiens

<400> SEQUENCE: 6
atgaagctgg ctaactggta ctggctgagc tcagctgttc ttgccactta c ggttttttg     60
gttgtggcaa acaatgaaac agaggaaatt aaagatgaaa gagcaaagga t gtctgccca    120
gtgagactag aaagcagagg gaaatgcgaa gaggcagggg agtgccccta c caggtaagc    180
ctgccccct  tgactattca gctcccgaag caattcagca ggatcgagga g gtgttcaaa    240
gaagtccaaa acctcaagga aatcgtaaat agtctaaaga aatcttgcca a gactgcaag    300
ctgcaggctg atgacaacgg agacccaggc agaaacggac tgttgttacc c agtacagga    360
gccccgggag aggttggtga taacagagtt agagaattag agagtgaggt t aacaagctg    420
tcctctgagc taaagaatgc caaagaggag atcaatgtac ttcatggtcg c ctggagaag    480
ctgaatcttg taaatatgaa caacatagaa aattatgttg acagcaaagt g gcaaatcta    540
acatttgttg tcaatagttt ggatggcaaa tgttcaaagt gtcccagcca a gaacaaata    600
cagtcacgtc cag                                                       613

<210> SEQ ID NO 7
<211> LENGTH: 707
<212> TYPE: DNA
<213> ORGANISM: Murine

<400> SEQUENCE: 7
ttcaacatct aatatacaaa gattgttccg accactacgt gctaggaagg a gaagcagtg     60
```

```
gggcctacag agttacccct gatcacagaa acagcagcct tgaggtctac t gtgacatgg      120 agaccatggg tggaggctgg acggtgctgc aggctcgcct tgatggcagc a ccaacttca     180 ccagagagtg gaaagactac aaagccggct ttggaaacct gaacgagaa t tttggttgg      240 gcaacgataa aattcatctt ctgaccaaga gtaaggaaat gattttgaga a tagatcttg    300 aagactttaa tggtctcaca ctttatgcct tgtatgatca gttttatgtg g ctaatgaat    360 ttctcaaata ccgattacac atcggtaact acaatggcac ggcagggat g ccttgcgtt     420 tcagtcgaca ctacaaccat gacctgaggt ttttcacaac cccagacaga g acaacgatc   480 ggtacccctc tgggaactgt gggctctatt acagctcagg ctggtggttt g attcatgtc   540 tctctgccaa cttaaatggc aaatattacc accagaaata caaggtgtc c gtaatggga     600 ttttctgggg cacctggcct ggtataaacc aggcacagcc aggtggctac a agtcctcct   660 tcaaacaggc caagatgatg attaggccca agaatttcaa gccataa                  707
```

<210> SEQ ID NO 8
<211> LENGTH: 707
<212> TYPE: DNA
<213> ORGANISM: Homo sapiens

<400> SEQUENCE: 8

```
ttcaacatct aatatataaa gattgctctg actactacgc aataggcaaa a gaagcagtg    60 agacctacag agttacacct gatcccaaaa atagtagctt tgaagtttac t gtgacatgg   120 agaccatggg gggaggctgg acagtgctgc aggcacgtct cgatgggagc a ccaacttca   180 ccagaacatg gcaagactac aaagcaggct ttggaaacct cagaagggaa t tttggctgg   240 ggaacgataa aattcatctt ctgaccaaga gtaaggaaat gattctgaga a tagatcttg    300 aagactttaa tggtgtcgaa ctatatgcct tgtatgatca gttttatgtg g ctaatgagt   360 ttctcaaata tcgtttacac gttggtaact ataatggcac agctggagat g cattacgtt    420 tcaacaaaca ttacaaccac gatctgaagt ttttcaccac tccagataaa g acaatgatc   480 gatatccttc tgggaactgt gggctgtact acagttcagg ctggtggttt g atgcatgtc    540 tttctgcaaa cttaaatggc aaatattatc accaaaaata cagaggtgtc c gtaatggga   600 ttttctgggg tacctggcct ggtgtaagtg aggcacaccc tggtggctac a agtcctcct   660 tcaaagaggc taagatgatg atcagaccca agcactttaa gccataa                   707
```

<210> SEQ ID NO 9
<211> LENGTH: 1052
<212> TYPE: DNA
<213> ORGANISM: Homo sapiens
<220> FEATURE:
<221> NAME/KEY: misc_feature
<222> LOCATION: (384)..(384)
<223> OTHER INFORMATION: n is any nucleic ac id
<221> NAME/KEY: misc_feature
<222> LOCATION: (468)..(468)
<223> OTHER INFORMATION: n is any nucleic ac id
<221> NAME/KEY: misc_feature
<222> LOCATION: (470)..(470)
<223> OTHER INFORMATION: n is any nucleic ac id
<221> NAME/KEY: misc_feature
<222> LOCATION: (505)..(505)
<223> OTHER INFORMATION: n is any nucleic ac id
<221> NAME/KEY: misc_feature
<222> LOCATION: (524)..(524)
<223> OTHER INFORMATION: n is any nucleic ac id
<221> NAME/KEY: misc_feature
<222> LOCATION: (668)..(668)
<223> OTHER INFORMATION: n is any nucleic ac id

<400> SEQUENCE: 9

```
atcactctgt tcattcctcc aggtattcgt tatctaatag ggcaattaat t ccttcagca      60
ctttagaata tgccttgttt catattttc atagctaaaa aatgccttgt t tcatatttt     120
tcatagctaa aaaatgatgt ctgacggcta ggttcttatg ctacacagca t ttgaaataa     180
agctgaaaaa caatgcattt taaaggagtc ctttgttgtt atgctgttat c caatgaaca     240
cttgcaagca attagcaata ttgagaatta tacattagat ttacaattct t ttaatttct    300
attgaaactt tttctattgc ttgtattact tgctgtattt aaaaaataat t gttggctgg    360
gtgtggtagc tcacgcctgt aatnccagca ctttggaatg tcaaggcagg c agatcactt    420
gaggtcagga gtttgagacc agcctggcca aacatgtgaa acgctgtntn t attaaaaat    480
acaaaaatta gccgggcatg gtggnacatg cctgtaatcc tagntacttg g gaggctgag    540
gcaggagaat cgcttgaacc tgagaggaag aggttgcagt gagccaagaa t gagccactg    600
cactccagca tgggtgacag agaaaactct gtctcaaaca aaaaaataat a aaatttatt    660
cagtaggntg gattctacac aaagtaatct gtatttgggc catgatttaa g cacatctga    720
aggtatatca ctcttttcag gctataatta tttgggtaat cttcattctg a gacaaactt    780
aatctatatc atttactttg caacagaaca accctacagc attttggttc c cagactaag    840
ggaactaata tctatataat taaacttgtt catttatcat tcatgaaata t aaaatactt    900
gtcatttaaa ccgtttaaaa atgtggtagc ataatgtcac cccaaaaagc a ttcagaaag    960
caatgtaact gtgaagacca gggttaaag gtaattcatt tatagtttat a actccttag   1020
atgtttgatg ttgaaaactg ctttaacatg aa                                  1052
```

<210> SEQ ID NO 10
<211> LENGTH: 1339
<212> TYPE: DNA
<213> ORGANISM: Murine

<400> SEQUENCE: 10

```
tcggtttgga tatcatggga tggaatgaga agggaaagta ggagcccgag a gtgcggtaa      60
gacaaggcat aaggcgtgtc tgacaaattc ttcatacaca catttcccct t tgcacattc    120
agtctgtata ggttatttct ataggagaaa aaaatattc aaattccttg t gcactggta    180
acaggcatga aggctcagca aagccaatac gtgttatgtc cagttggaga c agtgccagg    240
gccaacattc cagacttctc agatagaaag tcgcctgcc tgccctgctc t gagaatttg    300
aagagagtag ttcagttaga attaagaggc agtagagaaa agtcttggga a atctggtta    360
gagatataaa tatgagaact ggacatggtg gtacacacct gtgatctctg t gtttaggag    420
ggagaggcag agatcagg agttcaaggc cagcctgagc tacttgagac c cagtctaaa    480
taaataagag atagattaca gagtgccttt aactagtaca gagaaagaat t tgggtttat    540
ctgtgtcagt tacgctgaaa taatttttaa gtaataaaat cccttttaat a agaaacctt    600
atgaggtcag tatgcacaat gaacttaaga gagaccccca gctcctgagc t gagtgatgg    660
ggaaggacag ccactgcctg tgatgtgtga gtgacgtgct tccaagtgtt t taaccactg    720
acgattacat agcctgcaca gtcaggagaa aacagccgta ttctctgcca g ttctcttcc    780
cttttacaaa cagatgagag acacacacag agaatccatt taaagagcgg a cctttgttc    840
tgattagggg caattttaag tacttaagag ttcacacaaa gtctagcctt c aaaaagaaa    900
acaggttccc aaactaggga ggaaacagaa tcatttccat tttggtgaca t ttagtggga    960
agaagctcac agacatttag acgttccaac tctttcccca ctagtggacc a agtatataa   1020
```

-continued

| | |
|---|---|
| tatggtatct tttgggcact ggtattacaa ctgtttttta aacaaaagac t ttccttgtg | 1080 |
| ctttactaaa aacccagacg gtgaatcttg aatacaatgc gtggcaccca c ggcaggcat | 1140 |
| tctattgtgc atagttttga ctgacaggag atgacagcat ttggctggct g cgcttgctg | 1200 |
| aggaccctct cctcctgtgt ggcgtctgag actgtgatgc aaatgcgccc g ccctttttct | 1260 |
| gggaactcag aacgcctgag tcaggcggcg gtggctatta agcgcctgg t caggctggg | 1320 |
| ctgccgcact gcaaggatg | 1339 |

<210> SEQ ID NO 11
<211> LENGTH: 1338
<212> TYPE: DNA
<213> ORGANISM: Homo sapiens

<400> SEQUENCE: 11

| | |
|---|---|
| tagggttgga agccaggtct cctgagtatg cgagaataaa tacagtcatg g aagtgtaaa | 60 |
| gagtctgcca acattttgag aatgtgaata ggatttggct aaaattaagg g gatatacag | 120 |
| aaaagtcata ggaaatcagg ttaaagacat aaatatgaga taggctacag a gtgttttaa | 180 |
| gtaatacaat aaaacattta gattttttgcc catgtcagtc attttgaaat t attttttaaa | 240 |
| gcaaaaaaac ccttttttaaa caagaaatct tatgagatgt caatatgcaa a acaaattaa | 300 |
| aaggaggtgg tttctctaac tgaagctgtt cctctttcct gccttcagcc t ctgaagaga | 360 |
| aagttagaaa actattatca ttaatgctac atgttttgaa caagctgata t accaagtgg | 420 |
| cccagagagc aggtagaaga accagcgtgg agacagaaag caagaggccc g cctgccagg | 480 |
| gctacctgca gaaagaaagg gcaaagatgc tgtaggcaag agaagttcag g acagacact | 540 |
| ggcatagctc aaagattcac atttgagcag ctgtggaaga tgacagtaca a taccaaaat | 600 |
| gtcgaagggc aaaggaggca gctactggtt ttgatgaaag acaattatgt c cttttaaat | 660 |
| gggtcttaga catttagaca tttatataca ctatgctacg gacaaaggaa t agaaagtag | 720 |
| cactttttttc tccactagtt ttcttctctt tttcaagtag atgaagcaaa a gtcaactgc | 780 |
| aatagtcaga aagctgtact tgttacact tagaaacttc taaaagtgct t aagatttca | 840 |
| cctgaaagtc caacatgaag aaaatacagg ctccccaatg ccccattcta a gaagaaaaa | 900 |
| ggaccatttt catttttagta acgtttctgt tctatagaca gtttggataa c tagctctta | 960 |
| cttttttatct ttaaaaactg ttttttccagt gaagttacgt ataattattt a cttcaagcg | 1020 |
| tagtatacca aattacttta gaaatgcaag acttttctta tacttcataa a atacattat | 1080 |
| gaaagtgaat cttgttggct gtgtacattt gactataata atttcaatgc a tattatttc | 1140 |
| tattgagagt aagttacagt ttttggcaaa ctgcgtttga tgagggctat c tcctcttcc | 1200 |
| tgtgcgtttc taaaacttgt gatgcaaacg ctcccaccct ttcctgggaa c acagaaagc | 1260 |
| ctgactcagg ccatggccgc tattaaagca gctccagccc tgcgcactcc c tgctgggtg | 1320 |
| agcagcactg taaagatg | 1338 |

<210> SEQ ID NO 12
<211> LENGTH: 1339
<212> TYPE: DNA
<213> ORGANISM: Homo sapiens

<400> SEQUENCE: 12

| | |
|---|---|
| tagggttgga agccaggtct cctgagtatg cgagaataaa tacagtcatg g aagtgtaaa | 60 |
| gagtctgcca acattttgag aatgtgaata ggatttggct aaaattaagg g gatatacag | 120 |

```
aaaagtcata ggaaatcagg ttaaagacat aaatatgaga taggctacag a gtgttttaa      180 gtaatacaat aaaacattta gattttttgcc catgtcagtc attttgaaat t attttttaaa   240 gcaaaaaaac ccttttttaaa caagaaatct tatgagatgt caatatgcaa a acaaattaa    300 aaggaggtgg tttctctaac tgaagctgtt cctctttcct gccttcagcc t ctgaagaga    360 aagttagaaa actattatca ttaatgctac atgttttgaa caagctgata t accaagtgg    420 cccagagagc aggtagaaga accagcgtgg agacagaaag caagaggccc g cctgccagg    480 gctacctgca gaaagaaagg gcaaagatgc tgtaggcaag agaagttcag g acagacact    540 ggcatagctc aaagattcac atttgagcag ctgtggaaga tgacagtaca a ttaccaaaa    600 tgtcgaaggg caaggaggc agctactggt tttgatgaaa gacaattatg t ccttttaaa    660 tgggtcttag acatttagac atttatatac actatgctac ggacaaagga a tagaaagta    720 gcactttttt ctccactagt tttcttctct ttttcaagta gatgaagcaa a agtcaactg    780 ccaatagtca gaaagctgta ctttgttaca cttagaaact tctaaaagtg c ttaagattt    840 cacctgaaac gccaacatga agaaaataca ggctccccaa tgccccattc t aagaagaaa    900 aaggaccatt ttcattttag taacgtttct gttctataga cagtttggat a actagctct    960 tactttttat ctttaaaaac tgttttttcca gtgaagttac gtataattat t tacttcaag   1020 cgtagtatac caaattactt tagaaatgca agacttttct tatacttcat a aaatacatt   1080 atgaaagtga atcttgttgg ctgtgtacat ttgactataa taatttcaat g catattatt   1140 tctattgaga gtaagttaca gtttttggca aactgcgttt tgatgagggct a tctcctctt   1200 cctgtgcgtt tctaaaactt gtgatgcaaa cgctcccacc ctttcctggg a acacagaaa   1260 cgctactcag gcacgtgccg gtattaaagc agctccagcc ctgcgcactc c ctgctgggt   1320 gagcagcact gtaaagatg                                              1339

<210> SEQ ID NO 13
<211> LENGTH: 328
<212> TYPE: DNA
<213> ORGANISM: Homo sapiens
<220> FEATURE:
<221> NAME/KEY: misc_feature
<222> LOCATION: (265)..(265)
<223> OTHER INFORMATION: n is any nucleic ac id

<400> SEQUENCE: 13
ccaagtatat aatatggtat cttttgggca ctggtattac aactgttttt t aaacaaaag      60 actttccttg tgctttacta aaaacccaga cggtgaatct tgaatacaat g cgtggcacc     120 cacggcaggc attctattgt gcatagtttt gactgacagg agatgacagc a tttggctgc     180 gtgcgcttgc tgaggaccct ctcctcctgt gtggcgtctg agactgtgat g caaatgcgc     240 ccgccctttt ctgggaactc agaangcctg agtcaggcgg cggtggctat t aaagcgcct    300 ggtcaggctg ggctgccgca ctccaagg                                      328

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
caaaagaagc agtgagacct aca                                            23
```

```
<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
ttatctggag tggtgaaaaa ctt                                       23

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
gcaaacaatg aaacagagga aa                                        22

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
attgccctat tagataacga atac                                      24

<210> SEQ ID NO 18
<211> LENGTH: 15
<212> TYPE: PRT
<213> ORGANISM: Homo sapiens

<400> SEQUENCE: 18

Asp Arg Tyr Pro Ser Gly Asn Cys Gly Leu Tyr Tyr Ser Ser Gly
 1               5                  10                  15

<210> SEQ ID NO 19
<211> LENGTH: 7
<212> TYPE: DNA
<213> ORGANISM: Artificial Sequence
<220> FEATURE:
<223> OTHER INFORMATION: AP1 motif
<221> NAME/KEY: misc_feature
<222> LOCATION: (4)..(4)
<223> OTHER INFORMATION: n is G or C

<400> SEQUENCE: 19 tgantca                                                          7

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
gaaatacaaa aaccgcagaa gg                                        22

<210> SEQ ID NO 21
<211> LENGTH: 21
<212> TYPE: DNA
<213> ORGANISM: Artificial Sequence
<220> FEATURE:
```

```
<223> OTHER INFORMATION: Primer

<400> SEQUENCE: 21
tcttgggaaa tctggttaga g                                    21

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
gagctgagtg atggggaagg a                                    21

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
gggcactggt attacaactg t                                    21

<210> SEQ ID NO 24
<211> LENGTH: 21
<212> TYPE: DNA
<213> ORGANISM: Artificial Sequence
<220> FEATURE:
<223> OTHER INFORMATION: Primer

<400> SEQUENCE: 24
ctcctcctgt gtggcgtctg a                                    21

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
ggataaggag ggcagggtga a                                    21

<210> SEQ ID NO 26
<211> LENGTH: 21
<212> TYPE: DNA
<213> ORGANISM: Artificial Sequence
<220> FEATURE:
<223> OTHER INFORMATION: Primer

<400> SEQUENCE: 26
acagttgtaa taccagtgcc c                                    21

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
aacggagacc caggcagaaa c                                    21
```

```
<210> SEQ ID NO 28
<211> LENGTH: 21
<212> TYPE: DNA
<213> ORGANISM: Artificial Sequence
<220> FEATURE:
<223> OTHER INFORMATION: Primer

<400> SEQUENCE: 28
cttcgggagc tgaatagtca a                                              21

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
gacagcaaag tggcaaatct a                                              21

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
ttctggtgaa gttggtgctc c                                              21

<210> SEQ ID NO 31
<211> LENGTH: 23
<212> TYPE: DNA
<213> ORGANISM: Artificial Sequence
<220> FEATURE:
<223> OTHER INFORMATION: Primer

<400> SEQUENCE: 31
caaaagaagc agtgagacct aca                                            23

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32
tgaccaagag taaggaaatg a                                              21

<210> SEQ ID NO 33
<211> LENGTH: 22
<212> TYPE: DNA
<213> ORGANISM: Artificial Sequence
<220> FEATURE:
<223> OTHER INFORMATION: Primer

<400> SEQUENCE: 33
tgactgtatt tgttcttggc tg                                             22

<210> SEQ ID NO 34
<211> LENGTH: 21
<212> TYPE: DNA
<213> ORGANISM: Artificial Sequence
<220> FEATURE:
<223> OTHER INFORMATION: Primer
```

-continued

```
<400> SEQUENCE: 34
ttctgggaac tgtgggctgt a                                              21

<210> SEQ ID NO 35
<211> LENGTH: 19
<212> TYPE: DNA
<213> ORGANISM: Artificial Sequence
<220> FEATURE:
<223> OTHER INFORMATION: Primer

<400> SEQUENCE: 35
ccagcttcat ctttacagt                                                 19

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
aatcactctg ttcattcctc c                                              21

<210> SEQ ID NO 37
<211> LENGTH: 19
<212> TYPE: DNA
<213> ORGANISM: Artificial Sequence
<220> FEATURE:
<223> OTHER INFORMATION: Primer

<400> SEQUENCE: 37
gaaataatat gcattgaaa                                                 19

<210> SEQ ID NO 38
<211> LENGTH: 19
<212> TYPE: DNA
<213> ORGANISM: Artificial Sequence
<220> FEATURE:
<223> OTHER INFORMATION: Primer

<400> SEQUENCE: 38
aacgcacagg aagaggaga                                                 19

<210> SEQ ID NO 39
<211> LENGTH: 19
<212> TYPE: DNA
<213> ORGANISM: Artificial Sequence
<220> FEATURE:
<223> OTHER INFORMATION: Primer

<400> SEQUENCE: 39
ttgacatcct ttgagatat                                                 19

<210> SEQ ID NO 40
<211> LENGTH: 17
<212> TYPE: DNA
<213> ORGANISM: Artificial Sequence
<220> FEATURE:
<223> OTHER INFORMATION: Primer

<400> SEQUENCE: 40
atggggcatt ggggagc                                                   17

<210> SEQ ID NO 41
<211> LENGTH: 19
```

```
<212> TYPE: DNA
<213> ORGANISM: Artificial Sequence
<220> FEATURE:
<223> OTHER INFORMATION: Primer

<400> SEQUENCE: 41
ggctatctcc tcttcctgt                                              19

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
tgagctatgc cagtgtctgt                                             20

<210> SEQ ID NO 43
<211> LENGTH: 19
<212> TYPE: DNA
<213> ORGANISM: Artificial Sequence
<220> FEATURE:
<223> OTHER INFORMATION: Primer

<400> SEQUENCE: 43
caagcgtagt ataccaaat                                              19

<210> SEQ ID NO 44
<211> LENGTH: 18
<212> TYPE: DNA
<213> ORGANISM: Artificial Sequence
<220> FEATURE:
<223> OTHER INFORMATION: Primer

<400> SEQUENCE: 44
aaggcaggaa agaggaac                                               18

<210> SEQ ID NO 45
<211> LENGTH: 21
<212> TYPE: DNA
<213> ORGANISM: Artificial Sequence
<220> FEATURE:
<223> OTHER INFORMATION: Primer

<400> SEQUENCE: 45
gacaaaggaa tagaaagtag c                                           21

<210> SEQ ID NO 46
<211> LENGTH: 19
<212> TYPE: DNA
<213> ORGANISM: Artificial Sequence
<220> FEATURE:
<223> OTHER INFORMATION: Primer

<400> SEQUENCE: 46
cagggcaaaa atctaaatg                                              19

<210> SEQ ID NO 47
<211> LENGTH: 19
<212> TYPE: DNA
<213> ORGANISM: Artificial Sequence
<220> FEATURE:
<223> OTHER INFORMATION: Primer

<400> SEQUENCE: 47
```

-continued gcccagagag caggtagaa                                            19

<210> SEQ ID NO 48
<211> LENGTH: 18
<212> TYPE: DNA
<213> ORGANISM: Artificial Sequence
<220> FEATURE:
<223> OTHER INFORMATION: Primer

<400> SEQUENCE: 48
ccagccaggg ttgaaata                                             18

<210> SEQ ID NO 49
<211> LENGTH: 18
<212> TYPE: DNA
<213> ORGANISM: Artificial Sequence
<220> FEATURE:
<223> OTHER INFORMATION: Primer

<400> SEQUENCE: 49
gccctgtcag tcattttg                                             18

<210> SEQ ID NO 50
<211> LENGTH: 19
<212> TYPE: DNA
<213> ORGANISM: Artificial Sequence
<220> FEATURE:
<223> OTHER INFORMATION: Primer

<400> SEQUENCE: 50
aaaaacctac cagtagtct                                            19

<210> SEQ ID NO 51
<211> LENGTH: 17
<212> TYPE: DNA
<213> ORGANISM: Artificial Sequence
<220> FEATURE:
<223> OTHER INFORMATION: Primer

<400> SEQUENCE: 51
ttggggtgac attatgc                                              17

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
tgagcagcac tgtaaagatg                                           20

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
gtggcttaaa gtgcttgggt                                           20

METHODS OF MODULATING IMMUNE COAGULATION

This application is a continuation of PCT/CA98/00475 filed May 15, 1998, which claims priority to provisional application No. 60/061,684 filed Oct. 10, 1997 and provisional applications No. 60/046,537 filed May 15, 1997.

FIELD OF THE INVENTION

The present invention relates to methods for modulating immune coagulation using novel antibodies and compounds that modulate immune coagulation.

BACKGROUND OF THE INVENTION

Activation of the coagulation pathways is an important part of immune and inflammatory reactions and is associated with bacterial and viral infections (e.g. endotoxin shock, viral hepatitis), glomerulonephritis (GN), cancer, a number of gastrointestinal diseases, allograft and xenograft rejection and spontaneous or stress-triggered fetal loss. Immune coagulation is mediated by a number of coagulants that, when triggered, activate specific ligands resulting in cleavage and activation of coagulation pathways that lead to fibrin deposition. The molecular events leading to expression of immune coagulants involve natural antibodies binding both to antigens on endothelial cells and Fc receptors on macrophages and endothelial cells. An additional mechanism is immune complex-mediated induction of macrophage procoagulants. These events lead to thrombin production which initiates platelet activation and ultimately fibrin deposition.

In 50% of hepatitis patients moderate to severe consumptive coagulopathy, or disseminated intravascular coagulopathy is found associated with fulminant hepatitis. Thrombi formation is observed around necrotic areas (Sinclair et al., 1990 and Lee, W. M., 1993). As a consequence of hepatitis, levels of factors II, V, VII, and X are decreased in the liver, reflecting both consumptive coagulopathy and a decrease in hepatic synthetic function. Also, the levels of thrombin-antithrombin complexes are high and platelet counts are low (Lee, W. M., 1993). These results indicate that the host immune system, including the coagulation pathway, is disrupted as a result of HBV infection. The limited host range of HBV and the difficulty to propagate the virus in tissue culture have hampered the understanding of HBV and hepatitis B.

Mononuclear phagocytes and macrophages are implicated in the pathogenesis of hepatitis specific induction of procoagulant activity because of their role in coagulation; they synthesize some of the essential coagulation factors such as tissue factor and their surfaces serve as sites of fibrin deposition. Factors participating in the coagulation cascade are released as inactive zymogens and upon activation, by preceding activated factors, they are converted to their active form. The factors are predominantly serine proteases (Davie et al., 1991). Factors VIIa, XIIa, XIa, Xa, IXa, thrombin, kallikrein, and plasminogen are categorized under family 1 serine proteases (Davie et al., 1991; Barrett and Rawlings, 1995; Rawlings and Barrett, 1994; Nduwimana et al., 1995). In order to initiate the coagulation cascade the procoagulants need to be expressed. Ruegg and Pytela, 1995 isolated a cDNA encoding a protein that is homologous to a murine fibrinogen-like protein (Koyama et al. 1987). However, they did not determine the function of the protein or realize its use in modulating immune coagulation.

In view of the many diseases associated with the activation of the coagulation pathways, there is a need to identify and characterize procoagulants and to develop methods for modulating immune coagulation that are useful in the prevention, treatment and diagnosis of diseases associated therewith including bacterial and viral infections, glomerulonephritis (GN), cancer, a number of gastrointestinal diseases, allograft and xenograft rejection and spontaneous or stress-triggered fetal loss.

SUMMARY OF THE INVENTION

The present inventor has identified and characterised an immune procoagulant, and the molecular and cellular events leading to its production. Specifically, the mouse and human direct prothrombinase genes (referred to herein as "mFgl2" and "hFgl2" respectively) have been cloned and sequenced. The nucleic acid sequence of the human and mouse Fgl2 is shown in SEQ.ID.NOS.:1 and 3, respectively. The genes encode a transmembrane serine protease which has functional prothrombinase activity. The proteins encoded by the genes have been sequenced in both humans and mice. The protein has a molecular weight of approximately 70 kd. The hfgl2 gene has been mapped to chromosome 7 and the mFgl2 gene to chromosome 5. The inventor has cloned and sequenced the genomic DNA encoding the human prothrombinase. The organization of the genomic DNA encoding hFgl2 is shown schematically in FIG. 1. The nucleic acid sequence of the promoter region, exon 1, exon 2 and the 3' UTR are shown in FIGS. 8, 2, 3 and 4, respectively. The amino acid sequence of the human and mouse Fgl2 protein is shown in FIG. 5 and in SEQ.ID.NOS.:2 and 4, respectively.

The determination by the inventor that Fgl2 is a direct prothrombinase allows the development of diagnostic methods and therapies for conditions involving immune coagulation.

Accordingly, the present invention provides a method of inhibiting immune coagulation comprising inhibiting the activity or expression of Fgl2. The method can be used in vivo to treat a condition which requires a reduction in immune coagulation such as bacterial and viral infections, glomerulonephritis (GN), cancer, a number of gastrointestinal diseases, allograft and xenograft rejection and fetal loss.

In one aspect, the activity of Fgl2 may be inhibited using an antibody that binds to Fgl2. The present inventor has developed a panel of monoclonal and polyclonal antibodies which neutralize Fgl2 and prevent the fibrin deposition associated with endotoxin shock, viral hepatitis, allograft and xenograft rejection. The antibodies were shown to prevent cellular infiltration, fibrin deposition and tissue damage, and lead to enhanced survival. In particular, antibodies against the direct prothrombinase (Fgl2) were found to be extremely useful in preventing diseases known to have associated massive fibrin deposition and coagulative necrosis, including allograft and xenograft rejection as well as fetal loss induced by stress or cytokines.

In one embodiment, the present invention provides a method of preventing or reducing graft rejection comprising administering an effective amount of an antibody to Fgl2 to an animal in need thereof.

In another embodiment, the present invention provides a method of preventing or reducing fetal loss comprising administering an effective amount of antibody to Fgl2 to an animal in need thereof.

Antibodies can be prepared using entire Fgl2 proteins or immunogenic portions thereof Preferably, such portions bind with an affinity of at least about 106 L/mole to an antibody raised against Fgl2 In particular, the present inventor has shown that a peptide comprising amino add residues 300 to 400 is useful in raising antibodies. Accordingly, the present invention contemplates antibodies which (a) immunoreact with peptides comprising the amino acids at approximately positions 300 to 400 in FIG. 5; and (b) neutralize the prothrombinase activity of hFgl2. The invention also relates to hybridoma cell lines that produce the monoclonal antibodies, and inhibitors and activators thereof.

In another aspect, the expression of Fgl2 may be inhibited using antisense molecules that are complimentary to a nucleic acid sequence from the Fgl2 gene. In particular, the nucleic acid sequences for Fgl2 as shown in FIGS. 2 or 3 may be inverted relative to their normal presentation for transcription to produce antisense nucleic acid molecules.

Additional inhibitors of Fgl2 may be identified by testing substances that inhibit the prothrombinase activity of Fgl2. In particular, the invention contemplates a method for assaying for a substance that affects the prothrombinase activity of Fgl2 comprising (a) reacting Fgl2, a substrate which is capable of being cleaved by Fgl2 to produce a product, and a test substance, under conditions which permit cleavage of the substrate to produce the product; (b) assaying for product; and (c) comparing to the product obtained in the absence of the substance to determine the affect of the substance on the prothrombinase activity of the Fgl2 protein.

The nucleic acid molecules encoding Fgl2, Fgl2 proteins, and monoclonal antibodies of the present invention have diagnostic and monitoring applications. In particular they may be used in conventional assays to monitor or diagnose conditions such as bacterial and viral infections (e.g. endotoxin shock, viral hepatitis), allograft rejection, glomerulonephritis, cancer, a number of gastrointestinal diseases and fetal loss.

In one embodiment, the present invention provides a method for diagnosing or monitoring a condition involving increased immune coagulation in an animal comprising detecting a Fgl2 protein or a Fgl2 nucleic add in a biological sample from the animal.

The invention also contemplates compositions comprising, and methods of using (a) the monoclonal antibodies produced by the hybridoma cell lines of the invention; (b) inhibitors and activators of the monoclonal antibodies; (c) antibodies to a Fgl2; (d) antisense nucleic acid molecules to fgl2; and (e) substances identified using the methods of the invention (e.g. inhibitors and activators of the expression of a nucleic acid molecule of the invention; and, inhibitors and activators of the activity of a Fgl2 protein of the invention).

The compositions of the invention may be used in the prevention or treatment of conditions requiring a reduction in procoagulant activity. Therefore, the invention contemplates a composition for treating a condition requiring a reduction in procoagulant activity comprising administering a therapeutically effective amount of one or more inhibitors of Fgl2. The inhibitor may be an antibody specific for a Fgl2; an antisense nucleic acid molecule of the invention, substances identified in accordance with the methods of the invention or a monoclonal antibody produced by a hybridoma cell line of the present invention. Conditions which require reduction in procoagulant activity include bacterial and viral infections (e.g. endotoxin shock, viral hepatitis), allograft and xenograft rejection, glomerulonephritis, cancer, a number of gastrointestinal diseases and fetal loss.

The present invention also contemplates a vaccine for preventing graft rejection comprising an amount of a Fgl2 protein which is effective to provide protection against graft rejection.

The present invention also contemplates a vaccine for preventing fetal loss comprising an amount of a Fgl2 protein which is effective to provide protection against fetal loss.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The invention will be better understood with reference to the drawings in which:

FIG. 2 shows the nucleotide sequence of exon 1 of the mouse (SEQ.ID.NO.: 6) Fgl3 genes;

FIG. 3 shows the nucleotide sequences of exon 2 of the mouse (SEQ.ID.NO.: 7) and human (SEQ.ID.NO.: 8) Fgl2 genes;

FIG. 4 shows the nucleotide sequence of the 3' UTR of hFgl2 (SEQ.ID.NO.: 9);

FIG. 5 shows the amino acid sequences of the mouse (SEQ.ID.NO.: 4) and human (SEQ.ID.NO.: 2) Fgl2 proteins with the serine protease sites boxed;

FIG. 6 is the amino acid sequence of the mouse (SEQ.ID.NO.4) and human (SEQ.ID.NO.2) Fgl2 proteins, with the 5 glycosylation sites underlined;

FIG. 7 shows the predicted secondary structure of the hFgl2 protein (SEQ.ID.NO.2);

FIG. 8A shows the nucleotide sequence of the mouse (SEQ.ID.NO.: 10) and human (SEQ.ID.NO.: 11) Fgl2 gene promoter regions;

FIG. 8B shows the nucleotide sequence of the mouse (SEQ.ID.NO.: 10) and human (SEQ.ID.NO.: 11) Fgl2 gene promoter regions;

FIG. 9A shows the nucleic acid sequence of the transcription binding sites in the putative promoter region of hfgl2 (SEQ.ID.NO.: 12);

FIG. 9B shows the nucleic acid sequence of the transcription binding sites in the putative promoter region of hfgl2 (SEQ.ID.NO.: 12);

FIG. 17 shows the Fgl-2 promoter DNA sequence (SEQ.ID.NO.: 13).

DETAILED DESCRIPTION OF THE INVENTION

Figure 1:
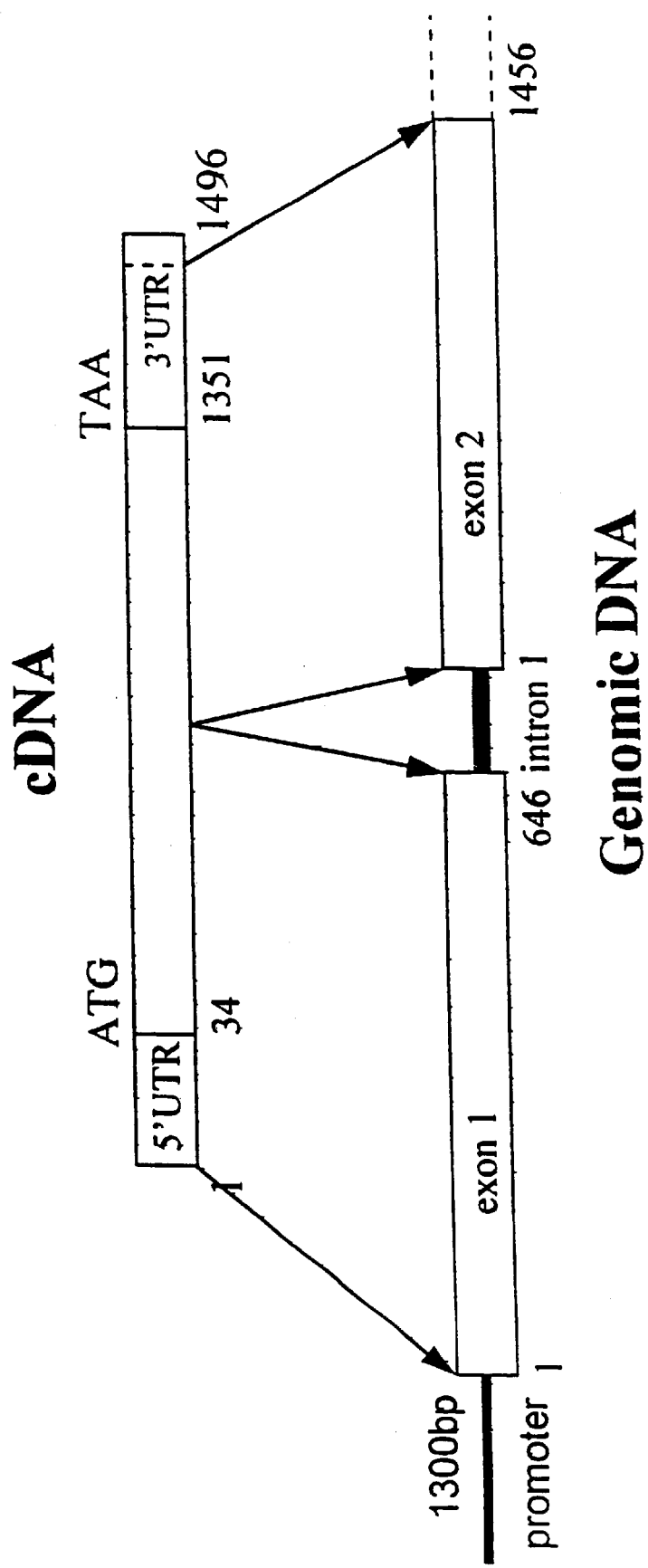
FIG. 1 is a schematic representation of the hfgl2 gene.

The following standard abbreviations for the amino acid residues are used throughout the specification: A, Ala—alanine; C, Cys—cysteine; D, Asp—aspartic acid; E, Glu—glutamic acid; F, Phe—phenylalanine; G, Gly—glycine; H, His—histidine; I, Ile—isoleucine; K, Lys—lysine; L, Leu—leucine; M, Met—methionine; N, Asn—asparagine; P, Pro—proline; Q, Gln—glutamine; R, Arg—arginine; S, Ser—serine; T, Thr—threonine; V, Val—valine; W, Trp—tryptophan; Y, Tyr—tyrosine; and p.Y., P.Tyr—phosphotyrosine.

As hereinbefore mentioned, the inventor has cloned and sequenced the human and mouse genes encoding the protein Fgl2. The inventor has characterised the Fgl2 proteins and has shown that it is a direct prothrombinase. The determination by the is a direct prothrombinase allows the development of therapeutic and diagnostic methods and compositions for conditions involving immune coagulation.

1. THERAPEUTIC APPLICATIONS (A) Methods of Inhibiting Immune Coagulation

In one aspect, the present invention includes methods of inhibiting immune coagulation by inhibiting the activity or expression of Fgl2. Methods that inhibit immune coagulation may be useful in treating conditions which require reduction in procoagulant activity including bacterial and viral infections (e.g. endotoxin shock, viral hepatitis), allograft and xenograft rejection, glomerulonephritis, cancer, a number of gastrointestinal diseases and fetal loss.

Accordingly, the present invention provides a method of preventing or treating a condition requiring a reduction in immune coagulation comprising administering an effective amount of an inhibitor of Fgl2 to an animal in need thereof.

Administration of an "effective amount" of the compounds of the present invention is defined as an amount effective, at dosages and for periods of time necessary to achieve the desired result. The effective amount of a compound of the invention (such as an inhibitor of Fgl2) may vary according to factors such as the disease state, age, sex, and weight of the animal. Dosage regima may be adjusted to provide the optimum therapeutic response. For example, several divided doses may be administered daily or the dose may be proportionally reduced as indicated by the exigencies of the therapeutic situation. The term "animal" as used herein includes all members of the animal kingdom, including humans. Preferably, the animal to be treated is a human.

Inhibitors of Fgl2 include substances that inhibit the transcription and translation of the Fgl2 gene as well as substances that inhibit the prothrombinase activity of the Fgl2 protein.

(i) Antibodies

Examples of substances that can inhibit the prothrombinase activity of the Fgl2 protein are polyclonal and monoclonal antibodies that bind and neutralize Fgl2.

Accordingly, the present invention provides a method of preventing or treating a condition requiring a reduction in immune coagulation comprising administering an effective amount of an antibody to Fgl2 to an animal in need thereof. An effective amount of an antibody means an amount of the antibody that is effective to neutralize or inhibit the prothrombinase activity of the Fgl2 protein.

The inventor has prepared monoclonal antibodies that neutralize the activity of Fgl2. In particular, the inventor has shown that antibodies to Fgl2 can inhibit graft rejection in both allograft and xenograft models. Therefore, the present invention provides a method of preventing or reducing graft rejection comprising administering an effective amount of an antibody to Fgl2 to an animal in need thereof. In one embodiment, the animal is a human and the antibody binds human Fgl2.

The inventor has also shown that antibodies to Fgl2 can prevent or reduce fetal loss resulting from stress or cytokines. Therefore, the present invention also provides a method of preventing or reducing fetal loss comprising administering an effective amount of an antibody to Fgl2 to an animal in need thereof.

The present invention also provides an antibody that binds an epitope of hFgl2 comprising the amino acids at positions 300 to 400 in FIG. 5. In a preferred embodiment, the present invention provides an antibody that binds an epitope of hFgl2 comprising the amino acids at positions 364–378 (DRYPSGNCGLYYSSG) (SEQ.ID.NO.: 18) in FIG. 5.

Antibodies that bind Fgl2 can be prepared using techniques known in the art such as those described by Kohler and Milstein, Nature 256, 495 (1975) and in U.S. Pat. Nos. RE 32,011, 4,902,614, 4,543,439, and 4,411,993 which are incorporated herein by reference. (See also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference).

Within the context of the present invention, antibodies are understood to include monoclonal antibodies, polyclonal antibodies, antibody fragments (e.g., Fab, and F(ab')$_2$) and recombinantly produced binding partners. Antibodies are understood to be reactive against the protein encoded by the nucleic acid molecule of the invention if they bind to Fgl2 with an affinity of greater than or equal to $10^{-6}$ M. As will be appreciated by one of ordinary skill in the art, antibodies may be developed which not only bind to the protein, but which bind to a regulator of the protein, and which also block the biological activity of the protein.

Polyclonal antibodies may be readily generated by one of ordinary skill in the art from a variety of warm-blooded animals such as horses, cows, various fowl, rabbits, mice, or rats. Briefly, a Fgl2 protein of the invention or portions thereof, may be used to immunize an animal. A preferred portion of the protein includes amino acid residues 300 to 400, more preferably 364–378, shown in FIG. 5. An animal may be immunized through intraperitoneal, intramuscular, intraocular, or subcutaneous injections, in conjunction with an adjuvant such as Freund's complete or incomplete adjuvant. Following several booster immunizations, samples of serum are collected and tested for reactivity to the protein. Particularly preferred polyclonal antisera will give a signal on one of these assays that is at least three times greater than background. Once the titer of the animal has reached a plateau in terms of its reactivity to the protein, larger quantities of antisera may be readily obtained either by weekly bleedings, or by exsanguinating the animal.

Monoclonal antibodies may also be readily generated using conventional techniques as described herein. Generally, hybridoma cell lines are prepared by a process involving the Lion under appropriate conditions of an immortalizing cell line and spleen cells from an animal appropriately immunized to produce the desired antibody. Immortalizing cell lines may be murine in origin however, cell lines of other mammalian species may be employed including those of rat, bovine, canine, human origin, and the like. The immortalizing cell lines are most often of tumor origin, particularly myeloma cells but may also include normal cells transformed with, for example, Epstein Barr Virus. Any immortalizing cell may be used to prepare the hybridomas of the present invention.

Antibody producing cells may be employed as fusion partners such as spleen cells or peripheral blood lymphocytes. The animal from which the cells are to be derived may be immunized at intervals with peptides derived from Fgl2. By way of example, animals may be immunized with peptides comprising the amino acids at approximately position 300 to 400 preferably positions 364 to 378 in FIG. 5.

The immortalizing cells and lymphoid cells may be fused to form hybridomas according to standard and well-known techniques employing polyethylene glycol as a fusing agent. Alternatively, fusion may be accomplished by electrofusion.

Hybridomas are screened for appropriate monoclonal antibody secretion by assaying the supernatant or protein purified from the ascites for reactivity using the method described herein. The hybridomas are screened for antibodies which have the desired properties e.g. neutralize the prothrombinase activity of Fgl2.

The monoclonal antibodies produced by the hybridoma cell lines of the invention are also part of the present invention. In accordance with an embodiment of the invention, the monoclonal antibodies immunoreact with peptides comprising the amino acids at positions 300 to 400 preferably 364 to 378 in FIG. 5.

Monoclonal antibodies which immunoreact with peptides comprising the amino acids at positions 300 to 400 in FIG. 5, include homogeneous populations of immunoglobulins. It is understood that immunoglobulins may exist in acidic, basic, or neutral form depending on their amino acid composition and environment, and they may be found in association with other molecules such as saccharides or lipids. The monoclonal antibodies produced by hybridoma cell lines of the invention may be directed against one or more of epitopes of Fgl2. Any characteristic epitope associated with Fgl2 may provide the requisite antigenic determinant It is contemplated that monoclonal antibodies produced by the hybridoma cell lines fall within the scope of the present invention so long as they remain capable of selectively reacting with peptides from Fgl2 preferably the peptides comprising the amino acids at approximately positions 300–400, most preferably 364 to 378 in FIG. 5.

The antigens recognized by the monoclonal antibodies described herein are also a part of the present invention. An antigen recognized by a monoclonal antibody produced by a hybridoma cell line of the invention, may be localized to specific cells and tissues using conventional immunocytochemistry methods. Cryostat sections may be incubated with a monoclonal antibody of the invention and processed by the avidin-biotin-peroxidase technique (ABC Vectastain). This will determine which class of cells express an antigen of Fgl2.

The invention also provides a method for assaying for the presence of an activator or inhibitor of a monoclonal antibody to Fgl2 produced by hybridoma cell lines of the invention comprising mixing macrophages, a known concentration of the monoclonal antibody, and a suspected activator or inhibitor of the monoclonal antibody, and assaying for procoagulant activity. The methods of the invention permit the identification of potential stimulators or inhibitors of procoagulant activity.

The present invention includes recombinant or chimeric antibody molecules. Such antibodies or binding partners may be constructed utilizing recombinant DNA techniques to incorporate the variable regions of a gene which encodes a specifically binding antibody. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources. Primers for mouse and human variable regions including, among others, primers for $V_{Ha}$, $V_{Hb}$, $V_{Hc}$, $V_{Hd}$, $C_{Hl}$, $V_L$ and $C_L$ regions are available from Stratacyte (La Jolla, Calif.). These primers may be utilized to amplify heavy or light chain variable regions, which may then be inserted into vectors such as ImmunoZAP H or ImmunoZAP L (Stratacyte), respectively. These vectors may then be introduced into *E. coli* for expression. Utilizing these techniques, large amounts of a single-chain protein containing a fusion of the VH and VL domains may be produced (See Bird et al., Science 242:423–426, 1988). In addition, such techniques may be utilized to produce a "human" antibody, without altering the binding specificity of the antibody, (ii) Antisense Molecules Antisense oligonucleotides that are complimentary to a nucleic acid sequence from a Fgl2 gene can also be used in the methods of the present invention to inhibit Fgl2 activity.

Accordingly, the present invention provides a method of preventing or treating a condition requiring a reduction in immune coagulation comprising administering an effective amount of an ante oligonucleotide that is complimentary to a nucleic acid sequence from an Fgl2 gene to an animal in need thereof.

The term "antisense oligonucleotide" as used herein means a nucleotide sequence that is complimentary to its target.

In one embodiment of the invention, the present invention provides an antisense oligonucleotide that is complimentary to a nucleic acid molecule having a sequence as shown in FIG. 2 and FIG. 3, wherein T can also be U, or a fragment thereof.

The term "oligonucleotide" refers to an oligomer or polymer of nucleotide or nucleotide monomers consisting of naturally occurring bases, sugars, and intersugar (backbone) linkages. The term also includes modified or substituted oligomers comprising non-naturally occurring monomers or portions thereof, which function similarly. Such modified or substituted oligonucleotides may be preferred over naturally occurring forms because of properties such as enhanced cellular uptake, or increased stability in the presence of nucleases. The term also includes chimeric oligonucleotides which contain two or more chemically distinct regions. For example, chimeric oligonucleotides may contain at least one region of modified nucleotides that confer beneficial properties (e.g. increased nuclease resistance, increased uptake into cells), or two or more oligonucleotides of the invention may be joined to form a chimeric oligonucleotide.

The antisense oligonucleotides of the present invention may be ribonucleic or deoxyribonucleic acids and may contain naturally occurring bases including adenine, guanine, cytosine, thymidine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines; 8-halo guanines, 8-amino guanine, 8-thiol guanine, 8-thiolalkyl guanines, 8hydroxyl guanine and other 8-substituted guanines, other aza and deaza uracils, thymidines, cytosines, adenines, or guanines, 5-trifluoromethyl uracil and 5-trifluoro cytosine.

Other antisense oligonucleotides of the invention may contain modified phosphorous, oxygen heteroatoms in the phosphate backbone, short chain alkyl or cycloalkyl intersugar linkages or short chain heteroatomic or heterocyclic intersugar linkages. For example, the antisense oligonucleotides may contain phosphorothioates, phosphotriesters, methyl phosphonates, and phosphorodithioates. In an embodiment of the invention there are phosphorothioate bonds links between the four to six 3'-terminus bases. In another embodiment phosphorothioate bonds link all the nucleotides.

The antisense oligonucleotides of the invention may also comprise nucleotide analogs that may be better suited as therapeutic or experimental reagents. An example of an oligonucleotide analogue is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogues have been shown to be resistant to degradation by enzymes and to have extended lives in vivo and in vitro. PNAs also bind stronger to a complimentary DNA sequence due to the lack of charge repulsion between the PNA strand and the DNA strand. Other oligonucleotides may contain nucleotides containing polymer backbones, cyclic backbones, or acyclic backbones. For example, the nucleotides may have morpholino backbone structures (U.S. Pat. No. 5,034 506). Oligonucleotides may also contain groups such as reporter groups, a group for improving the pharmacokinetic properties of an oligonucleotide, or a group for improving the pharmacodynamic properties of an antisense oligonucleotide. Antisense oligonucleotides may also have sugar mimetics.

The antisense nucleic acid molecules may be constructed using chemical synthesis and enzymatic ligation reactions using procedures known in the art. The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The antisense oligonucleotides may be introduced into tissues or cells using techniques in the art including vectors (retroviral vectors, adenoviral vectors and DNA virus vectors) or physical techniques such as microinjection. The antisense oligonucleotides may be directly administered in vivo or may be used to transfect cells in vitro which are then administered in vivo. In one embodiment, the antisense oligonucleotide may-be delivered to macrophages and/or endothelial cells in a liposome formulation.

(iii) Other Fgl2 Inhibitors

In addition to antibodies and antisense oligonucleotides, other substances that inhibit Fgl2 may be isolated. Accordingly, the invention also contemplates a method for assaying for a substance that inhibits the prothrombinase activity of a Fgl2 protein of the invention comprising reacting a protein of the invention, a substrate that is capable of being cleaved by the protein to produce a product, and a test substance, under conditions which permit cleavage of the substrate, assaying for product, and comparing to product obtained in the absence of the test substance to determine the affect of the substance on the prothrombinase activity of the protein. Suitable substrates include prothrombin or synthetic substrates such as Chromazym TH (Boehringer Mannheim, Laval, PQ). Conditions which permit the cleavage of the substrate, may be selected having regard to factors such as the nature and amounts of the substance, substrate, and the amount of protein.

The mRNA for hfgl2 has multiple AUUUA repeats in the 3' end and this motif binds a set of RNA binding proteins which render the message stable. Removal of the element decreases mRNA stability. Therefore, the invention also contemplate substances which disrupt the AUUUA and RNA binding protein interactions and thereby destabilize the mRNA. The effect of a test substance on the hfgl2 message may be assayed using conventional methods.

(B) Methods of Inducing Fgl2

In an alternate embodiment, the present invention includes methods of inducing immune coagulation by increasing the activity or expression of Fgl2. Methods that induce immune coagulation may be useful in treating conditions which require an increase in coagulant activity. Such methods can also be used to induce fetal loss.

Accordingly, the present invention provides a method of inducing immune coagulation comprising administering a nucleic acid sequence encoding Fgl2 or an Fgl2 protein to an animal in need thereof.

In one embodiment, the invention provides a method of inducing immune coagulation comprising administering (a) a nucleic acid molecule having a sequence shown in FIG. 2 or 3 or a fragment thereof or (b) a protein having a sequence shown in FIG. 5 or a fragment thereof.

(C) Compositions

The antibodies, antisense oligonucleotides or inhibitors of Fgl2 identified using the methods described herein as well as the Fgl2 protein and nucleic acid sequences, may be incorporated into a pharmaceutical composition containing the substance, alone or together with other active substances.

In one aspect, the present invention provides a composition for use in inhibiting procoagulant activity in an animal comprising (a) an antibody specific for a Fgl2 protein; (b) antisense nucleic acid molecules complimentary to Fgl2; or (c) an inhibitor identified using the method as described above in admixture with a suitable diluent or carrier.

In another aspect, the present invention provides a composition for use in inducing procoagulant activity in an animal comprising a nucleic acid sequence encoding Fgl2 or an Fgl2 protein in admixture with a suitable diluent or carrier.

Such pharmaceutical compositions can be for oral, topical, rectal, parenteral, local, inhalant or subcutaneous, intradermal, intramuscular, intathecal, vaginal, transperitoneal, placental and intracerebral use. They can be in liquid, solid or semisolid form, for example pills, tablets, creams, gelatin capsules, capsules, suppositories, soft gelatin capsules, gels, membranes, tubelets, solutions or suspensions.

The pharmaceutical compositions of the invention can be intended for administration to humans or animals. Dosages to be administered depend on individual needs, on the desired effect and on the chosen route of administration.

The pharmaceutical compositions can be prepared by per se known methods for the preparation of pharmaceutically acceptable compositions which can be administered to patients, and such that an elective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985).

On this basis, the pharmaceutical compositions include, albeit not exclusively, the active compound or substance in association with one or more pharmaceutically acceptable vehicles or diluents, and contained in buffered solutions with a suitable pH and iso-osmotic with the physiological fluids. The pharmaceutical compositions may additionally contain other agents such as adjuvants to enhance immune responsiveness.

The antisense nucleic acid molecules of the invention may be used in gene therapy to inhibit immune procoagulant activity. Recombinant molecules comprising an antisense sequence or oligonucleotide fragment thereof, may be directly introduced into cells or tissues in vivo using delivery vehicles such as retroviral vectors, adenoviral vectors and DNA virus vectors. They may also be introduced into cells in vivo using physical techniques such as microinjection and electroporation or chemical methods such as coprecipitation and incorporation of DNA into liposomes. Recombinant molecules may also be delivered in the form of an aerosol or by lavage. The antisense nucleic acid molecules of the invention may also be applied extracellularly such as by direct injection into cells.

(D) Vaccines

The present invention also contemplates a vaccine against a disease involving immune coagulation comprising an amount of an Fgl2 protein or peptide which is effective to induce an immune response against Fgl2. The term "Fgl2 protein or peptide" includes the full length protein (shown in FIG. 5) and portions of the protein (peptides) that are useful in inducing an immune response. In one embodiment, the vaccine may comprise a peptide having amino acids 300 to 400 shown in FIG. 5, preferably amino adds 364 to 378.

In one embodiment, the present invention provides a vaccine for preventing graft rejection comprising an effective amount of an Fgl2 protein or peptide in admixture with a suitable diluent or carrier. The vaccine may be useful in preventing graft rejection when administered prior to or concurrently with a transplant.

In another embodiment, the present invention provides a vaccine for preventing fetal loss comprising an effective amount of an Fgl2 protein or peptide in admixture with a suitable diluent or carrier.

The vaccine may be a multivalent vaccine and additionally contain immunogens related to other diseases in a prophylactically or therapeutically effective manner.

The vaccine may also comprise an immunologically acceptable carrier such as aqueous diluents, suspending aids, buffers, excipients, and one or more adjuvants known in the art. Examples of adjuvants include the lipid A portion of gram negative bacteria undotoxin, trehalose dimycolate of mycobacteria, the phospholipid lysoleathin, dimethyl dietadecyl ammonium bromide (DDA), linear polyoxypropylene-polyoxyethylene (POP-POE) block polymers and liposomes. The vaccine may also contain cytokines that can enhance the immune response including GM-CSF, IL-2, IL-12, TNF and IFNγ. The vaccine may also contain preservatives such as sodium azide, thimersol, beta propiolactone, and binary ethyleneimine.

The vaccines of the invention can be intended for administration to animals, including mammals, avian species, and fish; preferably humans and various other mammals, including bovines, equines, and swine.

The vaccines of the invention may be administered in a convenient manner, such as intravenously, intramuscularly, subcutaneously, intraperitoneally, intranasally or orally. The dosage will depend on the nature of the disease, on the desired effect and on the chosen route of administration, and other factors known to persons skilled in the art.

A vaccine prepared using the methods described herein may be tested in in vivo animal systems to confirm their efficacy in the prophylaxis or active immunization and treatment of the relevant disease and to determine appropriate dosages and routes of administration.

The present invention also includes the use of the antibodies that bind the fgl2 proteins and portions thereof of the invention as a means of passive immunization.

The present invention also includes DNA immunization with an Fgl2 gene or portion thereof. The Fgl2 gene may have the sequence shown in FIG. 2 or 3 or SEQ.ID.NO.:1 or 3. A portion of an Fgl2 gene preferably includes a nucleic acid molecule encoding a peptide comprising the amino acid residues at positions 300 to 400 in FIG. 5.

IN-VITRO TESTING AND ANIMAL MODELS

The utility of the inhibitors, antibodies, antisense nucleic acid molecules, Fgl2 protein and nucleic acid molecules and compositions of the invention may be confirmed in in vitro system and animal model systems. For example, proliferation, transcription and/or expression of immune coagulants may be determined in one and two way mixed lymphocyte assays carried out in the presence or absence of antibodies. The effect of a substance on procoagulant activity associated with hepatitis may be tested in a murine model of fulminant hepatitis (MacPhee et al., 1985).

Concordant and discordant xenotransplantation transplant models may also be used to confirm the utility of the substances, antibodies, antisense nucleic acid molecules, and compositions of the invention. For example, the following concordant and discordant models may be used:

rodent model—concordant (Lewis rat to Balb/c mouse)
rodent model—discordant (guinea pig to rat) (using vascularized heterotropic heart)
primate model—discordant (guinea pig to rat) (using kidney transplant model).

In concordant and discordant models for testing monoclonal antibodies the following protocol may be used. Recipient animals may receive about 100 μg of purified antibody two days prior to transplant and for 10 to 14 days after. Tissues may be examined for ability of monoclonal antibodies to prevent fibrin disposition, platelet adherence and cellular infiltration. Further testing can be carried out in porcine to primate xenotransplantation using DAF and non-DAF pigs as donors. For these tests animals may be given about 5 mg/kg/animal/day of antibody. For concordant rodent studies animals may receive Neoral (10 mg/kg/i.m.) and/or Cyclophosphamide (40 mg/kg) in addition to the antibody. Control animals will receive an irrelevant antibody of similar isotope. In discordant transplants, in addition to the antibody, some of the animals may receive cobra venom factor and/or Neoral and cyclophosphamide. Pig to primate experiments may be conducted using similar protocols.

The invention also provides methods for examining the function of the Fgl2 protein encoded by the nucleic acid molecule of the invention. Cells, tissues, and non-human animals lacking in expression or partially lacking in expression of the protein may be developed using recombinant molecules of the invention having specific deletion or insertion mutations in the nucleic acid molecule of the invention. A recombinant molecule may be used to inactivate or alter the endogenous gene by homologous recombination, and thereby create a deficient cell, tissue or animal. Such a mutant cell, tissue or animal may be used to define specific cell populations, developmental patterns and in vivo processes, normally dependent on the protein encoded by the nucleic acid molecule of the invention.

To confirm the importance of the fgl2 protein in transplantation, an Fgl2 knockout mouse can be prepared. By way of example, a targeted recombination strategy may be used to inactivate the endogenous fgl2 gene. A gene which introduces stop codons in all reading frames and abolishes the biological activity of the prothrombinase may be inserted into a genomic copy of the fibrinogen like protein. The mutated fragment may be introduced into embryonic stem cells and colonies may be selected for homologous recombination with positive (neomycin)/negative(gancyclovir, thymidine kinase) resistance genes. To establish germ line transmission, two clones carrying the disrupted prothrombinase gene on one allele may be injected into blastocyts of C57/B16 mice and transferred into B6/SJL foster mothers. Chimeras may be mated to C7B1/6 mice and progeny analysed to detect animals homozygous for the mutation (prothombinase −/−). The effects of the mutation on immune response (allo and xeno transplantation, viral hepatitis) in comparison to non-mutated controls may be determined, and the survival and histologic pattern of disease may be analyzed.

(3) DIAGNOSTIC APPLICATIONS

The finding by the present inventor that Fgl2 is a direct prothrombinase involved in immune coagulation allows the detection of conditions involving an increase in Fgl2 prothrombinase.

Accordingly, the present invention provides a method of detecting a condition associated with immune coagulation comprising assaying a sample for (a) a nucleic acid molecule encoding an Fgl2 protein or a fragment thereof or (b) an Fgl2 protein or a fragment thereof.

(i) Nucleic Acid Molecules

The nucleic acid molecules encoding Fgl2 or fragments thereof, allow those skilled in the art to construct nucleotide probes for use in the detection of nucleotide sequences encoding fgl2 or fragments thereof in samples, preferably biological samples such as cells, tissues and bodily fluids. The probes can be useful in detecting the presence of a condition associated with immune coagulation or monitoring the progress of such a condition. Accordingly, the present invention provides a method for detecting a nucleic acid molecules encoding Fgl2 comprising contacting the sample with a nucleotide probe capable of hybridizing with the nucleic acid molecule to form a hybridization product, under conditions which permit the formation of the hybridization product, and assaying for the hybridization product.

Example of probes that may be used in the above method include fragments of the nucleic acid sequences shown in FIGS. 2 and 3 or SEQ.ID.NO.:1 or 3. A nucleotide probe may be labelled with a detectable substance such as a radioactive label which provides for an adequate signal and has sufficient half-life such as 32P, 3H, 14C or the like. Other detectable substances which may be used include antigens that are recognized by a specific labelled antibody, fluorescent compounds, enzymes, antibodies specific for a labelled antigen, and chemiluminescence. An appropriate label may be selected having regard to the rate of hybridization and binding of the probe to the nucleic acid to be detected and the amount of nucleic acid available for hybridization. Labelled probes may be hybridized to nucleic acids on solid supports such as nitrocellulose filters or nylon membranes as generally described in Sambrook et al, 1989, Molecular Cloning, A Laboratory Manual (2nd ed.). The nucleotide probes may be used to detect genes, preferably in human cells, that hybridize to the nucleic acid molecule of the present invention preferably, nucleic acid molecules which hybridize to the nucleic acid molecule of the invention under stringent hybridization conditions as described herein.

Nucleic acid molecules encoding a Fgl2 protein can be selectively amplified in a sample using the polymerase chain reaction (PCR) methods and cDNA or genomic DNA. It is possible to design synthetic oligonucleotide primers from the nucleotide sequence shown in FIGS. 2 and FIG. 3 for use in PCR. A nucleic acid can be amplified from cDNA or genomic DNA using oligonucleotide primers and standard PCR amplification techniques. The amplified nucleic acid can be cloned into an appropriate vector and characterized by DNA sequence analysis. cDNA may be prepared from mRNA, by isolating total cellular mRNA by a variety of techniques, for example, by using the guanidinium-thiocyanate extraction procedure of Chirgwin et al., Biochemistry, 18, 5294–5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.

(ii) Proteins

The Fgl2 protein may be detected in a sample using antibodies that bind to the protein as described in detail above. Accordingly, the present invention provides a method for detecting a Fgl2 protein comprising contacting the sample with an antibody that binds to Fgl2 which is capable of being detected after it becomes bound to the Fgl2 in the sample.

The binding of the antibodies to the Fgl2 protein may be detected using a variety of known techniques including ELISA, radioimununoassay or histochemical tests. Thus, the antibodies may be used to quantify the amount of the protein in a sample in order to determine its role in particular cellular events or pathological states and to diagnose and treat such pathological states.

In particular, the polyclonal and monoclonal antibodies against Fgl2 may be used in immuno-histochemical analyses, for example, at the cellular and sub-subcellular level, to detect a protein of the invention, to localise it to particular cells and tissues, and to specific subcellular locations, and to quantitate the level of expression.

Cytochemical techniques known in the art for localizing antigens using light and electron microscopy may be used to detect a protein of the invention. Generally, an antibody specific for the protein may be labelled with a detectable substance as described herein and the protein may be localised in tissue based upon the presence of the detectable substance.

Indirect methods may also be employed in which the primary antigen-antibody reaction is amplified by the introduction of a second antibody, having specificity for the antibody reactive against the protein encoded by the nucleic acid molecule of the invention.

4. FGL2 GENES AND PROTEINS

As hereinbefore mentioned the present inventor hag cloned and sequenced genomic hFgl2. In this regard, the entire genomic sequence as well as the sequence of the promoter region, shown in FIG. 8 (SEQ.ID.NO.: 11), and the 3' UTR, shown in FIG. 4 (SEQ.ID.NO.: 9), are included within the scope of the invention.

Accordingly, in one embodiment the present invention provides an isolated nucleic acid molecule comprising (a) the sequence shown in FIG. 8 (SEQ.ID.NO.: 11), where T can also be U; (b) nucleic acid sequences which have substantial sequence identity with (a); and (c) a fragment of (a) or (b).

In another embodiment the present invention provides an isolated nucleic acid molecule comprising (a) the sequence shown in FIG. 4 (SEQ.ID.NO.: 9), where T can also be U; (b) nucleic acid sequences which have substantial sequence identity with (a); and (c) a fragment of (a) or (b).

The present invention also includes fragments of the nucleic acid sequences shown in FIG. 2 or 3 or SEQ.ID.NOS.:6 or 8 which have particular utility in the methods and compositions described above. The fragments generally comprise a nucleic acid sequence having at least 15 bases which will hybridize to the sequences shown in FIGS. 2 and 3 or SEQ.ID.NOS.:6 or 8 under stringent hybridization conditions.

Stringent hybridization conditions are those which are stringent enough to provide specificity, reduce the number of mismatches and yet are sufficiently flexible to allow formation of stable hybrids at an acceptable rate, Such conditions are known to those skilled in the art and are described, for example, in Sambrook, et al, (1989, Molecular Cloning, A Laboratory Manual, Cold Spring Harbor). By way of example only, stringent hybridization with short nucleotides may be carried out at 5–10 below the $T_m$ using high concentrations of probe such as 0.01–1.0 pmole/ml.

Fragments of the nucleic acid molecules encoding an immunogenic portion of a human Fgl2 protein are particularly contemplated within the scope of the invention. Preferably, such fragments encode a portion of the human Fgl2 protein which portion binds with an affinity of at least about $10^6$ L/mole to an antibody raised against human Fgl2. The present invention in particular contemplates nucleic acids encoding the amino acids at positions 300 to 400, preferably 364 to 378 in the amino acid sequence shown in FIG. 5.

The invention further includes nucleic acid molecules encoding truncations of the protein encoded by the human fgl2 gene, and analogs and homologs of the protein and truncations thereof, as described herein. It will also be appreciated that variant forms of the nucleic acid molecules of the invention which arise by alternative splicing of an mRNA corresponding to a cDNA of the invention are encompassed by the invention. It is also contemplated that nucleic acid molecules of the invention will be prepared having mutations such as insertion or deletion mutations, e.g. nucleic acid molecules encoding analogs of the human Fgl2 protein.

Further, it will be appreciated that the invention includes nucleic acid molecules comprising nucleic acid sequences having substantial sequence identity with the nucleic acid sequences shown in FIGS. 2 (SEQ.ID.NO.: 6), 4 (SEQ.ID.NO.: 9) and 8 (SEQ.ID.NO.: 11) and fragments thereof having at least 15 bases which will hybridize to these sequences under stringent hybridization conditions. The term "sequences having substantial sequence identity" means those nucleic acid sequences which have slight or inconsequential sequence variations from the sequences disclosed in FIGS. 2 (SEQ.ID.NO.: 6) and 3 (SEQ.ID.NO.: 8), i.e. the sequences function in substantially the same manner to produce substantially the same activity as described herein for Fgl2. The variations may be attributable to local mutations or structural modifications. Nucleic acid sequences having substantial identity include nucleic acid sequences having at least 72%, preferably at least 75–95% identity with the nucleic acid sequences as shown in FIG. 2 (SEQ.ID.NO.: 6) and FIG. 3 (SEQ.ID.NO.: 8).

Isolated and purified nucleic acid molecules encoding a protein having the activity of human Fgl2 as described herein, and having a sequence which differs from the nucleic acid sequence shown in FIG. 2 (SEQ.ID.NO.: 6) and FIG. 3 (SEQ.ID.NO.: 8) due to degeneracy in the genetic code are also within the scope of the invention. Such nucleic acids encode functionally equivalent proteins (e.g., a protein having human Fgl2 prothrombinase activity) but differ in sequence from the sequence of FIG. 2 (SEQ.ID.NO.: 6) and FIG. 3 (SEQ.ID.NO.: 8) due to degeneracy in the genetic code.

DNA sequence polymorphisms within the nucleotide sequence of human Fgl2 may result in silent mutations in the DNA which do not affect the encoded amino acid. However, DNA sequence polymorphisms may lead to changes in the amino acid sequences of human Fgl2 within a population. These variations in one or more nucleotides (up to about 3–4% of the nucleotides) of the nucleic acids encoding proteins having the activity of human Fgl2 may exist among individuals within a population due to natural allelic variation. Such nucleotide variations and resulting amino acid polymorphisms are within the scope of the invention.

The nucleic acid molecules of the invention can be used to isolate an Fgl2 from other species. For example, a labelled nucleic acid probe based on all or part of the nucleic acid sequence shown in FIG. 2 (SEQ.ID.NO.: 6) and 3 (SEQ.ID.NO.: 8) can be prepared, and used to screen an appropriate DNA library (e.g. a cDNA or genomic DNA library). Nucleic acids isolated by screening of a cDNA or genomic DNA library can be sequenced by standard techniques.

RNA can be isolated by cloning a cDNA encoding a human Fgl2 protein into an appropriate vector which allows for transcription of the cDNA to produce an RNA molecule which encodes a protein which exhibits Fgl2 prothrombinase activity. For example, a cDNA can be cloned downstream of a bacteriophage promoter, (e.g. a T7 promoter) in a vector, cDNA can be transcribed in vitro with T7 polymerase, and the resultant RNA can be isolated by standard techniques.

A nucleic acid molecule of the invention including fragments, may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

Determination of whether a particular nucleic acid molecule encodes a protein having the activity of human Fgl2 can be accomplished by expressing the cDNA in an appropriate host cell by standard techniques, and testing the ability of the expressed protein to exhibit prothrombinase activity as described herein. A cDNA having the biological activity of human Fgl2 so isolated can be sequenced by standard techniques, such as dideoxynucleotide chain termination or Maxam-Gilbert chemical sequencing, to determine the nucleic acid sequence and the predicted amino acid sequence of the encoded protein.

The initiation codon and untranslated sequences of human Fgl2 may be determined using currently available computer software designed for the purpose, (e.g. PC/Gene (IntelliGenetics Inc., Calif.). The nucleic acid sequence for a 3' untranslated region of hfgl2 is shown in FIG. 4 (SEQ.ID.NO.: 9). Thedintron-exon structure and the transcription regulatory sequences of the gene encoding human Fgl2 may be identified by using a nucleic acid molecule of the invention encoding human Fgl2 to probe a genomic DNA clone library. Regulatory elements can be identified using conventional techniques. The function of the elements can be confirmed by using them to express a reporter gene such as the bacterial gene lacZ which is operatively linked to the elements. These constructs may be introduced into cultured cells using standard procedures or into non-human transgenic animal models. Such constructs may also be used to identify nuclear proteins interacting with the elements, using techniques known in the art.

In addition to the full length amino acid sequence (FIG. 5), the proteins of the present invention include truncations and analogs, and homologs of the protein and truncations thereof as described herein. A truncated Fgl2 protein or fragment of the human Fgl2 protein is a portion of the full-length Fgl2 amino acid sequence having one or more amino acid residues deleted. The deleted amino acid residue (s) may occur anywhere in the polypeptide, including at either the N-terminal or C-terminal end or internally. Fgl2 fragments typically will have a consecutive sequence of at least 10, 15, 20, 25, 30, or 40 amino acid residues that are identical to t he sequences of the human Fgl2. The truncations or portions of the Fgl2 protein may comprise an antigenic site that is capable of cross-reacting with antibodies raised against the Fgl2 protein whose sequence is shown in FIG. 5 (SEQ.ID.NOS: 2 and 4). Therefore, immunogenic portions or fragments of human Fgl2 proteins are within the scope of the invention (e.g. amino acids 300 to 400 in FIG. 5). Preferably the truncated protein or portion of the protein binds with an affinity of at least about $10^6$ L/mole to an antibody raised against human Fgl2.

At the amino terminal end, the truncated proteins may have an amino group (—-NH2), a hydrophobic group (for example, carbobenzoxyl, dansyl, or T-butyloxycarbonyl), an acetyl group, a 9-fluorenylmethoxy-carbonyl (PMOC) group, or a macromolecule including but not limited to lipid-fatty acid conjugates, polyethylene glycol, or carbohydrates. The truncated proteins may have a carboxyl group, an amido group, a T-butyloxycarbonyl group, or a macromolecule including lipid-fatty acid conjugates, polyethylene glycol, or carbohydrates at the carboxy terminal end.

The proteins of the invention may also include analogs of human Fgl2 as sown in FIG. 5 (SEQ.ID.NOS: 2 and 4) and/or truncations thereof as described herein, containing one or more amino acid substitutions, insertions, and/or deletions. Amino acid substitutions may be of a conserved or non-conserved nature. Conserved amino acid substitutions involve replacing one or more amino acids with amino acids of similar charge, size, and/or hydrophobicity characteristics. When only conserved substitutions are made the resulting analog should be functionally equivalent to human Fgl2 as described herein. Non-conserved substitutions involve replacing one or more amino acids with one or more amino acids which possess dissimilar charge, size, and/or hydrophobicity characteristics.

One or more amino acid insertions may be introduced into the amino acid sequence as shown in FIG. 5 (SEQ.ID.NOS: 2 and 4). Amino acid insertions may consist of single amino acid residues or sequential amino acids ranging from 2 to 15 amino acids in length. For example, amino acid insertions may be used to destroy the prothrombinase activity of the protein.

Deletions may consist of the removal of one or more amino acids, or discrete portions (e.g. amino acids) from the human Fgl2 amino acid sequence as shown in FIG. 5 (SEQ.ID.NOS: 2 and 4). The deleted amino acids may or may not be contiguous. The lower limit length of the resulting analog with a deletion mutation is about 10 amino acids, preferably 100 amino acids.

The proteins of the invention also include homologs of human Fgl2 as shown in FIG. 5 (SEQ.ID.NOS: 2 and 4) and/or truncations thereof as described herein. Such homologs are proteins whose amino acid sequences are comprised of the amino acid sequences of human Fgl2 regions from other species that hybridize under stringent hybridization conditions (see discussion of stringent hybridization conditions herein) with a probe used to obtain human Fgl2 as shown in FIG. 5 (SEQ.ID.NOS: 2 and 4). It is anticipated that a protein comprising an amino acid sequence which is at least 72% preferably 75 to 90% similar, with the amino acid sequence shown in FIG. 5 (SEQ.ID.NOS: 2 and 4) will exhibit prothrombinase activity.

The invention also contemplates isoforms of the human Fgl2 protein of the invention. An isoform contains the same number and kinds of amino acids as the protein of the invention, but the isoform has a different molecular structure. The isoforms contemplated by the present invention are those having the same properties as the protein of the invention as described herein.

The present invention also includes a human Fgl2 protein conjugated with a selected protein, or a selectable marker protein (see below) to produce fusion proteins.

The protein encoded by nucleic acid molecules of the invention, or portion thereof, may be prepared using recombinant DNA methods. Accordingly, the nucleic acid molecules of the present invention or a fragment thereof may be incorporated in a known manner into an appropriate expression vector which ensures good expression of the protein. Possible expression vectors include but are not limited to cosmids, plasmids, or modified viruses, so long as the vector is compatible with the host cell used.

The invention therefore contemplates a recombinant molecule of the invention containing a nucleic acid molecule of the invention, or a fragment thereof, and the necessary elements for the transcription and translation of the inserted sequence. Suitable transcription and translation elements may be derived from a variety of sources, including bacterial, fungal, viral, mammalian, or insect genes. Selection of appropriate transcription and translation elements is dependent on the host cell chosen as discussed below, and may be readily accomplished by one of ordinary skill in the art. Examples of such elements include: a transcriptional promoter and enhancer or RNA polymerase binding sequence, a ribosomal binding sequence, including a translation initiation signal. Additionally, depending on the host cell chosen and the vector employed, other genetic elements, such as an origin of replication, additional DNA restriction sites, enhancers, and sequences conferring inducibility of transcription may be incorporated into the expression vector. It will also be appreciated that the necessary transcription and translation elements may be supplied by the native gene and/or its flanking regions.

The recombinant molecules of the invention may also contain a reporter gene encoding a selectable marker protein which facilitates the selection of host cells transformed or transfected with a recombinant molecule of the invention. Examples of reporter genes are genes encoding a protein such as β-galactosidase (e.g.lac Z), chloramphenicol, acetyltransferase, firefly luciferase, or an immunoglobulin or portion thereof such as the Fc portion of an immunoglobulin preferably IgG. Transcription of the reporter gene is monitored by changes in the concentration of the reporter protein such as β-galactosidase, chloramphenicol acetyltransferase, or firefly luciferase. This makes it possible to visualize and assay for expression of recombinant molecules of the invention and in particular to determine the effect of a mutation on expression and phenotype.

Recombinant molecules can be introduced into host cells via transformation, transfection, infection, electroporation etc. Methods for transforming transfecting, etc. host cells to express foreign DNA are well known in the art (see, e.g., Itakura et al., U.S. Pat. No. 4,704,362; Hinnen et al., PNAS USA 75:1929–1933, 1978; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4,766,075; and Sambrook et al. Molecular Cloning A Laboratory Manual, 2nd edition, Cold Spring Harbor Laboratory Press, 1989, all of which are incorporated herein by reference).

Suitable host cells include a wide variety of prokaryotic and eukaryotic host cells, including bacterial, mammalian, yeast or other fungi, viral, plant, or insect cells.

The protein encoded by the nucleic acid molecule of the invention, or portions thereof, may be expressed in non-human transgenic animals such as, mice, rats, rabbits, sheep and pigs (see Hammer et al. (Nature 315:68–683, 1985), Palmiter et al. (Science 222:809–814, 1983), Brinster et al. (Proc Natl. Acad. Sci USA 82:44384442, 1985), Palmiter and Brinster (Cell. 41:343–345, 1985) and U.S. Pat. No. 4,736,866).

The proteins of the invention, and portions thereof may also be prepared by chemical synthesis using techniques well known in the chemistry of proteins such as solid phase synthesis (Merrifield, 1964, J. Am. Chem. Assoc. 85:2149–2154) or synthesis in homogenous solution (Houbenweyl, 1987, Methods of Organic Chemistry, ed. E. Wansch, Vol. 15 I and II, Thieme, Stuttgart).

The proteins of the invention may be conjugated with other molecules, such as proteins or polypeptides. This may be accomplished, for example, by the synthesis of N-terminal or C-terminal fusion proteins. Thus, fusion proteins may be prepared by fusing, through recombinant techniques, the N-terminal or C-terminal of the protein, and a selected protein with a desired biological function. The resultant fusion proteins contain the protein or a portion thereof fused to the selected protein.

The following non-limiting examples are illustrative of the present invention:

EXAMPLES

Example 1

1. Cloning the Human Prothrombinase Gene (hfgl2)

Methods:

a) Screening the PAC Library and Verifying the Clones

Human genomic DNA from the liver was amplified by Polymerase Chain Reaction using primers specific to the human cDNA sequence obtained from GenBank, that corresponds to exon 2 of mouse fgl2 gene; the sense primer CAA AAG MG CAG TGA GAC CTA CA (SEQ.ID.NO.: 14) (hufpl7) is at position 692, and the antisense primer TTA TCT GGA GTG GTG MA AAC TT (SEQ.ID.NO.: 15) (huflp8) is at position 1133 of the human cDNA. The PAC library, from Genome Systems Inc. (St. Louis, Mo.), was screened using the single amplicon, of about 300 nucleotides in length, that was produced from the above Polymerase Chain Reaction. Three clones, namely 6359, 6360, and 6361 were found positive for this screening. The plasmids containing these three clones were purified using the Qiagen maxiprep DNA purification protocol. The quality of the purified DNA and the presence of the inserts were verified by digesting the plasmid with Not 1 restriction enzyme (Canadian Life, Burlington, Canada), and subjecting the samples to Clamped Homogenous Electric Field (CHEF) gel electrophoresis , at 120 angle, 6 Volts, 1–20 seconds ramp interval, 0.5×TBE, and run time of 18 hours.

b) Preparing Sau 3A Library

The clone 6360 was chosen for the rest of the study because in a dot blot analysis it consistently hybridized to sense primer GCA MC MT GM ACA GAG GM A (SEQ.ID.NO.: 16) (huflp1) at position 100 and anti-sense primer at position ATT GCC CTA TTA GAT MC GM TAC (SEQ.ID.NO.: 17) (huflp2) at position 1400. In order to reduce the DNA into fragments of 5 to 10 kb, which is a convenient size range to work with, the 6360 clone was digested under sub-optimal conditions with the restriction enzyme Sau 3A (Canadian Life, Burlington, Canada). The appropriate digest condition was found by incubating 5 $\mu$g of DNA with 1 $\mu$l of 2$\mu$/$\mu$l, 0.5$\mu$/$\mu$l, and 0.1$\mu$/$\mu$l of Sau 3A for one hour, at 37° C. in a total reaction volume of 20 $\mu$l and observing the size range of the DNA fragments on a CHEF gel; the run conditions are 1 to 10 seconds ramp interval, 4.5 volts, 120 angle, 0.5×TBE, and a run time of 16 hours. The 6360 clone was large scale restriction digested by proportionately increasing the amount of DNA, reaction volume, and the amount of enzyme, that is, 10 $\mu$g, 40 $\mu$l, and 2 $\mu$l respectively. The final products of the restriction digest were subjected to CHEF gel electrophoresis at the above conditions. The DNA band corresponding to 6–9 kb was excised and fragments were extracted using the Gene Clean DNA purification kit (Bio/Can Scientific, Mississauga, Ontario). The fragments were ligated into the alkaline phosphatase (Pharmocia, Uppsala, Sweden) treated BamH1 site of the Bluescript II vector (Stratagene) and transfected into DH10B competent cells by electroporation. This Bluescript II library was screened using the huflp1 and 2 primers. The primers were labeled at the 5 end with gamma P32 by using the enzyme Polynucleatide Kinase (Pharmacia, Uppsala, Sweden); these primers were used to screen the Bluescript library. The clone J14 hybridized to both these primers and was used for the subsequent work.

c) Sequencing

The J14 clone was sequenced by Sanger dideoxy chain termination method (Pharmacia, Uppsala, Sweden) and the appropriate primers. The sequence was read from the autoradiograph using the Helixx sequence reading equipment (Helixx Technologies Inc., Scarborough, Ontario). New primers are designed based on the outcomes of manual sequencing and the published cDNA sequence.

Results and Discussion of Cloning hfgl2:

The organization of the J14 clone is summarized in FIG. 1. The coding region has been extensively analyzed and compared to the mouse gene. In order to gather insight into the functional properties of this gene, the protein sequence was predicted from the genomic sequence and compared to mouse fgl2 (direct prothrombinase) protein and other relevant coagulation proteases.

i) The Transcribed Region:

A reported cDNA sequence starts 35 bases upstream of the translation start site (Ruegg and Pytela, 1995). The first nucleotide of the reported cDNA is considered the putative transcription start site. In eukaryotes the transcription start site (+1) has a weak consensus of pyC−1 A+1 NT/Apypy, where adenine at the third position is the transcription start site (Javahery et. al., 1994). The cytosine at −1 position is more conserved than the adenine at +1 position (Bucher, P., 1990; Bucher and Trifonov, 1986). In the hfgl2 cDNA, the first nucleotide is a cytosine, and the transcription initiation site does not comply to the above consensus. In the coding region there are long stretches of conserved sequences. In an alignment of exon I of fgl2 and hfgl2 there are gaps in the mouse sequence, these gaps correspond to the amino acids that are missing in the mouse protein (FIG. 2). Note that in FIG. 2, the 5 untranslated regions (UTR) of fgl2 and hfgl2 are not included. Most of the mismatches are at the third nucleotide of the codons, because of codon redundancy, these nucleotide difference do not translate to differences at the amino acid level. The second exon, which corresponds to the carboxyl end of the protein, is more conserved than exon 1 (FIG. 3). In FIG. 3, exon 2 is included only until the translation stop site because the mouse and the human fgl2 sequences diverge after the translation stop site. The consensus for the 5 splice junction is A/CAG(−1)G(+1)TAAGT where cleavage occurs between −1 and +1 (Breathnack and Chambon, 1981). This splice site consensus is observed in the human fgl2 gene. The 3 splice site consensus is (py) nNpyAG(−1)G(+1) (Breathnack and Chambon, 1981). In the human gene the 3 end sequence of the intron is conserved but not the exon sequence; hfgl2 has a thymidine instead of a guanosine. Except for an additional guanosine at position 14 of 5 UTR of the genomic DNA, the coding regions of the genomic and the cDNA are identical until the last 39 nucleotides of the cDNA. A primer designed on this region, huflp15, does not hybridize to the 3 PACs. This region is not likely to be exon III because in mouse fgl2 there is no evidence for the presence of intron 2 and also, this region of hfgl2 does not have the consensus for intron splicing (Koyama et al., 1987). FIG. 4 is the incompletely sequenced 3 UTR of hfgl2.

ii) Protein Structure:

The hfgl2 protein is 439 amino acids long. The first 204 amino acids are coded by exon 1. The 205th amino acid, a valine, is coded by both exon 1, one nucleotide, and exon 2, two nucleotides. The rest of the 234 ammo acids are coded by exon 2. The human protein is 7 amino acids longer than the mouse protein; the extra amino acids are coded by exon 1. Comparing the mouse and the human protein sequence, the carboxyl end is more conserved than the amino terminus (FIG. 5). There are five glycosylation sites and every one of them are conserved in the mouse and human proteins (FIG. 6). The amino terminus is the most hydrophobic region of the protein. The region between the alanines in positions 12 and 23 is highly hydrophobic. The amino acids between leucine at position 3 and serine at position 11 are moderately hydrophobic. Because of the short hydrophobic stretch of amino acids, it is uncertain whether hfgl2 is a transmembrane protein or a secreted protein. For the reasons given below, it is more likely to be a type II ectoprotein than a secreted protein. The transmembrane region tends to conform to a helical structure, which is suggested in FIG. 7. Leucine, isoleucine, phenylalanine, and valine are classified as strong B sheet formers, yet in a highly nonpolar environment such as a lipid bilayer, these residues will be forced to assume an alpha helical conformation in order to create a stable, maximally hydrogen bonded structure (Reithmeier and Deber, 1992). Above all, there are no signal peptide cleavage sites; in a signal peptide, cleavage occurs on the carboxyl side of the small aliphatic residues, with the most common cleavage site being alanine (50%), followed by glycine (24%), serine (12%) and cysteine (8%) (Reithmeier and Deber, 1992). It has been proposed that the orientation of membrane proteins is dependent upon differences in the charges of the residues flanking each side of the first hydrophobic segment. Basic residues tend to be found on the cytoplasmic side of the membrane, which is seen in hfgl2 (Reithmeier and Deber, 1992).

Based on the catalytic site, proteases are classified as serine, cysteine, aspartate, or metallo proteases (Nduwimana et al., 1995). In their active form, all essential coagulation factors and their regulators are serine proteases; and they belong to family 1 of the clan SA (Davie et al., 1991). DFP (Diisopropyl Fluoro Phosphate) inhibition assays imply that fgl2, the mouse direct prothrombinase, is a serine protease (Levy et al., 1983). The predicted amino acid sequence also indicates that hfgl2 has a greater potential to be a serine protease instead of a cysteine protease (Tables 1 and 2). In hfgl2 there are no serines that are in the same context as the catalytic serine residues of the serine proteases of the coagulation cascade, GDSGG (Barett and Rawlings, 1995; Rawlings and Barrett, 1994). Both hfgl2 and fgl2 could be clan SE serine protease, as in Table 2 (Rawlings and Barrett, 1994). The fgl2 protein also has some similarity to clan 1 cysteine protease, as on Table 2.

After the cysteine at position 212, the rest of the carboxyl end of the protein consists of a domain homologous to the FREDs (Fibrinogen Related Domain) which is found on a number of different proteins with functional diversity. Some of these proteins are the three chains of fibrinogen, tenacin, ficolin, HFREP-1, etc (Ruegg and Pytela, 1995; Koyama et al., 1987; Doolittle, R. F., 1984).

2. Characterization Of The Promoter Region Method:

The J14 clone contains about 1350 nucleotides upstream of the coding region hfgl2. This entire region was sequenced by Sanger dideoxy chain termination method (Phamacia, Uppsala, Sweden). The sequence was read from the autoradiograph using Helixx sequence reader (Helixx Technologies Inc., Scarborough, Ontario). Table 3 lists the primers used for sequencing this putative promoter region of hfgl2. The sequence was analyzed using the DNASIS for Windows, sequence analysis software (Hitachi Software Engineering America Ltd., San Bruno, Calif.) for putative transcription factor binding sites.

Results and Discussion of Sequence Analysis of hfgl2 Putative Promoter Region:

The promoter region does not have a typical TATA box, TATAAAA, where the adenine in the second and sixth positions, and the thymidine in the third position are more conserved throughout all eukaryotic genes than the rest of the TATA box nucleotides (Bucher, P., 1990; Bucher and Trifonov, 1986). The hfgl2 gene has a TATA like sequence, TATTAAA, about 50 nucleotides upstream of the translation start site (FIGS. 8 and 9); a typical TATA box is 25 to 30 nucleotides upstream of transcription start site (Bucher, P., 1990; Bucher and Trifonov, 1986). As the TATA and its context are identical in mouse and human fgl2, this region is suggested to be of functional importance.

An AP1 site is located about 20 nucleotides from the TATA box (FIGS. 8 and 9). The consensus for AP1 motif is TGASTCA (SEQ.ID.NO.: 19), where S is a guanine or a cytosine. Except for the central S, cytosine in humans and guanine in mouse, the AP1 site is identical in mouse and human direct prothrombinase genes. AP1 is composed of dimers of proteins of the Fos and Jun proto-oncogene families. The Jun family members are DNA binding proteins; they bind to the AP1 site as homodimers or as heterodimers with Fos members. Upon activation, Jun gets dephosphorilated at a site proximal to DNA binding domain and acquires its ability to bind DNA (Curran and Franza, 1988; Woodgett et al., 1995). Furthermore, the transactivating domains of Fos and Jun get phosphorilated and are able to interact with the transcription machinery (Woodgett et al., 1995). In certain genes such as tissue factor gene, the AP-1 is required for both constitutive and induced expression (Mackman et al., 1989; Moll et al., 1995).

Interestingly, hfgl2 has 5 Nuclear Factor IL6, (NF IL6), binding sites. The consensus for this transcription factor binding site is T(T/G)NNGNAA(T/G). This region was first identified in the promoter of the IL6 gene; it is located about 350 nucleotides upstream of the transcription start site and upregulates the transcription of the IL6 gene (Akira et al., 1995). In hfgl2, the first NF IL6 binding site is located about 300 nucleotides from the translation start site. NF IL6 belongs to C/EBP, CAAT Enhancer Binding Protein, family of transcription factors and any of the C/EBPs can bind to the above consensus sequence (Wedel and Ziegler-Heitbrock, 1995). The carboxyl end of these proteins are conserved and contain the DNA binding basic region and dimerizing leucine zipper region. The amino terminus contain the transactivating domain (Wedel and Ziegler-Heitbrock, 1995). C/EBP α is responsible for transcription of adipocyte specific genes and constitutive expression of liver specific genes such as albumin and transferrin. C/EBPb and d play a role in the induction of acute phase response genes of the liver and cytokine genes of macrophages (Akira et al., 1992; Wedel and Ziegler-Heitbrock, 1995; Akira and Kishimoto, 1992). C/EBPb or NF IL6 mRNA level is rapidly induced in the macrophages as a result of cytokine induction. Also, the level of C/EBPa and b seem to be inversely related (Akira et al., 1992; Akira and Kishimoto, 1992). Hence, the ratio of the appropriate C/EBPs may influence the expression of hfgl2. In certain hemophilia B patients mutation is found in the CCAAT box of factor N gene which indicates the importance of this cis element (Peterson et al., 1990).

TCF-1 (T Cell Factor 1) binds to the A/T A/T CAAAG motif. The expression of this transcription factor appears to be completely restricted to the T cell lineage and is confined to the nucleus (Castrop et al., 1995; Verbeek et al., 1995). The DNASIS software package has selected 10 TCF 1 binding sites in the promoter region of hfgl2 gene. The presence of TCF 1 binding motifs could be responsible for the reported constitutive expression of this gene in T cells (Puegg and Pytela, 1995; Koyama et al., 1987).

Members of the ets 1 proto-oncogene family binds to the PEA3 domain, Polyomavirus Enhancer Activator 3, which has a consensus sequence AGGAAG (Oin et al., 1992; Wasylyk et al., 1990). There is a PEA3 site about 1200 bp from the translation start site (FIGS. 8 and 9). There is evidence for the corporative interaction between AP1 and PEA3 (Wasylyk et al., 1990). Some of the promoters with PEA3 motifs can be grouped according to the type of inducers which activate their transcription i) acute phase response ii) gamma interferon and iii) mitogens and oncogenes (Xin et al., 1992). As fgl2 gene expression is induced by viral infection, hfgl2 gene product could also be an acute phase response protein. The presence of many putative bHLH (Basic Helix Loop Helix) domains, with the consensus of CAXXTG, may imply that this gene is under the influence of many, DNA binding transcription activators (Murre et al., 1994). These transcription activator proteins contain a region of mainly basic residues that allows the helix-loop-helix proteins to bind DNA. The second region characterized by mainly hydrophobic residues, the HLH domain, allows these proteins to interact and form either homo or hetero dimers (Murre et al., 1994).

3. Sizing the hfgl2 Intron by PCR

Method:

Intron 1 was amplified by PCR using the primer combinations huflp3 with 6, and huflp 5 with 6 (Table 3). As templates for amplification J14, 6359, 6360, and 6361 clones were used. As mentioned above, 6359, 6360, and 6361 are the PAC clones that contain hfgl2, and J14 is a subclone of 6360 in Bluescript II vector (Strategene). The reactions were performed in a 50 µl total volume containing 25p moles of each primers, 200 βM each dNTP, 1×PCR, 3 or 5 mM MgCl2, and 2.5 U of Taq Polymerase (Canadian Life, Burlington, Canada). The reaction was subjected to denaturing at 95° C. for 5 minutes, followed by 30 cycles of 1 minute denaturing at 95° C., 1 minute annealing at 60° C., and 2 minute extension at 72° C. The PCR products were electrophoresed in 0.8% agarose, 0.5×TBE, and 0.5 ug/ml ethidium bromide.

Results and Discussion of Sizing Hfgl2 Intron:

A 2800 bp amplicon was synthesized when the primer set huflp 3 and 6 was used. When huflp 5 and 6 were used the size of the amplicon was 2400 bp. Subtracting the exonic region, intron 1 is about 2200 bp, which is also observed in mouse (Koyama et al., 1987). As mentioned earlier this intron of human fgl2 has the consensus for intron splicing. The consensus for the 5 splice junction is A/CAG(−1)G(+1)TAAGT where cleavage occurs between −1 and +1 (Breathnach and Chambon, 1981). This splice site consensus is observed in human fgl2 gene. The 3 splice site consensus is (py)nNpyAG(−1)G(+1) (Breathnach and Chambon, 1981). In the human gene the 3 end sequence of the intron is conserved but not the exonic sequence; hfgl2 has a thymidine instead of a guanosine.

4. RT-PCR of hfgl2 from Human Small Intestine Total RNA

Method:

In order to synthesize the first strand cDNA from human small intestine total RNA 4 µg of RNA (Bio/Can Scientific, Mississauga, Canada), 2 µl of Random hexamer at stock concentration of 1 µg/ul (Pharmacia, Uppsala, Sweden), 20 U of RNAse Inhibitor (Pharmacia, Uppsala, Sweden), and DEPC treated water to bring the volume to 12 µl, were added together and incubated at 65° C. for 5 minutes and quickly chilled on ice. Then 1 mM each DNTP (1 µl of 20 mM stock), 10 mM DTT (2 µl of 0.1M DIT), 4 µl of 5×1st strand buffer (Canadian Life, Burlington, Canada), and 200 U MMLV-RTase buffer (Canadian Life, Burlington, Canada) were incubated at 37° C. for 1.5 hours. The reaction mix was heated at 95° C. for 5 minutes and diluted 5 fold with 80 µl of DEPC treated water.

Polymerase Chain Reaction was performed in a 50 µl reaction volume, with 10 µl of the above RT mix, 25 µl of 10 pmol/µl of sense and anti-sense primers, 0.2 mM dNTP, 1×Taq buffer, 3 mM MgCl$_2$, and 5 U of Taq Polymerase (Canadian Life, Burlington, Canada). The primer sets used for the PCR reaction were huflp1 and 2, huflp1 and 6, huflp5 and 2, huflp13 and 26, huflp13 and 28, huflp15 and 26, huflp15 and 28, and huflp11 and 28. The reaction conditions were 95° C. for 5 minutes, and 30 cycles of 95° C. for 1 minute, 47 or 57° C. (depending on the primer set) for 1 minute, and 72° C. for 2 minutes. The PCR products were electrophoresed in 0.8% agarose, 05×TBE, and 05 µg/ml of ethidium bromide.

Results and Discussion of RT-PTR on Human Small Intestine Total RNA.

Ruegg and Pytela had reported the cloning of cDNA, from human small intestine, which is homologous to the gene coding for mouse fibrinogen like protein (Ruegg and Pytela, 1995). The RT-PCR results shows that there is indeed hfgl2 expressed constitutively in human small intestine. The primers huflp26 and 28 are located down stream of primers huflp13 and 15; and all 4 primers are located in the 3 UTR. As the primer combinations huflp13 and 26, and huflp13 and 28 produce amplicons, it shows that the 3 end of the J14 clone is indeed part of an exon. As huflp15 does not synthesize an amplicon with antisense primers, the last 39 nucleotides reported by Ruegg and Pytela must be a cloning artifact.

5. Restriction Mapping the PAC Clones

Methods:

In order to find the appropriate restriction enzymes, the PAC clones 6359, 6360, and 6361 were restriction digested with both frequent and infrequent cutters, namely EcoR1, HindIII, BamHI, BglII, PvuII, KpnI, ScaI, XbaI, HincII, EcoRV, SmaI, PstI, SalI, NcoI, NotI, MluI, Bpu11021, Bgl1, SstI, XhoI, ClaI, SfiI, and SacII. The final mapping was performed with the infrequently cutting restriction enzymes Not1, Sma1, and Sal1, and with the frequently cutting enzymes EcoRI, HindIII, PstI, and PvuII. Because the above PAC clones did not have any internal NotI site, they were digested with SmaI and SalI separately, and along with NotI; this facilitates the process of mapping. In all restriction digestions, about 2 µg of DNA was used in 20 µl volume, with the appropriate restriction enzyme. For the double digests, the DNA was digested overnight with NotI in a 10 µl reaction volume, and on the following day with SalI or SmaI in a 20 µl volume, under appropriate buffer conditions. After digesting with infrequent cutters, the DNA was subjected to CHEF gel electrophoresis. For best results, the run conditions were found to be 120 angle, 6 volts, 1–10 second ramp interval, 2.7 liters of 0.5×TBE buffer, 250 ml of 1% agarose (SeaKemMe), and run time of 22 hours. After digesting the DNA with frequent cutters, the DNA was subjected to regular gel electrophoresis, at 30 volts, for about 50 hours, in 0.5×TBE, and in 0.07% agarose.

Figure 10A:
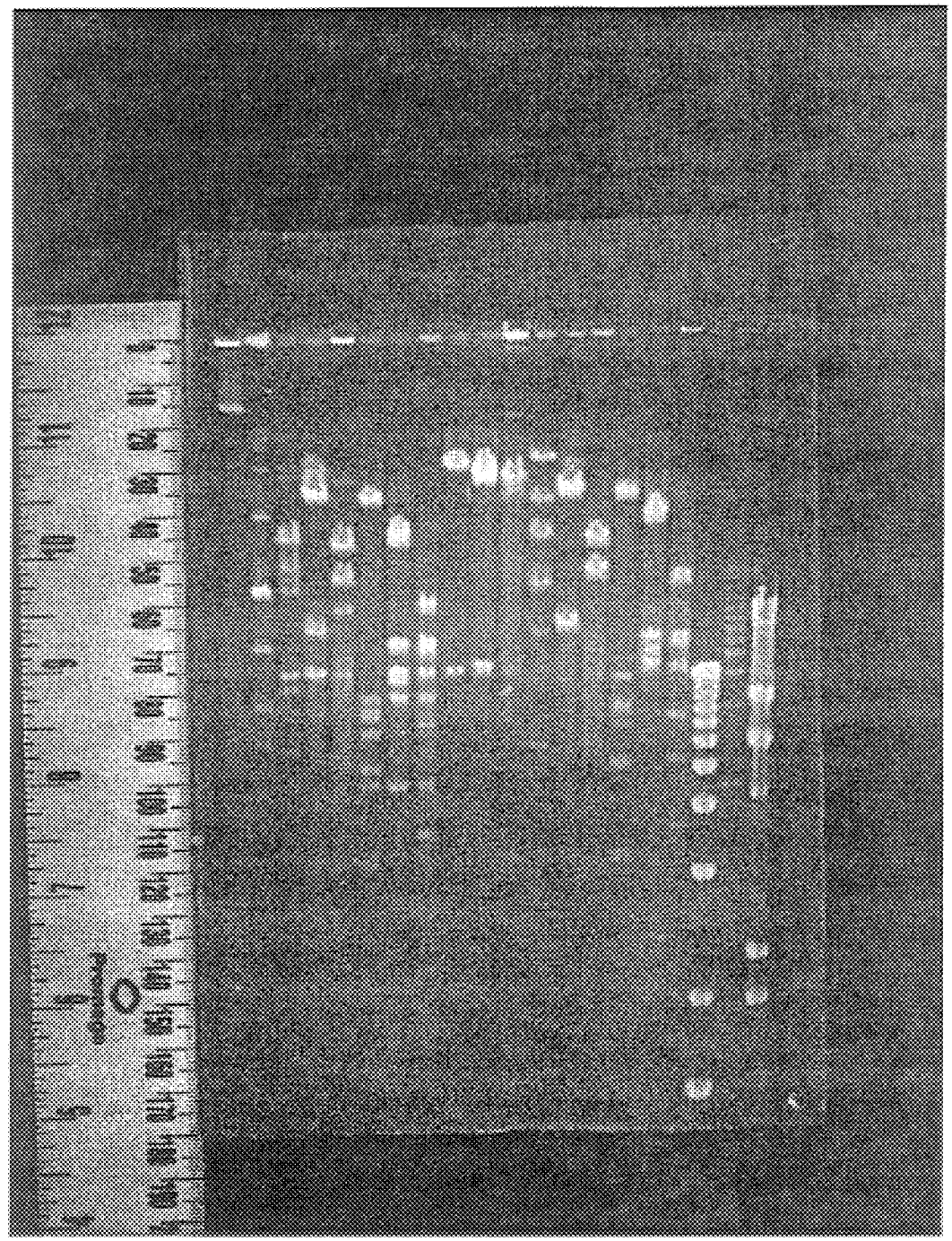
FIG. 10A is a sample of electrophoresis of PAC clones on a CHEF gel.
Figure 10B:
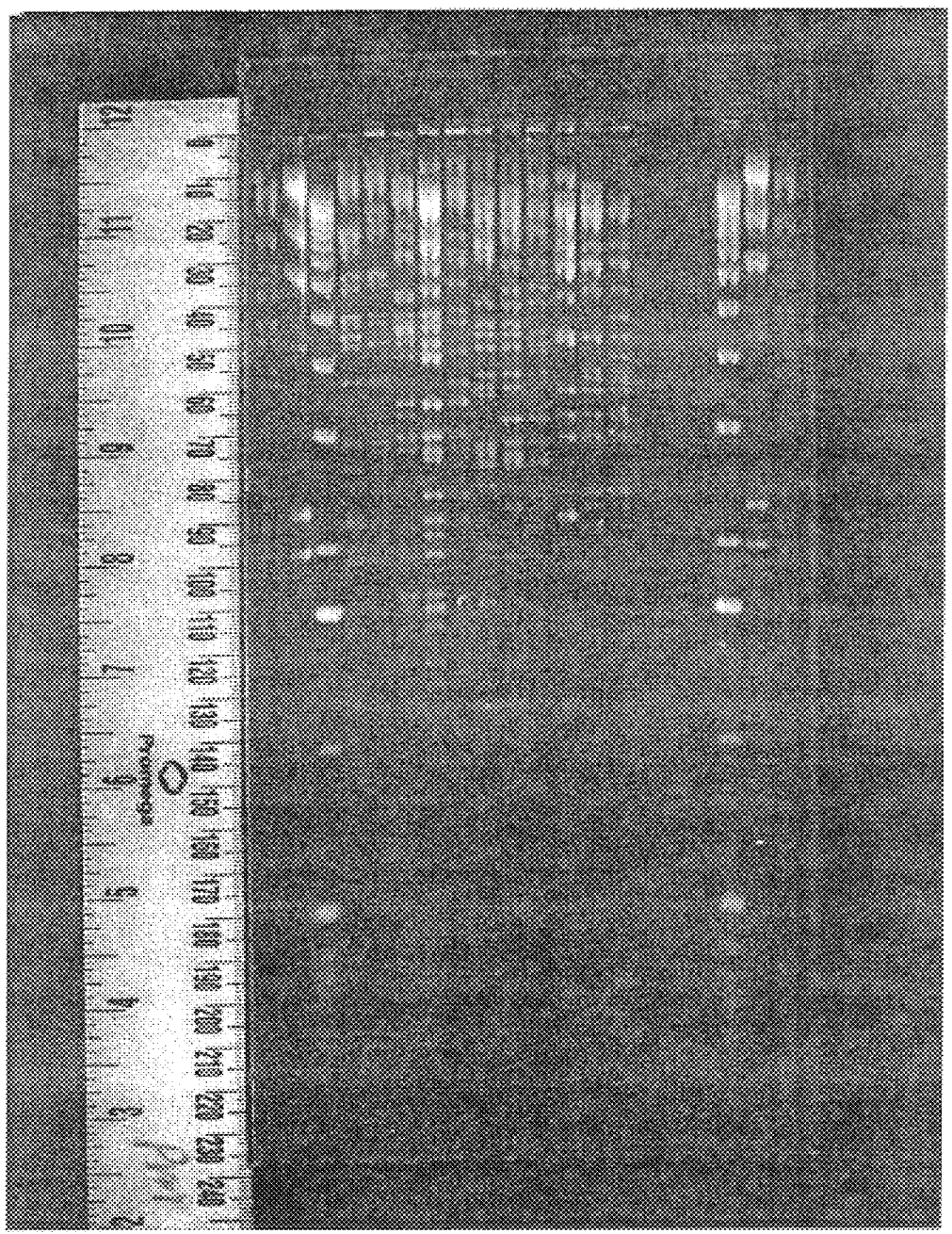
FIG. 10B is a sample of electrophoresis of PAC clones on regular gel.
Figure 11:
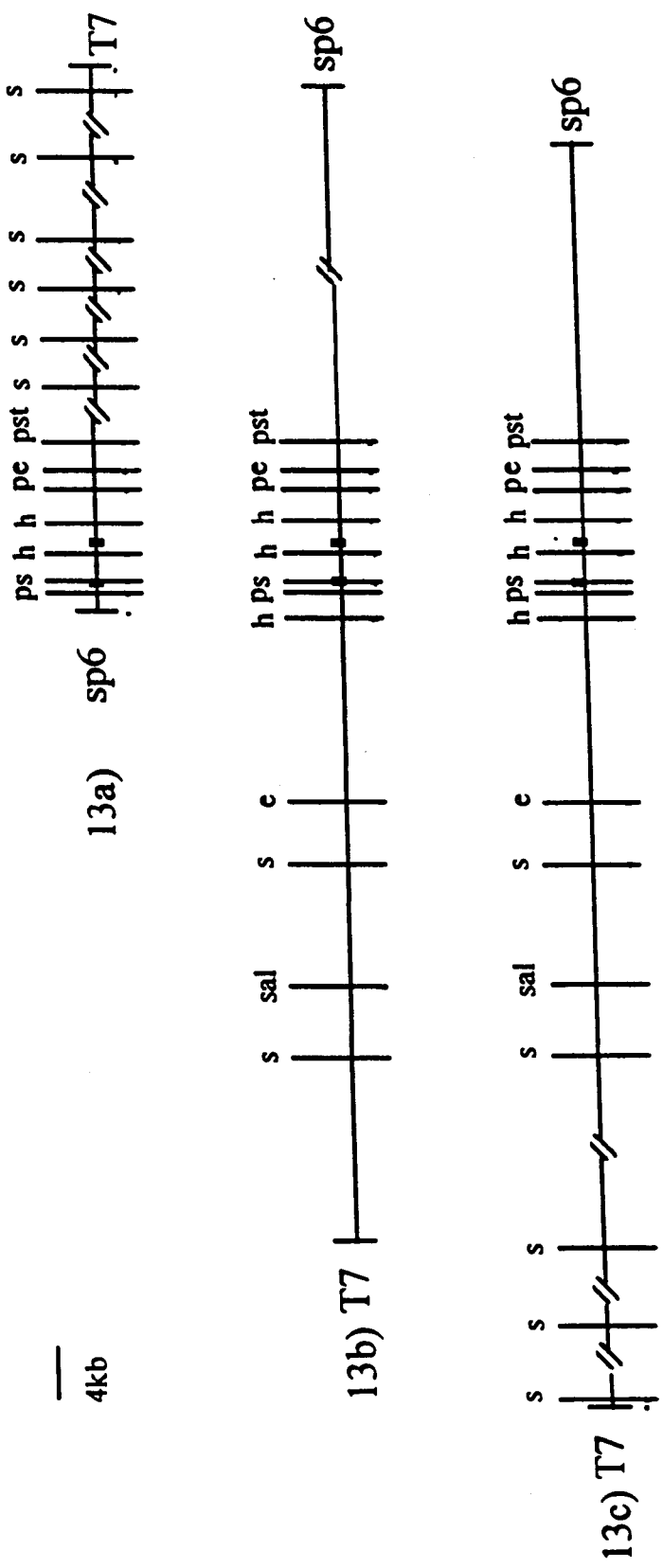
FIG. 11 is a restriction map of three PAC clones.

Results and Discussion of Restriction Mapping:

FIG. 10A is an example of gel electrophoresis of PAC clones on CHEF apparatus, after digesting with infrequent cutters. FIG. 10B is an example of regular gel electrophoresis of PAC clones after cutting with frequent cutters. These clones must have a high C+G content because even the rare cutters digest the clones quite frequently, these enzymes recognize longer sequences that also have a high G+C content. FIG. 11 is a restriction map of the PAC clones. The presence of a SmaI site within the hfgl2 gene hastened the process of mapping hfgl2 within the PAC clones. The approximate sizes of the 3 PAC clones, 6359, 6360, and 6361 are 159 kb, 139 kb, and 116 kb, respectively. The most accurately restriction mapped clone is 6360. The presence of a large number of Sal1 and Sma1 sites has limited the accuracy of mapping the clones 6359 and 6361. FIG. 11 shows that the orientation of the insert in 6359 is opposite to that of 6360 and 6361.

Transient Expression of hfgl2:

The protein sequence homology between fgl2 and hfgl2 suggests that hfgl2 also codes for a direct prothrombinase. A prototype has been developed to synthesize the cDNA for hfgl2 that can be used for expression studies. Human small intestine total RNA (Bio/Can Scientific, Mississauga, Canada) is being used as the template for first strand synthesis and random hexamers (Pharmacia, Uppsala, Sweden) are used as primers. For the PCR reaction huflp29 and 30 are used as primers. The PCR product will be cloned into the vector PCR2.1 (Invitrogen, San Diego, Calif.). The insert will be rescued from the vector using the restriction enzyme EcoR1. This insert, containing the coding region of hfgl2, will be cloned into the EcoR1 site of the vector pcDNA 3.1-(his,myc) (Invitrogen, San Diego, Calif.). In order to increase the transient transfection efficiency, the vector will be linearized and transfected into COS cell, using lipofectin. The cells will be initially screened using the standard procoagulant assay. Then coagulation assays will be performed in factor deficient plasma to see if they carry the potential to exhibit direct prothrombinase activity. Finally, prothrombin cleaving assays will be performed, in presence of anti tissue factor and anti factor X, by monitoring the cleavage of radio active iodine labelled prothrombin.

Northern Blot of Human Small Intestine Total RNA:

25 µg of human small intestine total RNA RNA (Bio/Can Scientific, Mississauga, Canada) is run on an agarose gel, transferred to nylon membrane, and probed with exon 1 of hfgl2 and GABDH, separately. This assay is performed to identify the size of hfgl2 mRNA, and also to detect whether there are more than one species of mRNA for this gene.

Example 2

PREVENTION OF GRAFT REJECTION BY ANTIBODIES TO FGL2

(a) Allograft

In order to study the ability of monoclonal antibodies to rodent fgl2 to prevent allograft rejection, heterotopic auxiliary small intestinal transplants were undertaken using intestines from donor Lewis Brown Norway F1 (LBNF1) and recipient Lewis rats. The procedures followed for the operation have been described previously (Effects of Cyclosporine and Cyclosporine Metabolites in Experimental Small Intestinal Transplantation, P. C. W. Kim, Z. Cohen, P. Y. Wong, E. Cole, J. Cullen, K. Skorecki et. al, Transplantation 1990;49:1043–1050).

Briefly, adult Lewis (LEW) and Lewis x Brown Norway F1 hybrids (LBNF1) female rats weighing 200–250 grams were utilized in all experiments. For 24 hours prior to surgery, animals were starved and donors were gavaged with neomycin 60 mg/kg and erythyromycin 40 gm/kg 24 and 12 hours respectively prior to the operation. Heterotopic auxiliary small intestinal transplantation was carried out in a sterile environment with a modification of the procedure described by Monchik and Russel (Monchik, G. J., Russel, P. Transplantation of Small Bowel in the Rat: Technical and Immunological Considerations, Surgery 1971;70:633).

Rats were divided into 4 groups:

Group I n=5; received no treatment

Group II n=5; received 75 mg/kg of CsA on day 1

Group III received 1 mg/kg of monoclonal antibody to fgl2

Group IV received 1 subcutaneous injection of CsA (7.5 mg/kg) and daily injections of monoclonal antibody to fgl2 (1 mg/kg for 10 days).

The animals were carefully monitored for progress twice daily and at time of demise, tissues (intestine) were removed and sent for routine histology and immunofluorescence for presence of fibrin deposits. At 28 days, surviving animals were sacrificed and allografts analyzed for histology and for presence of fibrin deposits.

Figure 12:
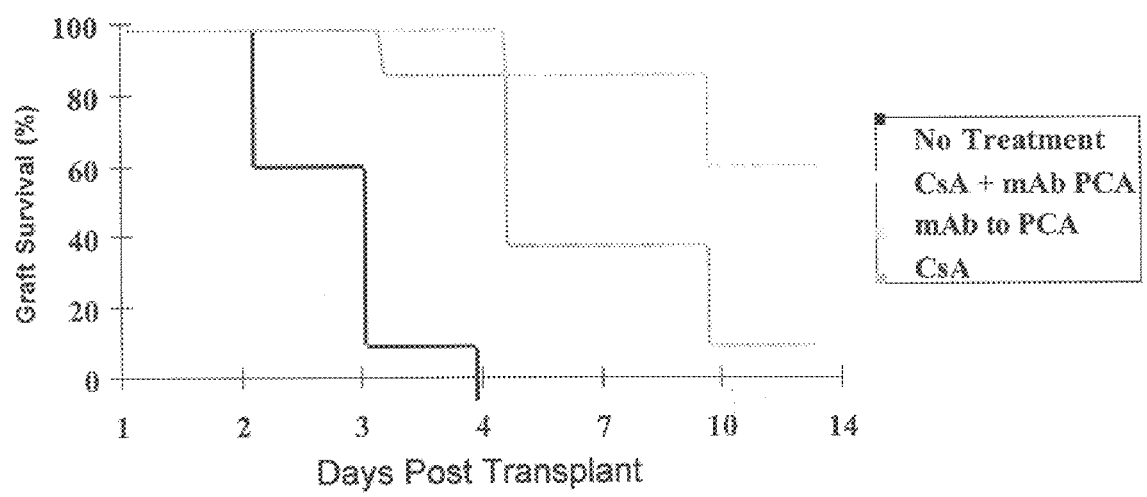
FIG. 12 is a graph showing the prevention of CsA graft rejection by CsA alone or in combination with antibodies to immune coagulants.

Control animals which received no treatment all died within 4 days of transplant and all allografts showed severe necrosis with fibrin deposition. Sixty percent (60%) of animals that received a single injection of cydosporin A died on day 4 and by day 14 only 1 animal (20%) remained alive. Analysis of tissues from all animals showed marked to severe necrosis of the allografts. Animals which received daily injection of monoclonal antibodies to fgl2 had increased survival and by day 14, 60% (3/5) of these animals were alive (FIG. 12). Analysis of allografts showed mild to moderate rejection with no evidence of fibrin deposits. Finally, all animals (5/5) which received a single injection of cyclosporin A and 10 days of monoclonal antibody to fgl2 survived and analysis of their crafts on day 28 showed normal histology.

(b) Xenograft

To study the ability of antibody to fg12 prothrombinase to protect against hyperacute xenograft rejection, livers from Wister rats were perfused with blood from guinea pigs in an isolated liver perfusion apparatus in the presence or absence of 100 mg of antibody to fgl2. Livers were removed aseptically from three groups of Wister inbred rats. The livers were then perfused with oxygenated blood from guinea pigs to which was added either 100 mg of normal mouse IgG1 (Group 1); 100 mg of normal rat blood (Group 2); or 100 mg of antibody to fgl2 prothrombinase for 120 minutes in an isolated perfusion chamber.

Livers perfused with normal mouse IgG1 and albumin became dark, stiff with area of fibrinoid necrosis within 10 minutes and by 30 minutes blood could not be perfused into these livers. In contrast, livers perfused with blood to which antibody to fgl12 had been added appeared morphologically normal, perfusion pressures remained normal and perfusion was continued for the full 120 minutes after which the livers were harvested and examined by routine histology and electron microscopy. In the livers from groups 1 and 2 serum alanine transaminase (ALT) levels rose precipitously from a baseline of 45 IU/L to 12,400 IU/L at 20 minutes increasing to 18,700 IU/L at 30 minutes when the livers were removed from the perfusion device. In contrast serum ALT levels in livers from group 3 remained at near normal: ALT 55 IU/L at 20 minutes; 68 IU/L at 90 minutes and 90 IU/L at 120 minutes. Histology from the livers from groups 1 and 2 showed marked areas of necrosis and hemorrhage with dense intrasinusoidal fibrin deposits. Electron micrographs showed platelet adherence, fibrin deposits and endothelial cell destruction. In contrast, liver architecture appeared near normal in livers from group 3 with only small amount of platelet and fibrin deposits.

These results demonstrate that antibody to fgl2 prothrombinase can prevent hyperacute xeno graft rejection.

Example 3

Induction of Fgl2 Promoter by XenoSera

MATERIALS AND METHODS

Vector Constructs

Restriction enzymes used to create promoter constructs were obtained from GIBCO BRL, Life Technologies, Grand Island, N.Y., USA. All plasmids were purified using Qiagen Maxiprep kits, and grown in DH5 E. coli bacteria (GIBCO BRL).

Figure 13:
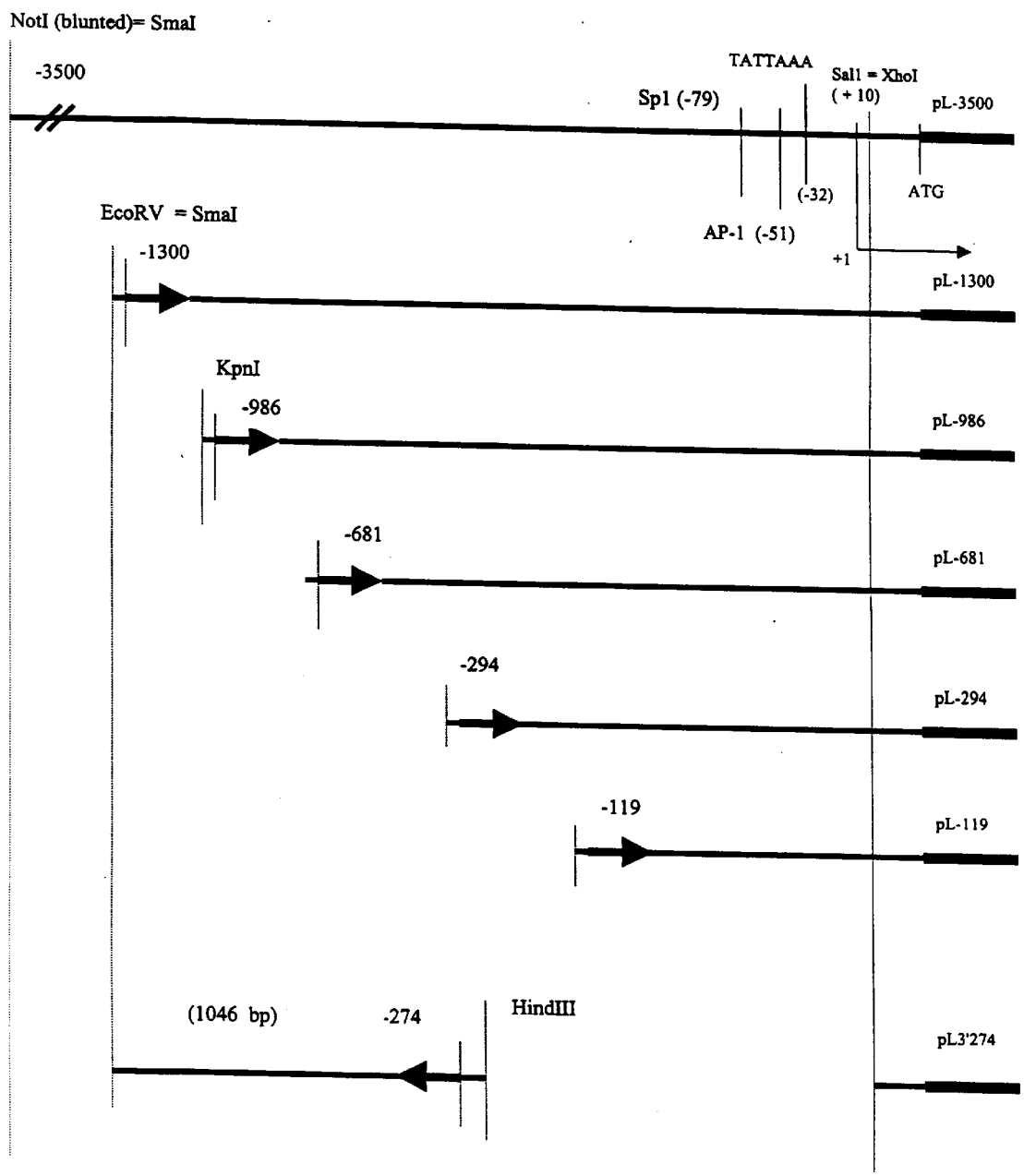
FIG. 13 is a map of the pGL-Basic—fgl-2 Promoter Region Constructs.

DNA from −3.5 kb/+9 bp and −1.3 kb/+9 bp fgl-2 promoter region pGL-2-Basic luciferase constructs (pL-3500, pL-1300) was obtained from clones previously constructed in Dr. Levy's lab (unpublished data). Additional 5' truncation series plasmids and the 3' pL3'274 luciferase vector were constructed first using PCR, followed by cloning into a PCR2.1 plasmid (Invitrogen). Specific portions of the pL-3500 clone were amplified at 35 cycles performed at 95 C for 1 min, 58 C for 1 min, 72 C for 2 min. The downstream 3' reverse primer, present in pGL2-Basic, was fixed for all 5' truncations and was 5'-GAA ATA CM AM CCG CAG MG G-3' (SEQ.ID.NO.; 20) (Promega). The upstream primer used to construct pL-995 was 5'TCT TGG GAA ATC TGG TTA GAG-3 (SEQ.ID.NO.: 21). The upstream primer for pL-681 was 5'-GAG CTG AGT GAT GGG GM GGA-3' (SEQ.ID.NO.: 22). The upstream primer for pL-294 was 5'-GGG CAC TGG TAT TAC MC TGT-3' (SEQ.ID.NO.: 23), and the 5' primer for pL-119 was 5'-CTC CTC CTG TGT GGC GTC TGA-3' (SEQ.ID.NO.: 24). The fixed 5' forward primer for the 3' truncation was 5'-GGA TM GGA GGG CAG GGT GM-3' (SEQ.ID.NO.: 25). The downstream antisense primer for pL3'274 was 5'-ACA GTT GTA ATA CCA GTG CCC-3' (SEQ.ID.NO.: 26). Following PCR, PCR products were ligated and cloned into the PCR2.1 vector. POP2.1 clones were sequenced to check for orientation, and DNA was obtained from desired clones. For the 5' truncations, the PCR2.1 clones were digested with KpnI and SalI, and then ligated and cloned into the pGL2-Basic luciferase vector (Promega) cut with KpnI and XhoI. Each final construct was checked with a specific diagnostic digestion before maxi-preps of DNA were made. For pL3'274, PCR2.1 clones were digested with EcoRV and HindIII, and then ligated and cloned into pGL2-Basic cut with SmaI and HindIII. A summary of the different constructs produced is shown in FIG. 13.

Cell Culture and Sera

SVEC4-10 cells (SV 40 transformed axillary lymph node, vascular endothelial cells from C3H/HeJ adult mice) were purchased from American Type Culture Collection (ATCC), Maryland, USA. The cell cultures were carried, and subcultured as indicated by ATCC, and in 60mm plates (Corning). Cell cultures were kept at 37° C., 5% CO2, and for no longer than sixteen passages.

Porcine serum, rat serum, and fetal bovine serum (FBS) were obtained from GIBCO BRL. Human serum was generated from human plasma (kind gift of Dr. Levy); blood samples were allowed to dot at room temperature for 30 min, and the serum fraction was removed after 15 min of 2900 RPM centrifugation. Autologous C3H serum was purchased from The Jackson Laboratories, Bar Harbor, Maine, USA. All sera were heat inactivated at 56° C. for 45 minutes, aliquotted, and stored at −20° C.

DNA Transfection

All transfections were carried out using Lipofectamine (GIBCO BRL), Prior to transfection, 1–3 X 105 SVEC4-10 cells were seeded per well into six well (35 mm) plates in 2 ml of Dulbecco's Modified Eagle's Medium (DMEM) (GIBCO BRL) containing 10% FBS and 1% Penicillin-Streptomycin (GIBCO BRL). The cells were incubated for 18–24 hrs until they were 70–80% confluent, and then transfected. For each well transfected, 2 µl of lipofectamine was diluted into 100 µl DMEM. This solution was then added to a solution containing 0.5 µg of pGL2-Luciferase vector construct and 0.25 µg of pRSV-fl-Gal vector (Promega) diluted into 100 µl of DMEM. In general, solution5 for four wells were made at once. The Lipofectamine/DNA solution was then vortexed gently, centrifuged for 5 sec at 1500 RPM and allowed to equilibrate for 30 minutes. During this time, the SVEC4-10 cells were washed twice with DMEM. 1 ml of liposomes in DMEM were then added to each well. The transfected cells were incubated at 37° C. for 5–6 hrs, after which the transfection medium was replaced with a fresh 2 ml of DMEM. In total, the cells were serum starved 15–20 hrs in DMEM before inducing for 8–10 hrs with various xenosera and autologous serum at different concentrations in DMEM. Thus, cells which did not receive serum were starved for a total of 23–30 hrs. Each experimental well was done in duplicate.

Transfection Assays (Luciferase and fl-Gal Assays)

Protein Extraction: Following serum stimulation, the cells were harvested for protein extraction. The cells were first washed once with 2 ml of PBS (GIBCO BRL) and then lysed with 200 μl of reporter lysis buffer (Analytical Luminescence Laboratory, Michigan, USA). Culture plates were kept on ice, and the cells were scraped and collected into 1.5 ml Eppendorf tubes. These extracts were stored at −70 C. On the day of the transfection assays, cell lysates under went three freeze and thaw cycles from liquid Nitrogen to 37 C to help release intracellular protein. The protein extracts were then centrifuged for 6 min at 14000 rpm and 4 C to pellet cellular debris. The supernatants containing fl-galactosidase and luciferase were kept on ice until use in the transfection assays.

fl-Galactosidase (fl-gal) Assay: For each sample assayed, 3 μl of 100×Mg solution (0.1M MgCl2, 4.5M fl-mercaptoethanol) was mixed with 33 μl of 2×O-nitrophenyl fl-D-Galacto pyranoside (Sigma Chemical Co., St Louis, Mo., USA), 30 μl of cell extract and 0.1M sodium phosphate (41% w/v 0.2M Na2HPO4 2H2O, 9% w/v 0.2M NaH2PO4 2H2O in 50% w/v H2O) in a 96 well microtiter plate (Costar). The reaction was incubated at 37 C for 30 min, and the optical density was read at 414 nm using a microtiter spectrophotometer. Background fl-gal was determined using a lysis buffer control and was subtracted from the other samples. The fl-gal assay was used to standardize for transfection efficiency.

Luciferase Assay: Cell extracts were assayed for luciferase activity using a MonoLight 2010C luminometer (Analytical Luminescence Laboratory, Michigan, USA). The luciferase reagents were allowed to thaw to room temperature from −20 C. Then 30 μl of protein extract was added to 20 μl of 1× Coenzyme A (Sigma) in a 10 ml luminometer cuvette (Analytical Luminescence Laboratory, Michigan, USA) which was loaded into the luminometer. 100 μl of 1 mM D-luciferin (Analytical Luminescence Laboratory, Michigan, USA) and 100 ul of luciferase lysis buffer (30 mM Tricine, 3 mM ATP, 15 mM MgSO4, 10 mM DTT) are then injected automatically by the luminometer. Light released was measured over a 10 second period. The pGL2-Enhancer vector (Promega) was used as a positive control and the pGL2-Basic vector was used as a negative control. Output data is expressed in raw luciferase units (RLU). Normalized Luciferase data was obtained by dividing the RLU by the fl-gal absorbance and then subtracting off the pGL2-Basic net background luminescence.

Statistical Analysis:

Quantitative data were expressed as means±standard deviations. Statistical analysis was carried out using the student's t-test, and a P value of less than 0.02 was considered statistically significant.

RESULTS

Fgl-2 Promoter Activity is Induced by Xenoserum but only Insignificantly in Autologous Serum in Endothelial Cells.

SVEC4-10 is a murine endothelial cell line derived from C3H/HeJ mice. These cells were chosen to study fgl-2 promoter responses since they have been shown to respond like normal endothehial cells to different cytokines including various interleukis, and TNF- (J. Immunol. 144: 521); IFN-gamma induces MHC class II in a time course identical to normal endothelial cells (J. Immunol. 144: 521). Furthermore, endothelial cells are predicted to be a barrier to successful xenotransplantation and are actively involved in xenograft rejection, so that analysis of fgl-2 transcription in these cells may represent an in vitro model of a xenograft system.

To determine transcriptional activity of the fgl-2 promoter in response to xenoserum versus autologous serum, pL-1300 was transfected in SVEC4-10 cells, following which, they were incubated with either 20% xenoserum, 20% autologous serum, or no serum. Different xenosernm used for induction included FBS, porcine serum, rat serum, and human serum. Autologous serum was from C3H/HeJ mice. Serum-free conditions contained only DMEM. The relative luciferase activity was calculated for each different serum source used, and is expressed in FIG. 14 as a percent relative to serum free conditions. Luciferase activity was normalized for the amount of DNA uptake using a fl-Galactosidase construct as an internal control. Each transfection was done using pL-1300 in duplicate and at least three times. Shown are the mean values and standard deviations for induction with 20% xenoserum (FBS, pig, rat, human) and 20% autologous C3H serum. FBS, porcine serum, and rat serum all induced luciferase expression on average about 4 times higher than in serum free conditions. 20% human serum induced fgl-2 promoter transcriptional activity by an average of 26±0.3 fold. Autologous C3H serum induced only a small increase in fgl-2 promoter activity, and was statistically less than human serum induction (P<0.02).

Figure 15:
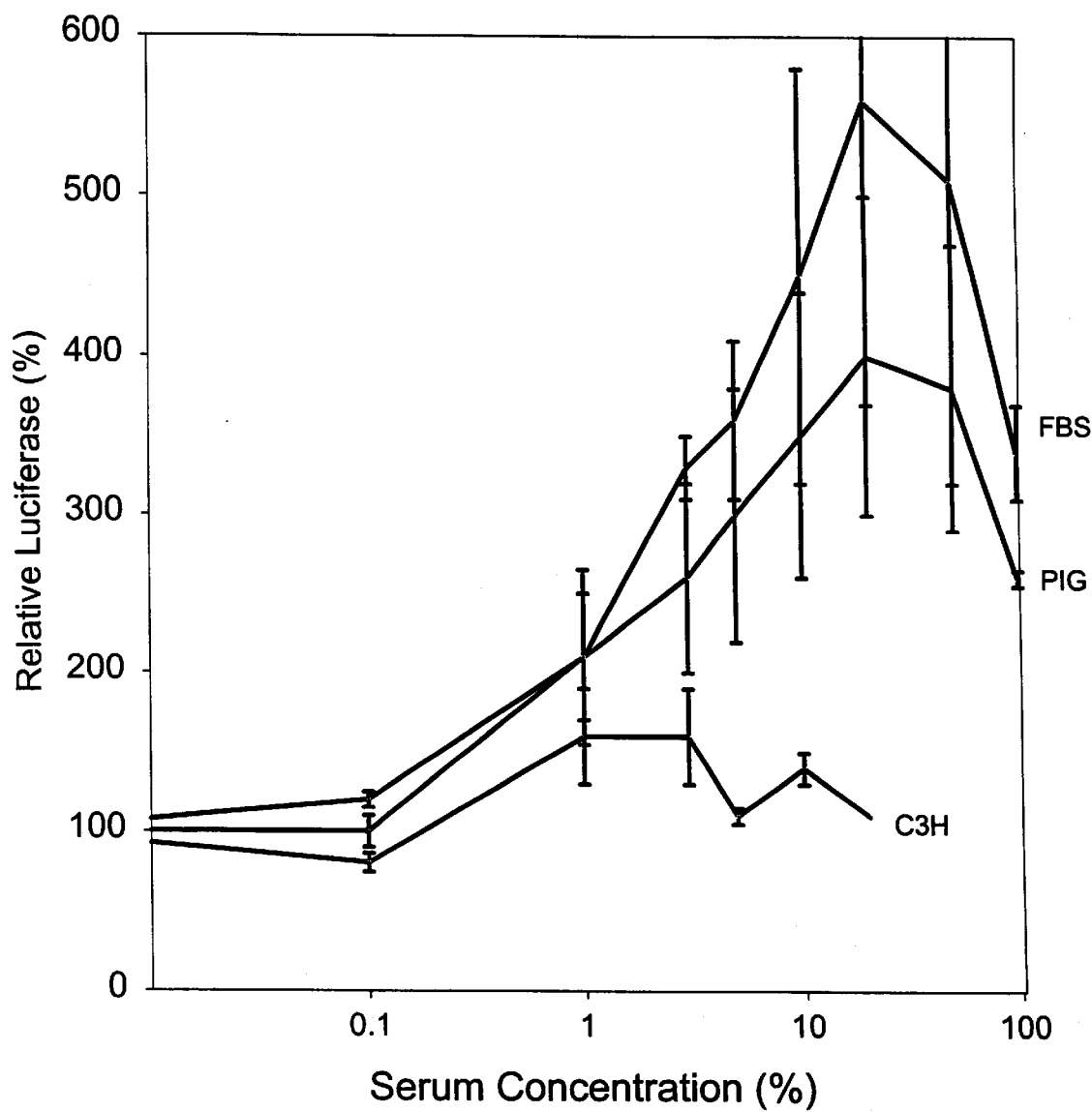
FIG. 15 shows dose response curves for fgl-2 induction in xenoserum versus autologous serum.

Dose response curves for xenoserum versus autologous serum were constructed. In these experiments, SVEC4-10 cells were transfected with pL-1300, and later induced in the presence of 0.1%, 1%, 3%, 5%, 10%, 20%, 5(1%, ad 100% FBS or porcine serum. Again, luciferase activity was expressed as a percent relative to serum free conditions. The dose response curves for FBS, porcine serum and C3H serum are shown in FIG. 15. Both FBS and porcine serum induced luciferase activity in a dose dependent manner to a peak of at least 400% of serum free conditions. Autologous C3H serum failed to induce transcription from the fgl-2 promoter at all doses tested. It is also interesting to point out that the luciferase activity consistently fell in response to incubation with 100% porcine or FBS to levels comparable to 3% xenoserum. This drop in promoter activity may indicate some degree of toxicity associated with high serum levels.

Fetal Bovine Serum Induction is localized to the first 119 bp upstream of the transcription Initiation Site.

To map the position in the fgl-2 promoter region which responds to xenoserum, plasmids with sequential 5' truncations of the promoter were constructed (see FIG. 13). Each construct was transfected into SVEC4-10 cells which were either serum induced with 20% FBS or not induced (DMEM only). The fold increase over the serum free conditions for each construct was then calculated and expressed as a percentage increase. The results are summarized in FIG. 16. pL-3500, containing 3.5 kbp upstream of the transcription initiation site, was inducible to about 215% (a 2.15 fold induction) of the corresponding non-induced samples. Deletion of the promoter region between −3500 and −1300 led to an almost 2 fold increase in luciferase induction, suggesting that this region might bind to regulatory factors which inhibit xenoserum induced transcription. Constructs with sequential 5' truncations of the fgl-2 promoter region (pL- 1300, pL-986, pL-681, pL-294, pL-119) down to nucleotide-119 all were induced to maximal levels (about 350% of non-induced samples) by FBS. Thus, only the first 119 bp upstream of the transcription initiation site of fgl-2 were necessary to maintain optimal induction of fgl-2 transcription by FBS. This observation indicates that there are important DNA sequence elements in this region which are responsible for fgl-2 promoter induction by xenoserum. Most notably, this region of the promoter contains a predicted TATA box at −32, an AP-1 binding site (5'-TGAGTCAG-3') at −51, and an SP1 binding site (5'-CCGCCC-3') at −79 (see FIG. 17E). When the first 274 bp upstream of the transcription initiation site were deleted (pL3'274), no induction of luciferase activity by FBS was obtained. This plasmid reinforces the importance of the proximal promoter region in FBS induction.

DISCUSSION

Figure 14:
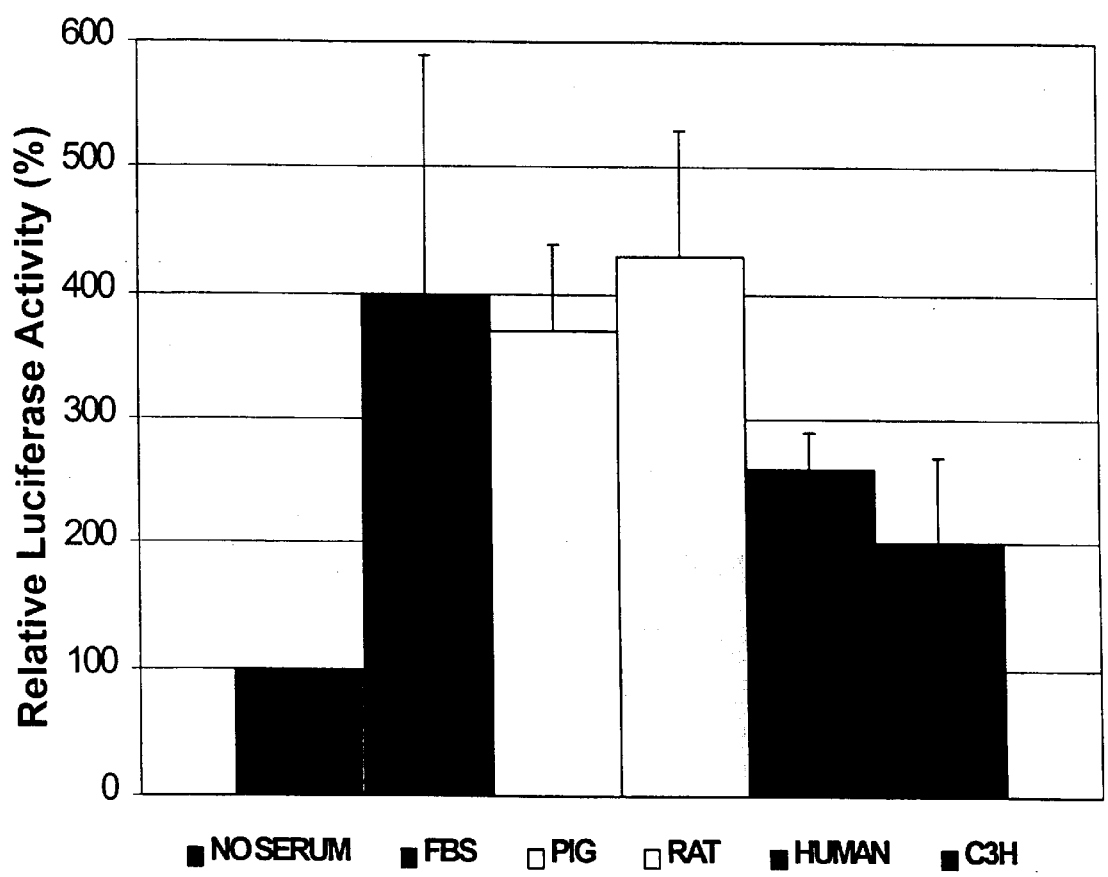
FIG. 14 shows Fgl-2 induction in xenoserum versus autologous serum.

The above results suggest that a 13 kb portion of the fgl-2 promoter region is selectively induced in ECs by xenoserum in a dose dependent manner after 8–10 hours of induction (FIG. 14, FIG. 15). The selective xenoserum induction observed in this study may be as a result of a number of possibilities. One possibility is that the selective induction is mediated through enoreactive natural antibodies (XNAs). According to this view, the autologous C3H serum would not significantly induce fgl-2 promoter activity because it lacks XNAs capable of binding to its EC surface. Insignificant XNA binding would lead to little or no stimulus delivered into the cell to activate fgl-2 transcription. All four xenosera (PBS, pig, rat, human) are known to contain XNAs to various epitopes, some unidentified, on murine ECs which might mediate the fgl-2 promoter activation seen in this study. It is interesting to point out that the most phylogenetically distant xenoserum used, and the only one which contains XNA to Gal 1-3Gal (the human serum), yielded the lowest transcriptional induction from the fgl-2 promoter. This suggests that fgl-2 promoter induction by xenoserum was probably not caused by XNAs to Gal 1-3Gal in the absence of complement. It may still be interesting to test for fgl-2 promoter induction at various time points using human serum that is not heat inactivated or human serum to which complement components are added, so that the XNAs to Gal 1-3Gal may fix complement on the murine ECs.

Another possibility which may help explain the selective inducibility of pL-1300 in ECs by xenoserum is the presence of proinflammatory cytokines. At the site of a vascular xenograft rejection, there is a high level of proinflammatory cytokines and soluble factors produced which act on ECs to help mediate the pathology. Some of these include C5a, IL-1, IL-fl, IL-7, IL-12, IFN-gamma, and TNF- (Platt, J. L. 1996; Parker, W. et al. 1996; Bach, F. H. et al., 1996). Cytokines in the xenoserum used may have contributed to fgl-2 promoter induction. In favour of this hypothesis is the recent observation that the fgl-2 gene is known to be induced by IFN-gamma in monocytes (Lafuse, W. P., et al. 1995). Our lab has also shown that both IL-1 and TNF- can induce ECs to transcribe fgl-2 (Parr, R. L. et al. 1995). Cytokine action may also account for the lower luciferase activity obtained using human serum for induction. It has been shown that certain cytokines do not function across distant species barriers. For instance, human IL-fl and IFN-gamma do not stimulate porcine ECs (Bach, F. H. et al. 1996). Cytokines in high doses are also known to exhibit toxicity to cells, which, in response, will try to decrease their signal transduction. This idea might explain the down regulation of fgl-2 promoter activity seen in 10001% xenoserum from the dose response curve (FIG. 15).

Figure 16:
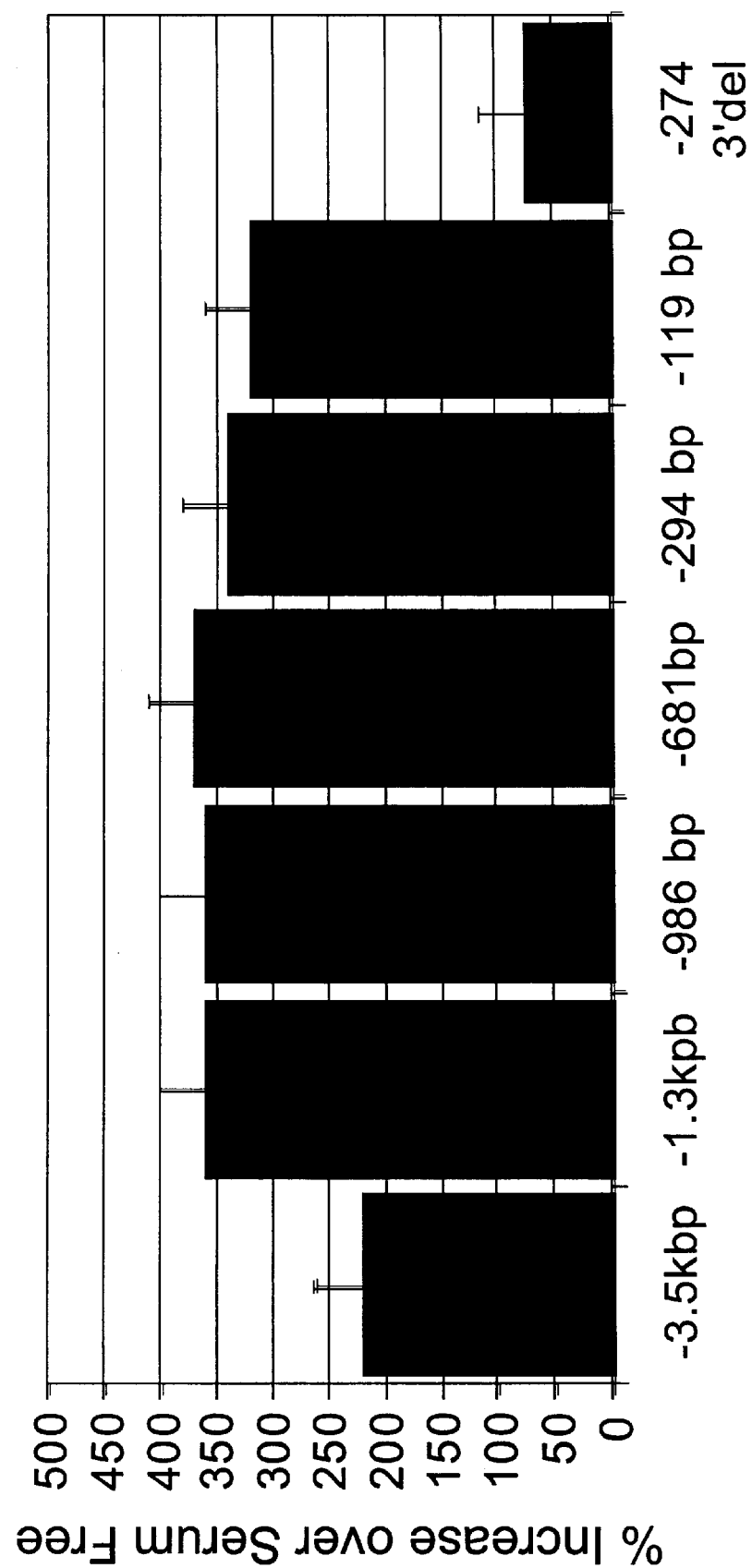
FIG. 16 shows FBS induction of luciferase activity for the 5' deletion series and pL3'274.

The fgl-2 promoter induction by xenoserum (FBS) was mapped to the first 119 bp upstream of the transcription initiation site (FIG. 16). This region is rich in consensus sequences that bind regulatory factors and includes an AP-1 binding site at −51 and an Sp1 binding site at −79 (FIG. 17). Both AP-1 and Sp1 have been shown to be important in high level serum induction of tissue factor, an important procoagulant molecule expressed in xenograft rejection (Mackman, N. et al. 1990). AP-1 sites, and AP-1-like sites, have also been shown to be important agonist response elements. For example, there is an AP-1-like binding site within the human IL-2 gene which responds to IL-1 stimulation (Muegge, K. et al. 1989). Thus, these sites may play a role in fgl-2 promoter induction by various cytokines present at the site of xenograft rejection.

Example 4

Monoclonal Antibody to Fgl2 as Treatment for Recurrent, Unexplained Fetal Loss

Studies were undertaken to study the potential usefulness of monoclonal antibodies to the prothrombinase (fgl2) in the treatment of stress triggered fetal loss. Stressing animals has been shown to result in diminished fertility, mating behaviour, ovulation, implantation, fetal growth and lactation (P. Arck, F. S. Morali, J. Manuel, G. Chaquat and D. A. Clark, Stress Triggered Abortion Inhibition of Protective Suppression and Promotion of Tumor Necrosis Alpha (TNF-α) Releases a Mechanism Triggering Resorptions in Mice, American Journal of Reproductive Immunology 1995;33:74–80).

Exposure to mice to crowded housing conditions, daily handling, forced swimming, loud noise, heat, bright light and physical restraint have been shown to have a deleterious effect on pregnancy outcome in rodents. The type of stress and its effect appears strain dependent. In this CBA/J×DBA/2J matings, ultrasonic sound has been shown to elevate the fetal loss rate. On examination of uteri, it has been shown that a strong pathogenic feature of induced fetal loss is the presence of fibrin deposits.

Therefore, studies were undertaken to determine the efficacy of the monoclonal antibody to fgl2 and its ability to prevent fetal resorption and fetal loss.

The methodology has been well defined. Briefly, after overnight cohabitation of 6–8 week old females (CBA/J) to (DBA/2J) males, the females with vaginal plugs were segregated and assigned to receive no treatment or 10 ug of monoclonal antibody to fgl2 IV daily for 10 days. Both groups of animals (n=10 per group) were subjected to stress which consisted of exposure to ultrasonic sound stress for a battery powered rodent repellant device. On day 13.5 of pregnancy, the females were euthanized by cervical dislocation, uteri were removed and opened and examined for the total number of implantations in a number of resorbing sites recorded.

Figure 18:
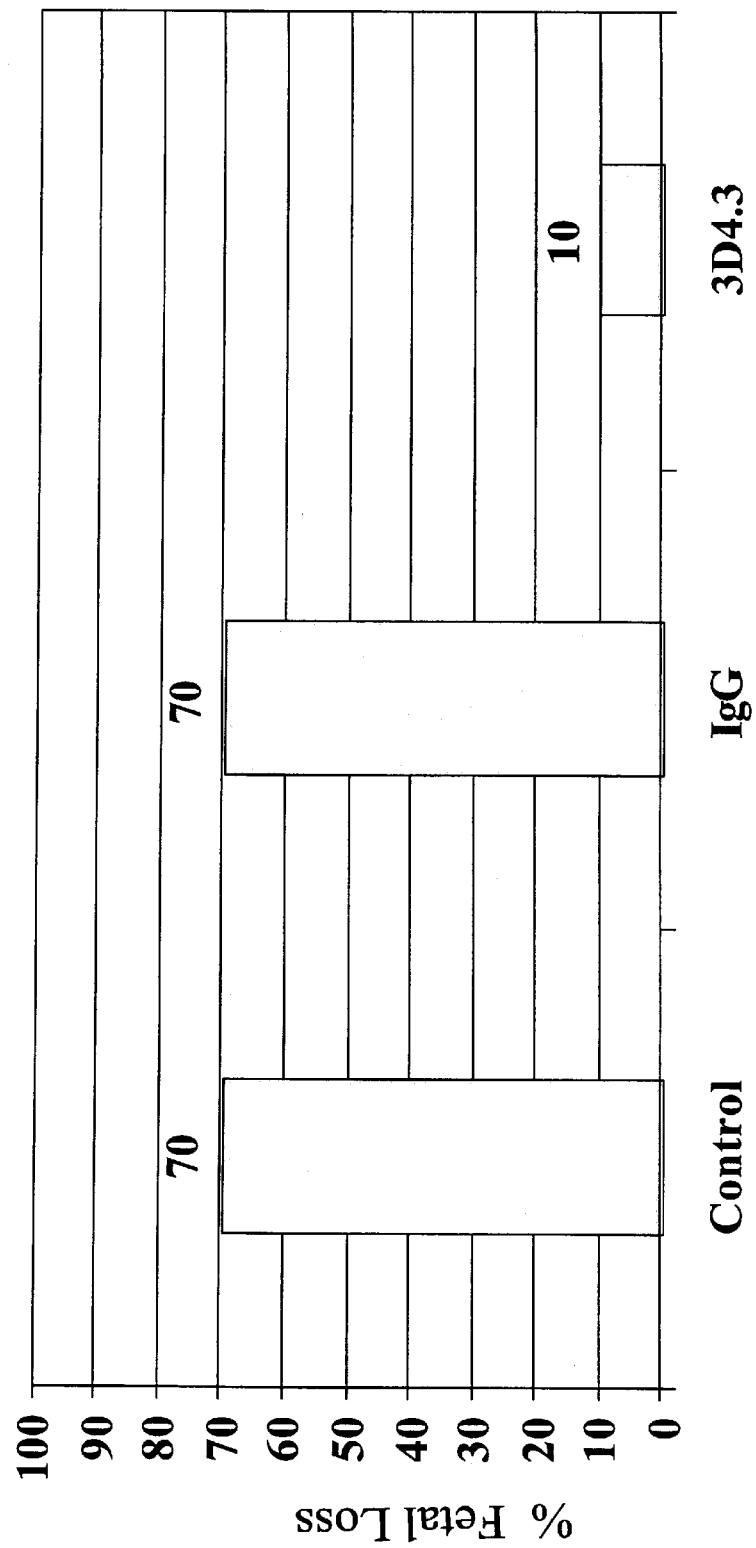
FIG. 18 is a graph showing the prevention of fetal loss by monoclonal antibody 3D4.3.

The results are shown in FIG. 18. Animals which had not been treated had greater than 70% resorbing sites with less than 30% implantations. In contrast, the animals that had received daily injections of the monoclonal antibodies had less than 10% resorbing sites with 90% implantation. This reduction in fetal loss rate was statistically significant at p<0.001. Furthermore, on analysis of uteri in the non-treated animals, there were dense fibrin deposits where these were not detected in animals that had been treated with the monoclonal antibodies.

Example 5

Monoclonal Antibodies to Fgl2 as Treatment for Spontaneous Fetal Loss and Fetal Loss Induced By TNF-α and γ-INTERFERON Studies were done to investigate the potential usefulness of monoclonal antibody to fgl2 prothrombinase in reducing the risk of spontaneous fetal loss and fetal loss induced by TNF-α and γ-interferon in DBA/2-mated CBA/J mice.

To study of the role of monoclonal antibody to fgl2 prothrombinase in fetal loss, the roles of TNF-α and γ-interferon, NK cells, and macrophages in causing fetal loss were directly tested using in vivo cell depletion techniques and mice deficient in the response to interferon.

Cytokines TNF-α and γ-interferon play an important role in fetal loss as their administration increases the fetal loss risk and specific antagonists decrease the fetal loss risk (Chaouat, G., et al., J. Reprod. Fert. 89:447 (1990); Arck, P. C., et al., Amer. J. Reprod. Immunol. 37:262 (1997); Chaouat, G. et al., J. Immunol. 154:4261 (1995); Gendron, R. L. et al., J. Reprod. Fertil. 90:447 (1990)).

In the experiments that follow, the inventor demonstrates that in induced fetal loss the fetal loss is caused by ischemia due to activation of vascular endothelial cell procoagulant which causes thrombosis and inflammation.

Methods

Inbred mice of strains CBA/J and DBA/2 were obtained from Iffa Credo. France C57B1/6J and DBA/2 mice were obtained from the Jackson Laboratories, Bar Harbor, Me. C57B1/6 mice with knockout of the interferon response element IRF-1 were generated as previously described (Duncan, G. S. et al., J. Exp. Med. 184;2043 (1996)) and bred in at the Ontario Cancer Institute, Toronto. CBA/J mice were maintained in the Paris colony under conventional open-top wire cage conditions with food and water ad lib and a 12 hour light-dark cycle. Mice in tie Toronto colony were maintained an a barrier facility. Female CBA/J, C57B1/6 or C57B1/6 IRF-/- mice were mated by overnight cohabitation with a DBA/2J male, and the morning of sighting a vaginal plug was defined as day 0.5 of pregnancy.

Pregnant CBA/J mice were depleted of NK cells by injection of 1 ml rabbit IgG anti-asialoGM1 antibody (Immunocorp, Richmond, Va.) ip on day 6.5 of gestation; phosphate buffered saline (PBS) was used as a control as it has been previously shown to be equivalent to non-immune rabbit IgG (Clark, D. A., Crit. Rev. Immunol. 11:215 (1991)). Macrophage depletion was performed by ip injection of 100 mg/kg silicon dioxide twice a week for 4 weeks prior to mating, as described in Baek, H-S. and J-W. Yoon (J. Virol.64:5708 (1990)). Affinity-purified rabbit IgG neutralizing antibody to mouse procoagulant (fgl2-prothrombinase) was prepared as previously described (Ding, J. W. et al., J. Exp. Med. (1997); Dackiw, A. P. B. et al., Arch. Surg. 131:1273 (1996)); the mice were given a ip injection of 200 μl of a 1/50 dilution of a 5.5 mg/ml preparation of anti-prothrombinase or control rabbit antibody each day beginning on day 3.5 of gestation. Hormonal support of pregnancy sufficient to replace ovarian function was provided in some experiments by injecting 6.7 ng 17β-estradiol+1 mg progesterone in 0.1 ml oil im daily beginning on day 4.5 of gestation (Michael, S. D. et al., Biol. Reprod. 12:400 (1975)). One hundred g of rat monoclonal IgG2b anti-mouse granulocyte antibody RB6-8C5 (Pharmingen) (Stoppacciaro, A. et al., J. Exp. Med. 178:151 (1993)) or isotype control was injected ip on either day 6.5 or on day 8.5 of pregnancy. TNF-α (6 and R&D Systems) 1000 or 2000 units and/or murine recombinant γ-interferon (6 and R&D Systems) 1000 units was injected ip on day 7.5 of pregnancy. On day 13.5 of pregnancy, the mice were sacrificed and the number of resorbing and healthy embryos was counted. In some experiments, the uteri were snap frozen, 5 micron sections were cut, and the tissues were stained with rat monoclonal P4/80 antibody (Caltag, Tebu, France) to macrophages. Briefly, tissue sections were incubated with a 1/30 dilution of F4/60 in PD5 for 30 minutes, and binding was detected using peroxidase-streptavidin with biotin-labelled anti-rat IgG2b second antibody (Secrotec) (Kachkache, M. et al., Biol. Reprod. 45:860 (1991)).

Four to ten mated mice per treatment group were used. The significance of differences in the pooled resorption rate was tested by $c^2$ of Fisher's Exact test where appropriate.

Results and Discussion

NK and Macrophage Depletion and Fetal Loss

Experiment 1, Table 4, shows that ip injection of TNF-α boosted the fetal loss rate of DBA/2-mated CBA/J mice in a dose dependent manner. If the mice had received anti-asialoGM1 antibody treatment, the background rate of fetal loss decreased, as expected (Clark, D. A., Crit. Rev. Immunol. 11:215 (1991); Clark, D. A. et al., Ann. New York Acad. Sci, 626:524 (1990); Chaouat, G. et al., J. Reprod. Fert. 89:447 (1990)), and TNF-α no longer had a significant effect. These data supported the model TNF-α→NK→activated NK→kill embryo. To ensure adequate levels of endogenous macrophage-derived TNF-α, we repeated the experiment and added g-interferon. Experiment 2, shows that γ-interferon alone boosted the fetal loss rate in PBS-pretreated mice to the level achieved with TNF-α, and addition of TNF-α had no significant additional effect. In NK cell-depleted mice, g-interferon failed to boost fetal losses. This suggested the model γ-interferon→macrophages→activated to produce NO→embryo death was not correct. However, when γ-interferon and TNF-α were administered together, more than 80% of the implanted embryos aborted. This suggested an obligatory synergy/co-dependence; in NK cell depleted mice, TNF-α does not work because the NK cell source of γ-interferon has been eliminated, and γ-interferon fails because macrophages dependent on NK cell-derived γ-interferon, have stopped producing TNF-α, an the ip injected cytokine does not stimulate TNF-α production quickly enough such that both cytokines are present simultaneously. A direct NK or macrophage killing mechanism seemed unlikely to explain fetal losses. To further test this idea, the experiment was repeated using macrophage-depleted mice. Experiment 3, shows that macrophage depletion reduced the fetal loss rate. It can be seen that macrophage depletion had no significant effect on the 80% fetal loss rate produced by injecting TNFα+γ-interferon. Tissue staining for F4/80+ macrophages confirmed the silica treatment had been effective and the cytokine treatment did not cause a macrophage infiltration (data not shown). TNF-α+γ-interferon may act synergistically to suppress production of essential gestational hormones by the ovary (Teranova, P. F. and V. M. Rice, Reprod. Immunol. 37:50 (1997)) and such an inhibition could cause fetal losses (Deansly, R., J. Reprod. Fertil. 35:183 (1973); Kaplanski G. et al., J. Immunol. 158:5435 (1997); Michael, S. D. et al. Biol. Reprod. 12:400 (1975)). However, ovarian inhibition should have caused 100% fetal losses (Deansly, R. J. Reprod. Fertil. 35:183 (1973)). Further, when we gave hormone replacement therapy as described above (Michael, S. D. et al. Biol. Reprod. 12:400 (1975)), there was no effect on either the background rate of fetal loss or the high rate of fetal loss produced by 2000 u TNF-α+1000 u γ-interferon (35/41, 86% N=5 control group versus 37/45, 82% N=5 cytokine-treated group, not statistically different).

Cytokine-triggered fetal loss in IRF1-/-mice. TNF-α and γ-interferon act synergistically to induce apoptosis in human trophoblast cell cultures (Yui, J. et al., Placenta 15:819 (1994)). The results shown in Table 4 could be explained by a direct apoptotic action on trophoblast. However, the cytokine CSF-1 is present in vivo, and this may abrogate the apoptotic effects of TNF-α and γ-interferon (Yui, J. et al., Placenta 15:819 (1994); Pollard, J. W. et al., Nature 330:484 (1987)). To test for a direct effect on trophoblast in mice, IRF1−/−females were mated to DBA/2 (+/+) males. Here the fetal trophoblast expresses IRF1 but maternal tissues do not. As shown in Table 5, pregnant IRF−/−females had low background fetal loss rates and were completely resistant to TNF-α+γ-interferon. The C57B1/6 (+/+) female coisogenic with the IRF1−/−mice also had a low resorption rate, but aborted dramatically when the cytokine treatment was given. These data indicated the cytokines act on the mother and not on trophoblast to induce fetal losses.

Anti-flg2 Prothrombinase Antibody Blocks Fetal Losses, and Granulocytes Contribute to the Process of Endothelial Disruption.

Since neither macrophages nor NK cells seemed necessary for TNF-α+γ-interferon to act, the most logical target appeared to be the vascular endothelial cell. These cytokines stimulate surface expression of pro-coagulant (flg/2-prothrombinase, which is distinct from tissue factor) and the subsequent clotting process is known to lead to ischemic damage in a variety of inflammatory disease models such as hepatitis and endotoxic shock (Ding, J. W. et al., J. Exp. Med. (1997); Dackiw A. P. B. et al., Arch. Surg. 131:1273 (1996); Levi, M. et al., J. Cin. Invest. 93:114 (1994)).

The results of treatment of DBA/2-mated CBA/J mice with antibody to flg2 prothrombinase are shown in Table 6. Treatment with antibody to flg2 prothrombinase reduced the background risk of fetal loss from 38% to 4.5%; the reduction is statistically significant at p<0.001. The frequency of chromosome abnormalities in mouse embryos is 4% (Smith, W. B. et al., J. Immunol. 157:360 (1996)).

Table 6 also shows that treatment with antibody to flg2 prothrombinase markedly reduced the fetal loss risk induced by TNF-α+γ-interferon from 87% to 13% (p<0.001). There is no statistically significant difference between the fetal loss risk in mice which received TNF-α+γ-interferon and antibody to flg2 prothrombinase (13%), and the fetal loss risk in mice which did not receive TNF-α+γ-interferon, but received antibody to flg2 prothrombinase (4.5%). Therefore, antibody to 11g2 prothrombinase almost completely prevented fetal loss induced by TNP-α+γ-interferon.

Thus, it has been found in this study that neither NK cells nor macrophages are required for fetal loss, that cytokine-dependent fetal loss in CBA×DBA/2 mice is mediated by the procoagulant fgl2 prothrombinase, that the cytokines act on the mother and not on embryonic trophoblast, and that the embryo dies from ischemia due to activation of vascular endothelial cell procoagulant fgl2 which causes thrombosis. The present inventor has demonstrated that treatment of DBA/2-mated CBA/J mice with antibody to flg2 prothrombinase reduces the background risk of fetal loss and almost completely prevents fetal loss induced by TNF-α+γ-interferon.

Example 6

Expression of fgl2 Prothrombinase Using a Baculovirus Expression System

The example demonstrates that the fgl2 protein may be expressed using a baculovirus expression system.

cDNA of murine fgl2 was subcloned into the vector pBlueBacHis2A. This was then used to generate a recombinant baculovirus by homologous recombination with the wild type baculovirus ACMNPV. By infecting insect cells (Sf9 or High 5) with the recombinant virus, a fusion hfgl2 protein with six histidine residues followed by an enterokinase site at the N-terminus was expressed. The lysate from High 5 cells infected with the recombinant virus was analyzed for the presence of hfgl2 protein by Western blot using the polyclonal rabbit anti-mouse fgl2 antibody. Uninfected High 5 cells and those infected with wild type AcMNPV were used as controls in all studies. The conditions for protein expression were optimized (see Results section) and the fusion protein was purified using the ProBond resin, which contains nickel for binding the histidine residues.

Figure 19:
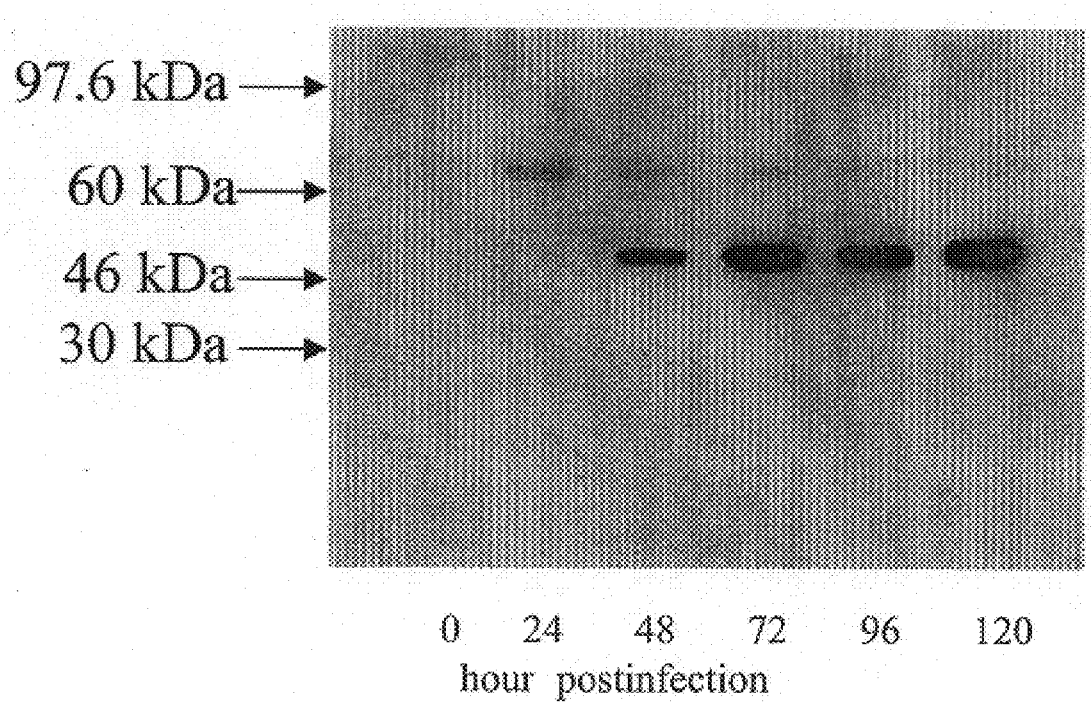
FIG. 19 is a gel showing the time course of expression of murine fgl2.

Recombinant viruses containing the hfgl2 gene sequence were screened by PCR and selected as putative clones. Pure viral clones were obtained after several rounds of plaque purification. Western blot analysis was performed using polyclonal rabbit anti-hfgl2 antibody to demonstrate expression of hfgl2 fusion protein. Preliminary experiments were performed to determine the optimal conditions for protein expression. Amounts of protein expressed by Sf9 and High 5 insect cells were compared. High 5 cells expressed greater quantities of protein compared to Sf9 cells. Recombinant protein production was detectable by 48 h and reached maximal levels at 72 h, remaining at the same level for up to 5 days after infection. The time course of hfgl2 expression is shown in FIG. 19 MOI=MOI is of 5 or 10 pfu/cell produced similar levels of protein expression. Based on these observations, we decided to infect High 5 cells with virus at an MOI of 5 pfu/cell, and harvested the cells on day 3 post-infection for optimal protein production.

Figure 20:
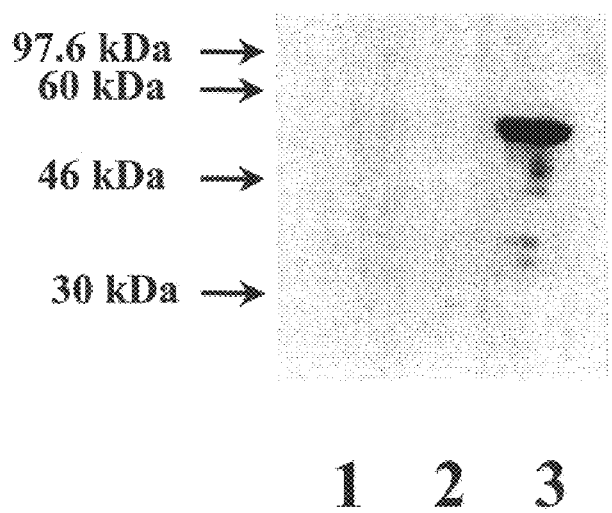
FIG. 20 is a Western blot showing expressed fgl2.
Figure 21:
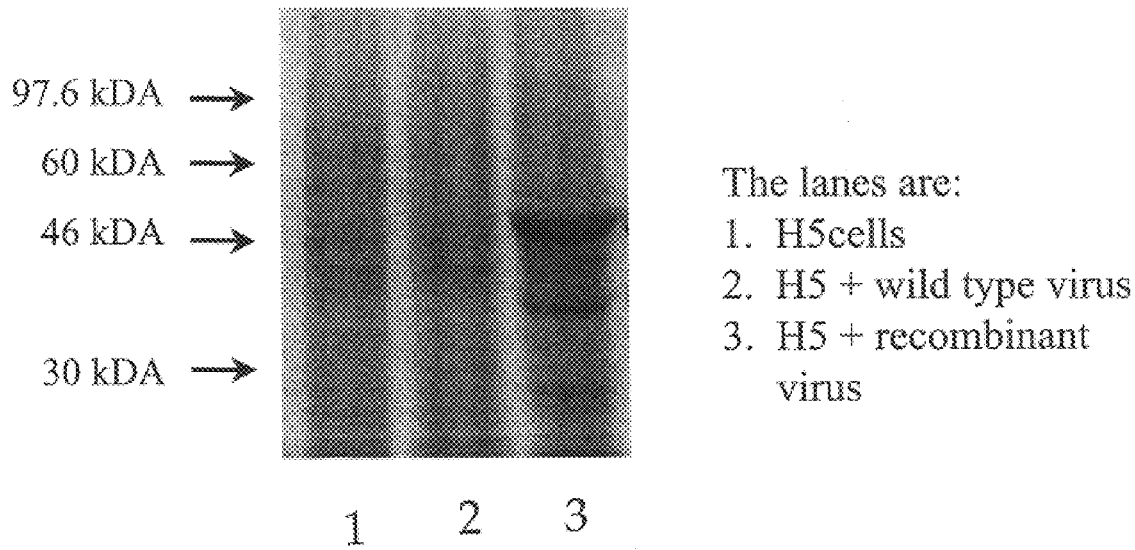
FIG. 21 is a Coomassie blue stained gel showing expressed fgl2.

As we mentioned previously, the hfgl2 fusion protein was attached to a polyHis tag at the N terminus. Purification of the protein was performed using the Probond resin under denatured conditions ñ no success was met when performed under native conditions. Western and Coomassiebue staining were used to detect the expressed prothrombinase (FIGS. 20 and 21 respectively). The protein was observed to have a molecular weight of ~60 kDa. Murine fgl2 fusion protein was not detected in the medium.

Example 7

Functional Analyses of the mfgl2 Fusion Protein

Functional analyses on the procoagulant activity of the expressed hfgl2 fusion protein prepared in Example 6 were conducted to confirm that the expressed fusion protein acts as a direct prothrombinase, like the native protein.

Experimental Approach

One-stage Clotting Assay

This assay for fgl2 prothrombinase was used to directly measure preoagulant activity. High 5 cells infected with recombinant virus expressing the hfgl2. fusion protein were subjected to cycles of freeze thawing. They were then assayed for their ability to accelerate the spontaneous clotting time of recalcified platelet-poor normal human plasma as previously described (Levy & Edgington, 1980). Results were quantitated by comparison with serial dilutions of standard rabbit brain thromboplastin. Activities from cells infected with the recombinant virus were compared with those uninfected and wild-type virus infected, and with the purified protein alone. Proteins involved in the coagulation pathway require a phospholipid bilayer for functional activity; therefore purified protein was reconstituted into the insect cells and macrophages to determine their PCA activity. Additional PCA assays were performed with human plasma deficient in coagulation factors II, V, VII, VIII, X, and XII to determine the nature (factor dependence) of the expressed PCA.

Prothrombin Cleavage Assay

To determine if the expressed fusion protein acts as a direct prothrombinase, the prothrombin cleavage assay was performed as previously described (Schwartz et al., 1982). 125I-prothrombin was incubated with High 5 cells, both infected or uninfected with the recombinant virus. Purified mfgl2 fusion protein was also studied to determine its ability to cleave prothrombin. Human Factor Xa in the presence of Russell's viper venom (RVV) was used as a positive control. Samples were run on 10% SDS-PAGE and analyzed by autoradiography for 125I-prothrombin and their cleavage products.

One-stage Clotting Assay

PCA was measured for uninfected cells, wild and recombinant virus-infected cells, and the soluble protein (Table 7). Only cells infected with the recombinant virus express PCA, and no activity were detected from the purified soluble protein. This result suggested that the presence of the six histidine residues and the enterokinase site at the N-terminus of mfgl2 fusion protein did not completely affect its clotting ability. The PCA results using factor deficient plasmas are shown in Table 8. The PCA expressed by recombinant virus infected cells was independent of all factors except II (prothrombin) which suggests the expressed mfgl2 fusion protein acts similarly as the native protein to be a direct prothrombinase.

A second set of dotting assays was done to determine if the addition of soluble mfgl2 protein prevents PCA expression by cells infected with recombinant virus. Our results suggested that the soluble protein was incapable of preventing the clotting induced by the cell lysate. Nonetheless, preliminary results from reconstitution of purified protein into insect cells shows partial PCA activity recovery (Table 9).

Prothrombin Cleavage Assay

Figure 22:
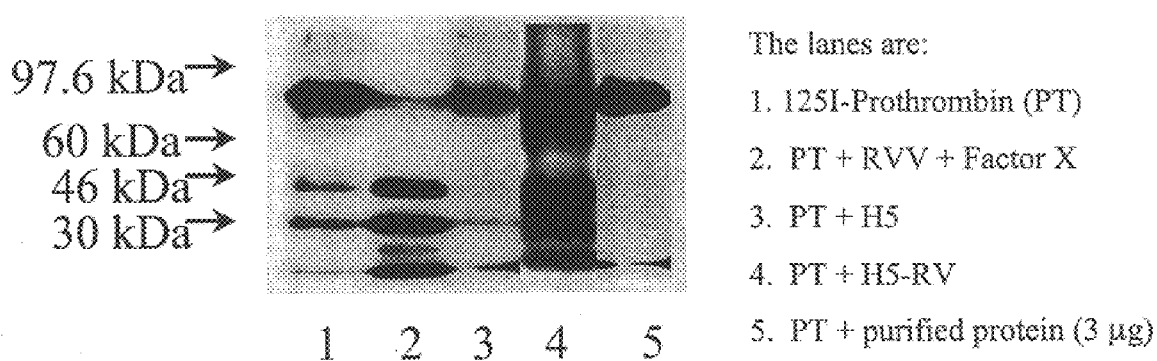
FIG. 22 is an autoradiograph showing 125I labelled fgl2.

The ability of mfgl2 fusion protein to cleave prothrombin to thrombin was examined by the prothrombin cleavage assay. In FIG. 22, a single high molecular weight species of intact 125I-prothrombin was noted after incubation with buffer and calcium alone (first panel). Addition of human factor X in the presence of calcium and factor V produced cleavage products corresponding to known derivatives of prothrombin (second panel). Similar products were seen when incubating 125I-prothrombin with homogenates from recombinant virus infected cells (forth panel). However, incubation of 125I-prothrombin with uninfected High 5 cell homogenates or purified protein exhibited no prothrombin cleavage (third and fifth panels respectively). These results were consistent wit the observations from our one-stage clotting assay. Low molecular weight products were seen when 125I-prothrombin was incubated with homogenates from wild type virus infected cells (data not shown). This might be explained by the expression of protease in wild type infected insect cells (Vialard et al., 1995).

Having illustrated and described the principles of the invention in a preferred embodiment, it should be appreciated to those skilled in the art that the invention can be modified in arrangement and detail without departure from such principles. We claim all modifications coming within the scope of the following claims.

All publications patents and patent applications are herein incorporated by reference in their entirety to the same extent as if each individual publication, patent or patent application was specifically and individually indicated to be incorporated by reference in its entirety.

Below full citations are set out for the references referred to in the specification and detailed legends for some of the figures are provided.

FULL CITATIONS FOR REFERENCES REFERRED TO IN THE SPECIFICATION

Arck, P. C., et al. 1997. Amer. J. Reprod. Immunol. 37:262.

Bach, F. H., H. Winkler, C. Ferran, W. Hancock, and S. C. Robson. 1996. Delayed xenograft rejection. Immunol. Today 17:379.

Baek, H-S. and J-W. Yoon. 1990. J. Virol. 64:5708.

Barrett, A. J., and N. D. Rawlings. 1995. Families and clans of serine peptidases. Archives of Biochemistry and Biophysics. 318(2):247–250.

Breathnach R. and P. Chambon. 1981. Organization and Expression of Eucaryotic Split genes coding for proteins. Ann. Rev. Biochem. 50:349–383.

Brentens J. R., 1987. Glomerular procoagulant activity and glomerulonephritis. Lab Invest. 57:107–111.

Bucher, P. 1990. Weight Matrix Description of four eukaryotic RNA polymerase II promoter elements derived from 502 unrelated promoter sequences. J. Mol. Biol. 212:563–578.

Bucher, P. and E. N. Trifonov. 1986. Compilation and analysis of eukaryotic POL II promoter sequences. Nuc. Adds. Res. 14(24):10009–10026.

Chanuat, G. et al. 1990. J. Reprod. Fert. 89:447.

Chaouat, G. et al. 1995. J. Immunol. 154:4261.

Chisari, F. V. 1995. Hepatitis B Virus Immunopathogenesis. Annu. Rev. Immunol. 13:29–60.

Clark, D. A. 1991. Crit. Rev. Immunol. 11:215 (1991).

Clark, D. A., et al. 1998. Cytokine dependent abortion in CBA×DBA/2 mice is mediated by the procoagulant fgl2 prothrombinase. J. Immunol. 160:545.

Cole E. H., Cardella C. J., Schulman J., and Levy G. A., 1985. Monocyte procoagulant activity and plasminogen activator: role in human renal allograft rejection, Transplantation, 40:363.

Cole E. H., Schulman J., Vrowitz M., Keystone E., Williams C., and Levy G. A., 1985. Monocyte procoagulant activity in glomerulonephritis associated with systemic lupus erythematosus, J. Clin. Invest., 75:861.

Cole E. H., Sweet J., Levy G. A., 1986. Expression of Macrophage procoagulant activity in murine systemic lupus erythematosus. J Clin Invest. 78;887–893.

Cole E. H., Glynn M. F. X., Laskin C. A., Sweet J., Mason N., and Levy G. A., 1990. Ancrod improves survival in murine systemic lupus erythematosus. Kidney Int. 37:29 35.

Dackiw, A. P. B. et al. 1996. Arch. Surg. 131:1273.

Davie E. W., Fujikawa K., and Kisiel W., 1991. The coagulation cascade: Initiation, maintenance and regulation, Biochemistry, 30:10363.

Davit, E. W., K. Fujikawa, and W. Kisiel. 1991. The coagulation Cascade: Initiation, Maintenance, and Regulation. Biochem. 30(43):10363–10370.

Deansly, R. 1973. J. Reprod. Fertil. 35:183.

Dindzans, V. J., E.Skamene, and G. A. Levy. 1986. Susceptibility/Resistance to Mouse Hepatitis Virus Strain 3 and Macrophage Procoagulant Activity Are Genetically Linked And Controlled by Two Non-H-2-Linked Genes. J. Immunol. 137(7):2355–2360.

Ding, J. W. et al. 1997. J. Exp. Med.

Ding, J. W., Q. Ning, M. F. Liu, A. Lai, J. Leibowitz, K. M. Peltekian, E. H. Cole, L. S. Fung, C. Holloway, P. A. Marsden, H. Yeger, M. J. Phillips, and G. A. Levy. 1997. Fulminant Hepatic Failure in Murine Hepatitis Virus Strain 3 Infection: Tissue-Specific Expression of a Novel fgl2 Prothrombinase. J. Virol. 71: 9223.

Duncan, G. S. et al. 1996. J. Exp. Med. 184:2043.

El-Baruni K., Taylor I., Roth S., Francis J. L., 1990. Factor X -activating procoagulant in normal and malignant breast tissue. Hematol Oncol. 8:323–332.

Francis J. L., El-Baruni K., Roth O. S., Taylor I., 1988. Factor X—activating activity in normal and malignant colerectal tissue. Thromb Res. 52;207–217.

Fung L., Neil G., Leibowitz J., Cole E. H., Chung S., Crow A., and Levy G. A., 1991. Monoclonal antibody analysis of a unique macrophage procoagulant activity by murine hepatitis virus strain 3 infection. J. Biol. Chem., 266:1789.

Fung, L., G. Neil, J. Leibowitz, E. H. Cole, S.Chung, A. Crow, and G. A. Levy. 1991. Monoclonal Antibody Analysis of a Unique Macrophage Procoagulant Activity Induced by Murine Hepatitis Virus Strain 3 Infection. J. Biol. Chem. 266(3):1789–1795.

Gendron, R. L. et al. 1990. J. Reprod. Fertil. 90:447.

Gordon S. G., Cross B. A., 1981. A factor X—activating cysteine proteinase from malignant tissue. J Clin Invest. 67:1665–1671.

Grecy, C. L., Davies, W. A., 1981. A mechanism of migration inhibition in delayed-type hypersensitivity. II. Lyphokines promote procoagulant activity of macrophages in vitro. J Immunol 126:1059.

Hamilton, K. K., R. Hattori, C. T. Esmon, and P. J. Sims. 1990. Complement proteins C5b-9 induce vesiculation of the endothelial plasma membrane and expose catalytic surface for assembly of the prothrombinase enzyme complex. J. Biol. Chem. 265: 3809.

Hancock W. W., Rickles F. R., Ewan V. A., Atkins R. C., 1986. Immunohistological studies with A1-3, a monoclonal antibody activating human monocytes and macrophages. J Immunol. 136:2416–2421.

Holdsworth S. R., Thompson N. M., Glascal E. F., Atkins R. C., 1979. The effect of defibrination on macrophage participation in rabbit nephrotoxic nephritis; studies using glomerular culture and electron microscopy. Clin. Exp. Immunol., 37:38–43.

Holdsworth S. R., Tipping P. G., 1985. Macrophage-induced glomerular fibrin deposition in Experimental Glomerulonephritis in the Rabbit. J Clin Invest. 76:1367–1374.

Holzknecht, Z. E., and J. L. Platt. 1995. Identification of porcine endothelial cell membrane antigens recognized by human xenoreactive antibodies. J. Immunol. 154:4565.

Hynes, R. O. 1992. Integrins: versatility, modulation, and signalling in cell adhesion. Cell 69: 11.

Jacob Churg, Jay Bernstein, and Richard J. Glassock., 1995. Renal Disease, second edition, pp155.

Javahery, R., A. Khachi, K. Lo, D. Zenzie-Gregory, and S. T. Smale. 1994. DNA sequence requirements for transcriptional initiator activity in mammalian cells. Mol. Cell Biol. 14(1):116–127.

Jurd, K. M., R. V. Gibbs, and B. J. Hunt 1996. Activation of human prothrombin by porcine aortic endothelial cells—a potential barrier to xenotransplantation. Blood Coagulation Fibrinol. 7: 336.

Kachkache, M. et al. 1991. Biol. Reprod. 45:860.

Kanfer A., Deprost D., Guettier C., Nochy D., LeFloch V., Hinglies N., Druet P., 1987. Enhanced glomerular procoagulant activity and fibrin deposition in rats with mercuric chloride-induced autoimmune nephritis. Lab Invest. 57:138–143.

Kaplanski G. et al. 1997. J. Immunol. 158:5435.

Key N. S., Vercellotti G. M., Winkelmann J. C, Moldow C. F., Goodman, J. L., Esmon, N. L., Esmon, C. T., and Jacob, H. S., 1990. Infection of vascular endothelial cells with herpes simplex virus enhances tissue factor activity and reduces thrombomodulin expression, Proc. Natl. Acad. Sci. U.S.A., 87:7095.

Kim P. C. W., Levy G. A., Craig M., Cullen J., and Cohen 2., 199. Immune responses during small-intestinal allograft rejection; correlation between procoagulant activity and histopathology. Transplant. Proc., 23:2477.

Kincaid-Smith, P., 1972. The treatment of chronic mesangiocapillary glomerulonephritis with impaired renal function. Med. J. Aust. 2:587–592.

Kohler, G., and Milstein, C, 1975. Nature 256:495–497.

Laemmli, U., 1970. Nature 227:680.

Lafuse, W. P., et al. 1995. The cytotoxic T lymphocyte gene FIBLP with homology to F Fibrinogen fl and gamma subunits is also induced in mouse macrophages by IFN-gamma. Cellular Immunology. 163: 187.

Lee, W. M. 1993. Acute Liver Failure. New England J. Med. 329;1662–1872.

Levi, M. et al. 1994. J. Clin. Invest. 93:114.

Levy G. A. & Edgington T. S. 1980. Lymphocyte cooperation is required for amplification of macrophage procoagulant activity. J. Exp. Med. 151, 1232–1244

Levy, G. A., Leibowitz, J. L., and Edgington, T. S., 1981. Induction of monocyte procoagulant activity by murine hepatitis type 3 virus parallels disease susceptibility in mice, J Exp Med., 154:1150.

Levy, G. A., Schwartz, B. S., Curtiss, L. K., Edgington, T. S., 1981. Plasma lipoprotein induction and suppression of the generation of cellular procoagulant activity in vitro, J. Clin. Invest., 67:1614.

Levy, G. A., P. J. MacPhee, L. Fung, M. M. Fisher, and A. M. Rappaport, 1983. The Effect of Mouse Hepatitis Virus Infection on the Microcirculation of the Liver. Hepatology 3(6):964–973.

Levy, G. A. and Cole, E. H., 1994. *Role of Procoagulant Activity in Health and Disease.*

Lyberg, T., and Prydz, H., 1981. Phorbol esters induce synthesis of thromboplastin activity in human monocytes, Biochem. J., 194:699.

Mackman, N., B. J. Fowler, T. S. Edgington, and J. H. Morrissey. 1990. Functional analysis of the human tissue factor promoter and induction by serum. Proc. Natl. Acad. Sci 87: 2254.

MacPhee, P. J., V. J. Dindzans, L. Fung, and G. A. Levy, 1985. Acute and Chronic Changes in the Microcirculation of the Liver in Inbred Strains of Mice Following Infection with Mouse Hepatitis Virus Type 3. Hepatology 5(4):649–660.

Maier, R. and Ulevitch, R., 1981. The induction of a unique procoagulant activity inrabbit macrophases by bacterial lipopolysaccharide, J. Immunol., 127;1596.

Michael, S. D. et al. 1975. Biol. Reprod. 12:400.

Muegge, K., T. Williams, J. Kant, M. Karin, R. Chiu, A. Schmidt, U. Siebenlist, H. Young, and S. Durum. 1989. Science 246:249.

Muller-Berghause, G. and Mann, B., 1973. Precipitation of ancrod induced soluble fibrin by aprotinin and norepinephrine. Thormb Res 2:305–322.

Nduwimana, J., L. Guenet, I. Dorval, M. Blayau, J Y. Le Gall, and A. Le Treut, 1995. Proteases. Ann Biol Clin. 93: 251–264.

Nemerson, Y., 1992. The tissue factor pathway of blood coagulation, Semin. Hematol., 29:170.

Pangasnan, R. S., Devereux. D., De Cunzol, P., Carpe, G. I., 1992. The production of a factor X activator by a Methycholanthrene—induced rat fibrosarcoma. Thromb Haemostasis 68:407–412.

Parker, W., S. Saadi, S. S. Lin, Z. E. Holzknecht, M. Bustos, and J. L. Platt. 1996. Transplantation of discordant xenografts: a challenge revisited. Inmuunol. Today 17: 373.

Parr, R. C., L. Fung, J. Reneker, N. Myers-Mason, J. L. Leibowitz, and G.Levy, 1995. Association of Mouse Fibrinogen-Like Protein with Murine Hepatitis Virus-Induced Prothrombinase Activity. J. Virol. 69(8):5033–5038.

Platt, J. L. 1996. The immunological barriers to xenotransplantation. Crit. Rev. Imm. 16:331.

Platt, J. L., A. P. Dalmasso, B. J. Lindman, N. S. Ihrcke, and F. H. Bach. 1991. The role of C5a and antibody in the release of heparan sulfate from endothelial cells. Eur. J. Immunol. 21: 2887.

Pollak, V. H., Glueck, M., Weiss, M., Lebron-Bergs, A., Miller, M. A., 1982. Defibrination with ancrod in glomerulonephritis: Effects on clinical and histologic findings and on blood coagulation. Am J Nephrol. 2:195–207.

Pollard, J. W. et al. 1987. Nature 330:484.

Pope, M., O. Rotstein, E. Cole, S. Sinclair, R. Parr, B. Cruz, R. Fingerote, S. Chung, R. Gorczynski, L. Fung, J. Leibowitz, Y. S. Rao, and G.Levy, 1995. Pattern of Disease After Murine Hepatitis Virus Strain 3 Infection Correlates with Macrophage Activation and Not Viral Replication. J. Virol. 69(9):5252–5260.

Rawlings, N. D and A. J. Barrett, 1994. Families of serine proteases pp 19–61. In Methods in Pnzymology. Vol 244. Ed A. J. Barrett.

Richardson, D. L., Pepper, D. S., Kay, A. B., 1976. Chemotaxis for the monocytes by fibrinogen-derived peptides. Br J Haematol.

Rickles, F. R. and Edwards, R. L., 1983. Activation of blood coagulation in cancer: Trousseau's syndrome revisited, Blood, 62:14.

Rickles, F. R. and Rick, P. D., 1977. Structural features of Salmonella typhimurium lipopolysaccharide required for activation of tissue factor in human mononuclear cells, J. Clin. Invest., 59:1188.

Rivers, R. P. A., Hathaway, W. E., and Weston, W. L., 1975. The endotoxin-induced coagulant activity of human monocytes, Br. J. Haematol, 30:311.

Rosenthal, G., Levy, G. A., Rotstein, O. D., 1988. Surg. Forum 24:103–105.

Rothberger, H, Barringer, M., and Meredith, J., 1984. Increased tissue factor activity of monocytes/macrophages isolated from canine renal allografts, Blood:63, 623.

Ruegg, C., and R. Pytela, 1995. Sequence of a human transcript expressed in T-lymphocytes and encoding a fibrinogen-like protein. Gene. 160:257–262.

Saadi S., and J. L. Platt. 1995. Transient perturbation of endothelial integrity induced by a antibodies and complement. J. Exp. Med. 181: 21.

Saadi, S., N. S. Ihrcke, and J. L. Platt. 1995. Pathophysiology of xenograft rejection, in Principles of Immunomodulatory Drug Development in Transplantation and Autoimmunity, Lieberman, R. and Morris, R., Eds., Raven Press, New York, N.Y.

Schitknecht, E., Ada, G. L., and Braciale, T. J., 1984. Macrophage procoagulant inducing activity of influenza-specific effector T cells, Cell. Immunol., 89: 342.

Schwartz, B. S. and Edgington, T. S., 1981. Immune complex-induced human monocyte procoagulant activity, J. Exp. Med., 154:892.

Schwartz B. S., Levy G. A., Fair D. S. & Edgington T. S. 1982. Murine lymphoid procoagulant activity induced by bacterial lipopolysacchaide and immune complexes is a monocyte prothrombianse. J. Exp. Med. 153, 1464–1479

Schwartz, B. and Edgington, T., 1982. Immunol. 128:1037.

Shands, J. W., 1985. Macrophage factor X activator formation; metabolic requirements for synthesis of components. Blood 65:169–175.

Shapiro, C. N, 1993. Epidemiology of hepatitis B. Pediatr. Infect. Dis. J. 12:433–437.

Shapiro, C. N., and H. S. Margolis, 1990. Hepatitis B Epidemiology and Prevention. Epidemiological Reviews. 12:221–227.

Sinclair, S. B., A. Wakefield, G. A. Levy, 1990. Fulminant Hepatitis. Springer Seminars In Immunopathology. 12:33–45.

Sitrin, R. G., Benfer-Kaltreider, H., Goldyne, M. E., 1984. Prostaglandin E is required for the augmentation of procoagulant activity of LPS stimulated rabbit alveolar macrophages. J Immunol 132:867.

Smith, W. B. et al. 1996. J. Immunol. 157:360.

Steinberg, A. D., 1994. Semin Immunol. 6:55.

Stoppacciaro, A. et al. 1993. J. Exp. Med. 178:151.

Teranova, P. F. and V. M. Rice. 1997. Reprod. Immunol. 37:50.

Thomson, N. M., Moran, J., Simpson, I. J., Peters, D. K., 1976. Defibrination with Ancrod in Nephrotoxic Nephritis in Rabbits. Kidney Int. 10:343–347.

Tipping, P. G., Holdsworth S. R., 1986. The participation of macrophages, glomerular procoagulant activity, and Factor VIII in glomerular fibrin deposition. Studies in anti-GBM antibody induced glomenilonephritis in rabbits. Am J Pathol 124: 10.

Tipping, P. G., Worthington, L. A., Holdsworth, S. R., 1987. Quantitation and Characterization of glomerular procoagulant activity in Experimental Glomerulonephritis. Lab Invest. 56:155–159.

Tipping, P. G., Dowling, J. P., Holdsworth, S. R., 1988. Glomerular procoagulant activity in human proliferative glomerulonephritis. J Clin Invest 81:119–125.

Tsumagari, T., Tanaka, K., 1984. Effects of fibrinogen degradation products on glomerular mesangial cells in culture. Kidney Int 26:712.

Vialard J. E., Arif B. M. & Richardson C. D. 1995. Introduction to the molecular biology of baculoviruses. In: Methods in molecular biology, vol 39: Baculovirus expression protocols. Human Press Inc., Totowa, N. J.

Vassalli, P., McCluskey, R. T., 1971. The pathogenetic role of the coagulation process inglomerular diseases of immunolgical origin. Adv Nephrol 1:47.

Watanabe-Fukunga, R. et al., 1992. Nature 356:314.

Wiggins, R. C., 1985. Hageman factor and experimental nephrotoxic nephritis in the rabbit. Lab Invest. 53:335–348.

Wiggins, R. C., Glatfeller, A., Brukman, J., 1985. Procoagulant activity in glomeruli and urine of rabbits with nephrotoxic nephritis. Lab Invest. 53:156–165.

Wilson, C. B., Dixon, F. J., 1974. Diagnosis of immunopathologic renal disease. Kidney Int. 5:389.

Wright, R., 1990. Viral hepatitis comparative epidemiology. British Medical Bulletin. 46(2)548–558.

Yui, J. et al. 1994. Placenta 15:819.

TABLE 1

| Clan | Example | Consensus |
|---|---|---|
| SA | chymotrypsin 10 families | H D G.SG |
| SB | Subtilisin 1 family | D HGT GTS . . . G |
| SC | Carboxypeptidase 5 families | C G.S D H |
| SE | B lactamase 4 families | S . . . K S.N D |
| SF | Lex A 3 families | SM G KR |
| SG | Omptin 5 families | not identified |

TABLE 2

| Clan | Example | Consensus |
|---|---|---|
| CA | Papain 3 families | CW H N.W W |
| CB | Picornains 4 families | H C(G) |
| CC | HC-proteinase 2 families | GYCY VDH HV |

- many uncharacterized families

TABLE 3

| PRIMER | SEQUENCE | 5' POSITION | tm 2(A + T) + 4(G + C) |
|---|---|---|---|
| HUFLP1 | GCA AAC AAT GAA ACA GAG GAA A (SEQ.ID.NO.: 16) | 100 | 60 |
| HUFLP2 | ATT GCC CTA TTA GAT AAC GAA TAC (SEQ.ID.NO.: 17) | 1399 | 64 |
| HUFLP3 | AAC GGA GAC CCA GGC AGA AAC (SEQ.ID.NO.: 27) | 349 | 66 |
| HUFLP4 | CTT CGG GAG CTG AAT AGT CAA (SEQ.ID.NO.: 28) | 243 | 62 |
| HUFLP5 | GAC AGC AAA GTG GCA AAT CTA (SEQ.ID.NO.: 29) | 553 | 60 |
| HUFLP6 | TTC TGG TGA AGT TGG TGC TCC (SEQ.ID.NO.: 30) | 832 | 64 |
| HUFLP7 | CAA AAG AAG CAG TGA GAC CTA CA (SEQ.ID.NO.: 31) | 693 | 66 |
| HUFLP8 | TTA TCT GGA GTG GTG AAA AAC TT (SEQ.ID.NO.: 15) | 1125 | 62 |
| HUFLP9 | TGA CCA AGA GTA AGG AAA TGA (SEQ.ID.NO.: 32) | 908 | 58 |
| HUFLP10 | TGA CTG TAT TTG TTC TTG GCT G (SEQ.ID.NO.: 33) | 639 | 62 |
| HUFLP11 | TTC TGG GAA CTG TGG GCT GTA (SEQ.ID.NO.: 34) | 1134 | 64 |
| HUFLP12 | CCA GCT TCA TCT TTA CAG T (SEQ.ID.NO.: 35) | 43 | 54 |
| HUFLP13 | AAT CAC TCT GTT CAT TCC TCC (SEQ.ID.NO.: 36) | 1353 | 60 |
| HUFLP14 | GAA ATA ATA TGC ATT GAA A (SEQ.ID.NO.: 37) | −173 | 36 |
| HUFLP14R | AAC GCA CAG GAC GAG A (SEQ.ID.NO.: 38) | −96 | 58 |
| HUFLP15 | TTG ACA TCC TTT GAG ATA T (SEQ.ID.NO.: 39) | 1459?? | 50 |
| HUFLP16 | ATG GGG CAT TGG GGA GC (SEQ.ID.NO.: 40) | −427 | 56 |
| HUFLP17 | GGC TAT CTC CTC TTC CTG T (SEQ.ID.NO.: 41) | −118 | 58 |
| HUFLP18 | TGA GCT ATG CCA GTG TCT GT (SEQ.ID.NO.: 42) | −755 | 60 |
| HUFLP19 | CAA GCG TAG TAT ACC AAA T (SEQ.ID.NO.: 43) | −288 | 52 |
| HUFLP20 | AAG GCA GGA AAG AGG AAC (SEQ.ID.NO.: 44) | −961 | 54 |
| HUFLP21 | GAC AAA GGA ATA GAA AGT AGC (SEQ.ID.NO.: 45) | −601 | 58 |
| HUFLP22 | CAG GGC AAA AAT CTA AAT G (SEQ.ID.NO.: 46) | −1092 | 52 |
| HUFLP23 | GCC CAG AGA GCA GGT AGA A (SEQ.ID.NO.: 47) | −883 | 60 |
| HUFLP24 | CCA GCC AGG GTT GAA ATA (SEQ.ID.NO.: 48) | 3' end | 54 |
| HUFLP25 | GCC CTG TCA GTC ATT TTG (SEQ.ID.NO.: 49) | promoter:not used | 54 |
| HUFLP26 | AAA AAC CTA CCA GTA GTC T (SEQ.ID.NO.: 50) | 3' end | 52 |
| HUFLP28 | TTG GGG TGA CAT TAT GC (SEQ.ID.NO.: 51) | 2399 | 50 |
| HUFLP29 | TGA GCA GCA CTG TAA AGA TG (SEQ.ID.NO.: 52) | 16 | 58 |
| HUFLP30 | GTG GCT AAA AGT GCT TGG GT (SEQ.ID.NO.: 53) | 1350 | 60 |

TABLE 4

Role of asialoGM1 + NK cells and macrophages in fetal loss

| Expt. | Day 6.5 treatment | Day 7.5 treatment | N[a] | Day 13.5 assay resorptions/total | % fetal losses |
|---|---|---|---|---|---|
| 1. | PBS | PBS | 8 | 23/56 | 41% |
|  | PBS | 1000 u TNF-α | 8 | 43/60 | 72%[b] |
|  | PBS | 2000 u TNF-α | 8 | 57/64 | 89%[c] |
|  | anti-asialoGM1 | PBS | 8 | 10/59 | 19%[d] |
|  | anti-asialoGM1 | 1000 u TNF-α | 8 | 12/63 | 16%[e] |
|  | anti-asialoGM1 | 2000 u TNF-α | 8 | 12/55 | 22%[e] |

TABLE 4

Role of asialoGM1 + NK cells and macrophages in fetal loss

| Expt. | Day 6.5 treatment | Day 7.5 treatment | N[a] | Day 13.5 assay resorptions/total | % fetal losses |
|---|---|---|---|---|---|
| 2. | PBS | PBS | 16[f] | 43/101 | 43% |
|  | PBS | 1000 u IFN-γ[g] | 16 | 79/93 | 85%[g] |
|  | PBS | 1000 u IFN-γ + TNF-α[h] | 16 | 74/89 | 83%[h] |
|  | anti-asialoGM1 | PBS | 16 | 11/71 | 15%[d] |
|  | anti-asialoGM1 | 1000 u IFN-γ | 16 | 12/98 | 12%[e] |
|  | anti-asialoGM1 | 1000 u IFN-γ + TNF-α[h] | 16 | 89/104 | 86%[h] |
| 3. | ctrl[i] | PBS | 8 | 36/88 | 41% |
|  | ctrl | IFN-γ + TNF-α[j] | 8 | 65/80 | 81%[i] |
|  | SiO$_2$[k] | PBS | 8 | 14/55 | 25%[k] |
|  | SiO$_2$ | IFN-γ + TNF-α[j] | 8 | 52/65 | 80%[j] |

Footnotes to Table 4:
[a]N represents number of pregnant mice per group.
[b]Significant increase in fetal loss rate, P < 0.005 by c2.
[c]Significant increase in fetal loss rate compared to PBS control, P < 0.005 by c2; significant difference compared to lower dose of TNF-α, P < 0.05.
[d]Significant reduction in fetal loss rate by anti-asialoGM1 antibody compared to PBS control, P < 0.005 by c2.
[e]No signfficant booting of fetal loss rate compared to PBS injected anti-asialoGM1-treated group.
[f]Result from 2 independent experiments giving same result have been pooled.
[g]g-interferon (IFN-g) significantly booted fetal loss rate, P < 0.005 by c2.
[h]TNF-a was given at 1000 u and 2000 u in separate experiments with IFN-g and gave similar result; the data have been pooled for ease of presentation. The fetal loss rate was significantly boosted P < 0.005 by c2.
[i]Untreated CBA/J female mice mated to DBA/2 males.
[j]1000 u IFN-g + 2000 u TNF-a significantly boosted fetal loss rate, P < 0.005 by c2.
[k]CBA/J mice injected twice a week for 4 weeks with 100 mg/kg silicon dioxide before mating significantly reduced fetal loss rate, P < 0.05 by c2.

TABLE 5

Cytokine-triggered resorption in C57B1/7 IRF +/+ and IRF −/− mice

| Mating combinations | Day 7.5 treatment | N | Day 13.5 assay resorption/total | % fetal losses |
|---|---|---|---|---|
| IFR1 +/+ X +/+[a] | nil | 5 | 3/39 | 7.7% |
| IFR1 +/+ X +/+ | IFN-γ + TNF-α | 4 | 16/22 | 73%[b] |
| IRF1 −/− X +/+[c] | nil | 7 | 3/57 | 5.3% |
| IRF1 −/− X +/+ | IFN-γ + TNFα[d] | 9 | 5/76 | 6.5% |

[a]Normal C57B1/6 females (+/+) mated to DBA/2 males (+/+).
[b]Significant increase in fetal loss rate P < 0.001, Fisher's Exact test.
[c]Female C57B1/6 mice homozygous for a defective IRF gene (IRF −/−) were mated to normal DBA/2 males (+/+).
[d]1000 u IFN-γ and 2000 u TNF-α was injected

TABLE 6

Antibody to fg12 prothombinase prevents fetal losses in CBA/J X DBA/2 mice

| Pretreatment group | Day 7.5 treatment | N | Day 13.5 assay resorption/total | % fetal losses |
|---|---|---|---|---|
| Control Rabbit IgG | nil | 8 | 21/56[a] | 38% |
| Control Rabbit IgG | IFN-γ + TNF-α[b] | 8 | 48/55 | 87%[c] |
| Rabbit IgG anti-fg12 | nil | 9 | 3/66 | 4.5%[d] |
| Rabbit IgG anti-fg12 | IFN-γ + TNF-α[b] | 9 | 9/68 | 13%[e] |

[a]Result from two independent experiments which gave the same result.
[b]1000 u IFN-g and 2000 u TNF-a was injected ip.
[c]Significant increase in fetal loss rate P < 0.001 compared to no cytokine control group, Fisher's Exact test.
[d]Significant reduction in spontaneous fetal loss rate P < 0.001 compared to no cytokine control group, Fisher's Exact test.
[e]Significant reduction in fetal loss rate P < 0.001 compared to cytokine-treated controls, Fisher's Exact test. No significant difference compared to anti-fg1/2-treated mice which did not receive an injection of cytokines.

TABLE 7

Expression of procoagulant activity in High 5 cells infected with recombinant AcMNPV

|  | PCA Time (sec) | Miliunits/2 × 10$^b$ cells |
|---|---|---|
| High 5 cells | >240 | <1 |
| High 5 cells + Wild type AcMNPV | 126 ± 5 | 9 ± 3 |
| High 5 cells + Recombinant AcMNPV | 76 ± 3 | 319 ± 73 |
| Purified protein (3 μg) | 220 | <1 |

TABLE 8

Effect of coagulation factor-deficient plasmas on PCA expression

| Plasma | PCA Time (sec) | Milliunits/2 × 10$^b$ cells |
|---|---|---|
| Normal | 72 ± 4 | 418 ± 104 |
| Deficient in: |  |  |
| Factor VII | 54 ± 4 | 1624 ± 406 |
| Factor X | 105 ± 5 | 40 ± 14 |
| Factor V | 67 ± 2 | 592 ± 89 |
| Factor II | >240 | <1 |

TABLE 9

The procoagulant acitivity after constitution of the purified protein

|  | PCA Time (sec) | Milliunits (mU/2 × 10$^6$ cells) |
|---|---|---|
| H5 | >240 | <1 |
| Purified protein (3μg) | 220 | <1 |
| H5 + purified protein (3 μg) | 42 | 3634 |
| H5 + recombinant virus (RV) | 89 | 127 |

TABLE 9-continued

The procoagulant acitivity after constitution of the purified protein

| | PCA | |
|---|---|---|
| | Time (sec) | Milliunits (mU/2 × 10⁶ cells) |
| H5 cells + RV + Purified protein (20 ng) | 57 | 1254 |
| H5 cells + RV + Purified protein (100 ng) | 54 | 1543 |
| H5 cells + RV + Purified protein (3 μg) | 50 | 2053 |
| H5 cells + RV + Purified protein (3 μg) | 34 | 6434 |

We claim:

1. A method of preventing or reducing fetal loss comprising administering an effective amount of an inhibitor of Fgl2 to an animal in need thereof, wherein the inhibitor is an antibody that binds to Fgl2.

2. A method according to claim 1 wherein the antibody is a monoclonal antibody that binds to a human Fgl2, wherein said human Fgl2 has the amino acid sequence as shown in SEQ ID NO. 2.

3. A method according to claim 2 wherein the antibody binds an epitope of human Fgl2, wherein said epitope comprises the amino acids at positions 364–378 DRYPSGNCGLYY of (SEQ.ID.NO. 18).

4. A method for preventing or reducing fetal loss in an animal comprising administering a therapeutically effective amount of a composition comprising an antibody that binds to Fgl2 in admixture with a suitable diluent or carrier.

* * * * *